(12) United States Patent
Sato et al.

(10) Patent No.: US 6,864,254 B1
(45) Date of Patent: Mar. 8, 2005

(54) INHIBITOR FOR 20-HETE-YIELDING ENZYME

(75) Inventors: Masakazu Sato, Tokyo (JP); Noriyuki Miyata, Tokyo (JP); Takaaki Ishii, Tokyo (JP); Yuko Kobayashi, Tokyo (JP); Hideaki Amada, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/869,103

(22) PCT Filed: Nov. 1, 2000

(86) PCT No.: PCT/JP00/07694

§ 371 (c)(1),
(2), (4) Date: Jun. 22, 2001

(87) PCT Pub. No.: WO01/32164

PCT Pub. Date: May 10, 2001

(30) Foreign Application Priority Data

| Nov. 1, 1999 | (JP) | 11-311137 |
| Dec. 28, 1999 | (JP) | 11-372347 |
| Jun. 15, 2000 | (JP) | P2000-180472 |
| Jun. 15, 2000 | (JP) | P2000-180473 |
| Jun. 15, 2000 | (JP) | P2000-180476 |
| Jun. 15, 2000 | (JP) | P2000-180478 |

(51) Int. Cl.$^7$ .................. A81K 31/155; C07C 317/40; C07C 323/65; C07C 323/12; C07C 323/19

(52) U.S. Cl. .................. 514/238.8; 514/235.8; 514/248; 514/256; 514/258; 514/262; 514/310; 514/311; 514/312; 514/328; 514/331; 514/346; 514/357; 514/359; 514/364; 514/366; 514/367; 514/370; 514/380; 514/406; 514/411; 514/416; 514/424; 514/427; 514/428; 514/430; 514/438; 514/443; 514/449; 514/452; 514/459; 514/456; 514/467; 514/568; 514/471; 514/633; 514/637; 544/237; 544/265; 544/278; 544/235; 544/327; 544/335; 546/157; 546/166; 546/171; 546/143; 546/219; 546/240; 546/300; 546/334; 548/143; 548/151; 548/166; 548/190; 548/233; 548/260; 548/362.5; 548/375.1; 548/444; 548/484; 548/513; 548/542; 548/562; 548/570; 549/54; 549/75; 549/78; 549/288; 549/307; 549/357; 549/377; 549/427; 549/453; 549/460; 549/491; 549/510

(58) Field of Search .................. 514/229, 238.8, 514/248, 256, 258, 262, 310, 311, 312, 328, 331, 346, 357, 359, 364, 366, 367, 370, 380, 406, 411, 416, 424, 427, 428, 430, 438, 443, 449, 452, 459, 456, 467, 468, 471, 633, 637; 544/166, 237, 265, 278, 235, 327, 335; 546/157, 166, 171, 143, 219, 240, 300, 334; 549/54, 78, 75, 288, 307, 357, 377, 427, 453, 460, 491, 510; 548/143, 151, 166, 190, 233, 260, 362.5, 375.1, 444, 484, 513, 542, 562, 570

(56) References Cited

U.S. PATENT DOCUMENTS

| 4,237,168 A | * 12/1980 | Reifschneider | 424/326 |
| 4,465,841 A | * 8/1984 | Cereda et al. | 548/346 |
| 5,238,964 A | 8/1993 | Kikuchi et al. | 514/634 |

FOREIGN PATENT DOCUMENTS

| DE | 2543179 | 4/1976 | |
| DE | 27 17 437 | * 10/1978 | |
| JP | 53-132529 | 11/1978 | C07C/131/00 |
| JP | 0 132 881 | 2/1985 | C07C/131/00 |
| WO | WO 99/43310 | 9/1999 | |

OTHER PUBLICATIONS

Zinner et al. (Chem.–Ztg. (1974), 98(3), 159). Abstract.*
Hussein et al. (Bull. Coll. Sci., Univ. Baghdad (1973), 14, 79–87), Abstract.*
International Search Report.
Hayakawa, K. et al., "Quantitative Structure–Activity Relationships of Fungicidal N–Phenylformamidoximes", J. Pesticide Sci. vol. 17, No. 1, pp. 17–25 (1992).
Alonso–Galicia, M. et al., "Inhibition of 20–HETE Production Contributes to the Vascular Responses to Nitric Oxide", Hypertension, vol. 29, No. 1, pp.320–325 (1997).

* cited by examiner

*Primary Examiner*—Bruck Kifle
(74) *Attorney, Agent, or Firm*—Sughrue Mion, PLLC

(57) ABSTRACT

An inhibitor for 20-hydroxyeicosatetraenoic acid production which comprises as the active ingredient a specific hydroxyformamidine derivative or a pharmacologically acceptable salt thereof. It is useful especially as a remedy for kidney diseases, cerebrovascular diseases, or circulatory diseases. The novel hydroxyformamidine derivative or pharmacologically acceptable salt thereof is also provided.

10 Claims, No Drawings

INHIBITOR FOR 20-HETE-YIELDING ENZYME

TECHNICAL FIELD

The present invention relates to hydroxyformamidinobenzene derivatives inhibiting a synthase of 20-hydroxyeicosatetraenoic acid (20-HETE) biosynthesized from arachidonic acid.

BACKGROUND ART

Prostaglandins produced by cyclooxygenase and leukotrienes produced by lipoxygenase have been well known as physiologically active substances synthesized from arachidonic acid. Recently, it has been elucidated that 20-HETE, which is produced from arachidonic acid by the cytochrome P450 family enzymes, functions in various manner in vivo *J. Vascular Research*, vol. 32, p.79 (1995)). It has been reported that 20-HETE induces constriction or dilation of important organs such as the kidneys and the cerebral blood vessels, and causes cell proliferation, and it is suggested that 20-HETE plays important physiological roles in vivo, and participates in various kidney diseases, cerebrovascular diseases, or circulatory diseases (*J. Vascular Research*, vol. 32, p. 79 (1995); *Am. J. Physiol.*, vol. 277, p. R607 (1999); and the like.

DISCLOSURE OF THE INVENTION

An object of the present invention is to provide an inhibitor for production of 20-HETE, which participates in constriction or dilation of microvessels in the important organs such as the kidneys and the cerebral blood vessels, or in causing cell proliferation.

As a result of various studies in order to solve the above problem, the present inventors have found that aromatic compounds having a specific substructure unexpectedly possess the inhibitory activity for 20-HETE synthase, to accomplish the present invention.

That is, one mode of the present invention corresponds to an inhibitor of 20-hydroxyeicosatetraenoic acid synthase, comprising, as an effective ingredient, a hydroxyformamidine derivative represented by the general formula (1) as follows:

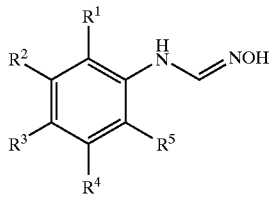

(1)

[wherein $R^1$ to $R^5$ are identical or different and represent a hydrogen atom; a hydroxyl group; a carboxyl group; a halogen atom; a $C_{1-14}$ alkyl group; a $C_{1-14}$ alkyl group substituted with 1 to 6 halogen atoms; a $C_{2-6}$ alkenyl group; a $C_{1-6}$ alkoxy $C_{1-6}$ alkyl group; a $C_{3-8}$ cycloalkyl $C_{1-6}$ alkyl group; a $C_{2-6}$ alkynyl group; a $C_{3-8}$ cycloalkyl group; a $C_{3-8}$ cycloalkoxy group; a $C_{2-10}$ alkanoyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkylgroup; a di($C_{1-6}$ alkyl)amino $C_{2-6}$ alkoxycarbonyl group; amono- or di($C_{1-6}$ alkyl)amino group; a $C_{2-10}$ alkanoylamino group; a $C_{2-6}$ alkanoylamino group substituted with a $C_{1-6}$ alkyl group; a benzoylamino group; a carbamoyl group; a carbamoyl group mono-substituted or di-substituted with $C_{1-6}$ alkyl or phenyl groups; an N—(N', N'-di($C_{1-6}$ alkyl)amino $C_{1-6}$ alkyl)carbamoyl group; a cyano group; a cyano $C_{1-6}$ alkyl group; a nitro group; a thiol group; a phenoxy group; a phenoxy group substituted with 1 to 3 substituents from the group consisting of $C_{1-6}$ alkyl groups, $C_{1-6}$ alkoxy groups, and halogen atoms; a phenylthio group; a nitrophenylthio group; a $C_{1-6}$ alkylsulfonyl group; a phenylsulfonyl group; a $C_{1-6}$ alkylthio $C_{1-6}$ alkyl group; a phenylsulfonyl $C_{1-6}$ akylthio group wherein the benzene ring is substituted with 1 to 5 halogen atoms; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an α-cyanobenzyl group; an α-cyanobenzyl group substituted with 1 to 5 halogen atoms; a benzyl group substituted with a bicyclo [2.2.1]-hept-5-en-2,3-dicarboxyimidyl group; a benzoyl group; a styryl group; a styryl group substituted with 1 to 5 substituents selected from the group consisting of $C_{1-6}$ alkoxy groups and di($C_{1-6}$ alkyl)amino alkyl groups; a pyrrolidino group; a piperidino group; amorpholino group; apyridyl group; apyrimidinyl group; a pyrimidinyl group substituted with 1 to 3 substituents selected from the group consisting of $C_{1-6}$ alkyl groups and $C_{1-6}$ alkoxy groups; a phthalimidoyl group; a phthalimidoyl group substituted with 1 to 3 halogen atoms; an N-carbazolyl group; a dioxopiperidinyl group substituted with 1 to 3 $C_{1-6}$ alkyl groups; aphenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from the group consisting of halogen atoms, $C_{1-6}$ alkyl groups, and $C_{1-6}$ alkoxy groups; a pyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of halogen atoms, $C_{1-6}$ alkyl groups, and $C_{2-6}$ alkoxycarbonyl groups; a thienopyrimidinylthio group; a thienopyrimidinylthio group substituted with 1 to 3 $C_{1-6}$ alkyl groups; a thienopyridylthio group; a thienopyridylthio group substituted with 1 to 3 $C_{1-6}$ alkyl groups; a benzothiazolylthio group; a benzothiazolylthio group substituted with 1 to 3 halogen atoms; a group represented by the formula: —Y—$(CR^{61}R^{62})_m$—$(CR^{63}R^{64})_n$—$R^7$—[wherein Y represents an oxygen or sulfur atom; $R^{61}$, $R^{62}$, $R^{63}$, and $R^{64}$ are identical or different and represent a hydrogen atom, a halogen atom, a $C_{1-4}$ alkyl group, or a trifluoromethyl group; $R^7$ represents a hydrogen atom; a halogen atom; a $C_{1-14}$ alkyl group; a $C_{3-8}$ cycloalkyl group; a $C_{3-8}$ cycloalkoxy group; a $C_{2-10}$ alkenyl group; a $C_{2-6}$ alkynyl group; a phenyl group; a phenyl group substituted with 1 to 3 substituents selected from the group consisting of nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms; a cyano group; a carboxyl group; a $C_{1-6}$ alkoxy group; a $C_{1-6}$ hydroxyalkyl group; a $C_{1-6}$ alkoxy $C_{1-6}$ alkoxy group; a $C_{1-6}$ alkoxy $C_{1-6}$ alkoxy $C_{1-6}$ alkoxy group; a $C_{1-6}$ alkylthiogroup; a $C_{2-6}$ alkanoyloxy group; a $C_{2-6}$ alkanoyloxy $C_{1-6}$ alkyl group; a phenoxy group; a phenylthio group; an N—($C_{1-6}$ alkyl) toluidino group; a pyrrolidino group; a piperidino group; a morpholino group; a pyridyl group; a pyridyl group substituted with a $C_{1-6}$ alkyl group; a piperidino group substituted with a $C_{1-6}$ alkyl group; a pyridyl group substituted with a $C_{1-6}$ alkoxy group; a pyrrolidino group substituted with a $C_{1-6}$ alkyl group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperadinyl group; a piperadin-1-yl group substituted with a $C_{1-6}$ alkyl group at the 4-position; a homopiperidinyl group; a homopiperidinyl group substituted with a $C_{1-6}$ alkyl group; a pyridylthio group; a quinolyl group; a furyl group; an oxetanyl group; an oxolanyl group; a dioxolanyl group; a dioxolanyl group substituted with a $C_{1-6}$ alkyl group; an oxanyl group; a dioxanyl group; a dioxanyl group substituted with a $C_{1-6}$ alkyl group; a benzodioxanyl group; a pyrrolidon-1-yl group; a pyrrolidinyl group; an N—($C_{1-6}$ alkyl) pyrrolidinyl group; a piperidinyl group; an N—($C_{1-6}$ alkyl) piperidinyl group; a pyrrolyl group; a thieyl group; a thiazolyl group; a thiazolyl group substituted with 1 to 3$C_{1-6}$ alkyl groups; a 2,6-purindion-7-yl group substituted with $C_{1-6}$ alkyl group(s); a furfuryl group; a di($C_{1-6}$ alkyl)amino group; a $C_{2-6}$ alkoxycarbonyl group; or a di($C_{1-6}$ alkyl)amino $C_{1-6}$ alkoxy group; m is an integer of 1 to 6; and n is an integer of 0 to 6]; or a group represented by the formula: —SO$_2$NR$^8$R$^9$ [wherein R$^8$ and R$^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively, taken together with the nitrogen atom to which they are bonded, form a 3,5-dioxopiperadino group, a pyrrolidinyl group, a piperidino group, or a morpholino group], or alternatively, the two groups adjacent to each other of R$^1$ to R$^5$, taken together with the benzene ring to which they are bonded, form a phthalimide ring; a phthalimide ring substituted with a $C_{1-6}$ alkyl group; an indole ring; an indane ring; an indazole ring; a benzotriazole ring; an S,S-dioxobenzothiophene ring; a 2,3-dihydroimidazo[2,1-b]benzothiazole ring; a dibenzofuran ring; a dibenzofuran ring substituted with a $C_{1-6}$ alkoxy group; a fluorene ring; a fluorene ring substituted with a halogen atom; a pyrene ring; a carbostyryl ring; a carbostyryl ring substituted with a $C_{1-6}$ alkyl group; a naphthalene ring; a naphthalene ring substituted with 1 to 3 substituents selected from the group consisting of cyano groups, halogen atoms, nitro groups, and $C_{1-6}$ alkyl groups; a 1,2,3,4-tetrahydronaphthalene ring; a quinoline ring; a quinoline ring substituted with a $C_{1-6}$ alkyl group; an isoquinoline ring; a 2-oxo-α-chromene ring; a 2-oxo-α-chromene ring substituted with 1 to 3 substituents selected from the group consisting of $C_{1-6}$ alkyl groups, $C_{1-6}$ alkoxy groups, and $C_{1-6}$ alkoxy $C_{1-6}$ alkyl groups; a cinnolin ring; a cinnolin ring substituted with a $C_{1-6}$ alkyl group; a phthalazindione ring; a benzothiazol ring; a benzothiazol ring substituted with a $C_{1-6}$ alkyl group; a benzodioxorane ring; or a benzobutyrolactone ring] or a pharmaceutically-acceptable salt thereof.

In the general formula (1) described above, it is preferable that R$^1$ to R$^5$ be identical or different and represent a hydrogen atom; a hydroxyl group; a carboxyl group; a halogen atom; a $C_{1-14}$ alkyl group; a $C_{1-14}$ alkyl group substituted with 1 to 6 halogen atoms; a $C_{2-6}$ alkynyl group;a $C_{3-8}$ cycloalkyl group; a $C_{3-8}$ cycloalkoxy group; a $C_{2-10}$ alkanoyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkyl group; a di($C_{1-6}$ alkyl)amino $C_{2-6}$ alkoxycarbonyl group; a mono- or di($C_{1-6}$ alkyl)amino group; a $C_{2-10}$ alkanoylamino group; a $C_{2-6}$ alkanoylamino group substituted with a $C_{1-6}$ alkyl group; a benzoylamino group; a carbamoyl group; a carbamoyl group mono- or di-substituted with $C_{1-6}$ alkyl or phenyl groups; an N—(N',N'-di($C_{1-6}$ alkyl) amino $C_{1-6}$ alkyl) carbamoyl group; a cyano group; a cyano $C_{1-6}$ alkyl group; a nitro group; a thiol group; a phenoxy group; a phenoxy group substituted with 1 to 3 substituents selected from the group consisting of $C_{1-6}$ alkyl groups, $C_{1-6}$ alkoxy groups, and halogen atoms; a phenylthio group; a nitrophenylthio group; a $C_{1-6}$ alkylsulfonyl group; a phenylsulfonyl group; a $C_{1-6}$ alkylthio $C_{1-6}$ alkyl group; a phenylsulfonyl $C_{1-6}$ alkylthio group wherein the benzene ring is substituted with 1 to 5 halogen atoms; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an α-cyanobenzyl group; an α-cyanobenzyl group substituted with 1 to 5 halogen atoms; a benzyl group substituted with a bicyclo[2.2.1]-hept-5-en-2,3-dicarboxyimidyl group; a benzoyl group; a styryl group; a styryl group substituted with 1 to 5 substituents selected from the group consisting of $C_{1-6}$ alkoxy groups and di($C_{1-6}$ alkyl) amino alkyl groups; a pyrrolidino group; a piperidino group; a morpholino group; a pyridyl group; a pyrimidinyl group; a pyrimidinyl group substituted with 1 to 3 substituents selected from the group consisting of $C_{1-6}$ alkyl groups and $C_{1-6}$ alkoxy groups; a phthalimidoyl group; a phthalimidoyl group substituted with 1 to 3 halogen atoms; an N-carbazolyl group; a dioxopiperidinyl group substituted with 1 to 3 $C_{1-6}$ alkyl groups; a phenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from the group consisting of halogen atoms, $C_{1-6}$ alkyl groups, and $C_{1-6}$ alkoxygroups; apyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of halogen atoms, $C_{1-6}$ alkyl groups, and $C_{2-6}$ alkoxycarbonyl groups; a thienopyrimidinylthio group; a thienopyrimidinylthio group substituted with 1 to 3 $C_{1-6}$ alkyl groups; a thienopyridylthio group; a thienopyridylthio group substituted with 1 to 3 $C_{1-6}$ alkyl groups; a benzothiazolylthio group; a benzothiazolylthio group substituted with 1 to 3 halogen atoms; a group represented by the formula: —Y—(CR$^{61}$R$^{62}$)$_m$—(CR$^{63}$R$^{64}$)$_n$—R$^7$ [wherein Y represents an oxygen or sulfur atom; R$^{61}$, R$^{62}$, R$^{63}$, and R$^{64}$ are identical or different and represent a hydrogen atom, a halogen atom, a $C_{1-4}$ alkyl group, or a trifluoromethyl group; R$^7$ represents a hydrogen atom; a halogen atom; a $C_{1-14}$ alkyl group; a $C_{3-8}$ cycloalkyl group; a $C_{2-10}$ alkenyl group; a $C_{2-6}$ alkynyl group; a phenyl group;

a phenyl group substituted with 1 to 3 substituents selected from the group consisting of nitro groups, cyano groups, $C_{1-6}$ alkyl groups, $C_{1-6}$ alkoxy groups, $C_{1-6}$ alkylthio groups, phenyl groups, phenoxygroups, phenethyl groups, $C_{2-6}$ alkoxycarbonyl groups, and halogen atoms; a cyano group; a carboxyl group; a $C_{1-6}$ alkoxy group; a $C_{1-6}$ hydroxyalkyl group; a $C_{3-8}$ cycloalkoxy group; a $C_{1-6}$ alkoxy $C_{1-6}$ alkoxy group; a $C_{1-6}$ alkoxy $C_{1-6}$ alkoxy $C_{1-6}$ alkoxy group; a $C_{1-6}$ alkylthio group; a $C_{2-6}$ alkanoyloxy group; a $C_{2-6}$ alkanoyloxy $C_{1-6}$ alkyl group; a phenoxy group; a phenylthio group; an N—($C_{1-6}$ alkyl)toluidino group; a pyrrolidino group; a piperidino group; a morpholino group; a pyridyl group; a pyridyl group substituted with a $C_{1-6}$ alkyl group; a piperidino group substituted with a $C_{1-6}$ alkyl group; a pyridyl group substituted with a $C_{1-6}$ alkoxy group; a pyrrolidino group substituted with a $C_{1-6}$ alkyl group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperadinyl group; a piperadin-1-yl group substituted with a $C_{1-6}$ alkyl group at the 4-position; a homopiperidinyl group; a homopiperidinyl group substituted with a $C_{1-6}$ alkyl group; a pyridylthio group; a quinolyl group; a furyl group; an oxetanyl group; an oxolanyl group; a dioxolanyl group; a dioxolanyl group substituted with a $C_{1-6}$ alkyl group; an oxanyl group; a dioxanyl group; a dioxanyl group substituted with a $C_{1-6}$ alkyl group; a benzodioxanyl group; a pyrrolidon-1-yl group; a pyrrolidinyl group; an N—($C_{1-6}$ alkyl)pyrrolidinyl group; a piperidinyl group; an N—($C_{1-6}$ alkyl)piperidinyl group; a pyrrolyl group; a thienyl group; a thiazolyl group; a thiazolyl group substituted with 1 to 3 $C_{1-6}$ alkyl groups; a 2,6-purindion-7-yl group substituted with $C_{1-6}$ alkyl group(s); a furfuryl group; a di($C_{1-6}$ alkyl)amino group; a $C_{2-6}$ alkoxycarbonyl group; or a di($C_{1-6}$ alkyl)amino $C_{1-6}$ alkoxy group; m is an integer of 1 to 6; and n is an integer of 0 to 6].

In addition in the inhibitor of 20-hydroxyeicosatetraenoic acid synthase according to the present invention, it is preferable that in the compounds of the general formula (1), the compounds wherein $R^1$, $R^2$, $R^4$, and $R^5$ represent hydrogen atoms, or the pharmaceutically-acceptable salts thereof, be employed as effective ingredients.

In addition, the other mode of the present invention corresponds to hydroxyformamidine derivatives having a novel chemical structure in the compounds of the general formula (1) described above or a pharmaceutically-acceptable salt thereof.

That is, the other mode of the present invention corresponds to a hydroxyformamidine derivative represented by the general formula (2) as follows:

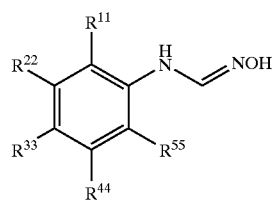

(2)

[wherein at least one of $R^{11}$ to $R^{55}$s represents a $C_{5-14}$ alkyl group; a $C_{2-6}$ alkenyl group; a $C_{3-8}$ cycloalkyl $C_{1-6}$ alkyl group; a $C_{2-6}$ alkynyl group; a $C_{3-8}$ cycloalkyl group; a $C_{3-8}$ cycloalkoxy group; a $C_{2-10}$ alkanoyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkyl group; a di($C_{1-6}$ alkyl)amino $C_{2-6}$ alkoxycarbonyl group; a mono- or di($C_{1-6}$ alkyl)amino group; a $C_{2-10}$ alkanoylamino group; a $C_{2-6}$ alkanoylamino group substituted with a $C_{1-6}$ alkyl group; a benzoylamino group; a carbamoyl group; a carbamoyl group mono- or di-substituted with $C_{1-6}$ alkyl or phenyl groups; an N—(N', N'-di($C_{1-6}$ alkyl)amino $C_{1-6}$ alkyl)carbamoyl group; a cyano group; a cyano $C_{1-6}$ alkyl group; a $C_{1-6}$ alkylsulfonyl group; a phenylsulfonyl group; a $C_{1-6}$ alkylthio $C_{1-6}$ alkyl group; a phenylsulfonyl $C_{1-6}$ alkylthio group wherein the benzene ring is substituted with 1 to 5 halogen atoms; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an αcyanobenzyl group; an α-cyanobenzyl group substituted with 1 to 5 halogen atoms; a benzyl group substituted with a bicyclo[2.2.1]-hept-5-en-2,3-dicarboxyimidyl group; a benzoyl group; a styryl group; a styryl group substituted with 1 to 5 substituents selected from the group consisting of $C_{1-6}$ alkoxy groups and di($C_{1-6}$ alkyl)aminoalkyl groups; a pyrrolidino group; a piperidino group; a morpholino group; a pyridyl group; a pyrimidinyl group; a pyrimidinyl group substituted with 1 to 3 substituents selected from the group consisting of $C_{1-6}$ alkyl groups and $C_{1-6}$ alkoxy groups; a phthalimiidoyl group; a phthalimidoyl group substituted with 1 to 3 halogen atoms; an N-carbazolyl group; a dioxopiperidinyl group substituted with 1 to 3 $C_{1-6}$ alkyl groups; aphenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from the group consisting of halogen atoms, $C_{1-6}$ alkyl groups, and $C_{1-6}$ alkoxy groups; a pyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of halogen atoms, $C_{1-6}$ alkyl groups, and $C_{2-6}$ alkoxycarbonyl groups; a thienopyrimidinylthio group; a thienopyrimidinylthio group substituted with 1 to 3 $C_{1-6}$ alkyl groups; a thienopyridylthio group; a thienopyridylthio group substituted with 1 to 3 $C_{1-6}$ alkyl groups; a benzothiazolylthio group; a benzothiazolylthio group substituted with 1 to 3 halogen atoms; a group represented by the formula: 13 Y—$(CR^{61}R^{62})_m$—$(CR^{63}R^{64})_n$—$R^{77}$ [wherein Y represents an oxygen or sulfur atom; $R^{61}$, $R^{62}$, $R^{63}$, and $R^{64}$ are identical or different and represent a hydrogen atom, a halogen atom, a $C_{1-4}$ alkyl group, or a trifluoromethyl group; $R^{77}$ represents a halogen atom; a $C_{4-14}$ alkyl group; a $C_{3-8}$ cycloalkyl group; a $C_{2-10}$ alkenyl group; a $C_{2-6}$ alkynyl group; a phenyl group; a phenyl group substituted with 1 to 3 substituents selected from the group consisting of nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms; a cyano group; a carboxyl group; a $C_{1-6}$ alkoxy group; a $C_{1-6}$ alkoxy $C_{1-6}$ alkoxy group; a $C_{1-6}$ alkoxy $C_{1-6}$ alkoxy $C_{1-6}$ alkoxy group; a $C_{1-6}$ hydroxyalkyl group; a $C_{3-8}$ cycloalkoxy group; a $C_{1-6}$ alkylthio group; a $C_{2-6}$ alkanoyloxy group; a $C_{2-6}$ alkanoyloxy $C_{1-6}$ alkyl group; a phenoxy group; a phenylthio group; an N—($C_{1-6}$ alkyl) toluidino group; a pyrrolidino group; a piperidino group; a morpholino group; a pyridyl group; a pyridyl group substituted with a $C_{1-6}$ alkyl group; a piperidino group substituted with a $C_{1-6}$ alkyl group; apyridyl group substituted with a $C_{1-6}$ alkoxy group; a pyrrolidino group substituted with a $C_{1-6}$ alkyl group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperadinyl group; a piperadin-1-yl group substituted with a $C_{1-6}$ alkyl group at the 4-position; a homopiperidinyl group; a homopiperidinyl group substituted with a $C_{1-6}$ alkyl group; a pyridylthio group; a quinolyl group; a furyl group; an oxetanyl group; an oxolanyl group; a dioxolanyl group; a dioxolanyl group substituted with a $C_{1-6}$ alkyl group; an oxanyl group; a dioxanyl group; a dioxanyl group substituted with a $C_{1-6}$ alkyl group; a benzodioxanyl group; a pyrrolidon-1-yl group; a pyrrolidinyl group; an N—($C_{1-6}$ alkyl)pyrrolidinyl group; a piperidinyl group; an N—($C_{1-6}$ alkyl)piperidinyl group; a pyrrolyl group; a thienyl group; a thiazolyl group; a thiazolyl group substituted with 1 to 3 $C_{1-6}$ alkyl groups; a 2,6-purindion-7-yl group substituted with $C_{1-6}$ alkyl group(s); a furfuryl group; a di($C_{1-6}$ alkyl)amino group; a $C_{1-6}$ alkoxycarbonyl group; or a di($C_{1-6}$ alkyl)amino $C_{1-6}$ alkoxy group; m is an integer of 1 to 6; and n is an integer of 0 to 6]; or a group represented by the formula: —$SO_2NR^8R^9$ [wherein $R^8$ and $R^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively, taken together with the nitrogen atom to which they are bonded, form a 3,5-dioxopiperadino group, a pyrrolidinyl group, a piperidino group, or a morpholino group], or alternatively, the two groups adjacent to each other of $R^{11}$ to $R^{55}$, taken together with the benzene ring to which they are bonded, form a phthalimide ring; a phthalimide ring substituted with a $C_{1-6}$ alkyl group; an indole ring; an indane ring; an indazole ring; a benzotriazole ring; an S,S-dioxobenzothiophene ring; a 2,3-dihydroimidazo[2,1-b] benzothiazole ring; a dibenzofuran ring; a dibenzofuran ring substituted with a $C_{1-6}$ alkoxy group; a fluorene ring; a fluorene ring substituted with a halogen atom; a pyrene ring; a carbostyryl ring; a carbostyryl ring substituted with a $C_{1-6}$ alkyl group; a naphthalene ring; a naphthalene ring substituted with 1 to 3 substituents selected from the group consisting of cyano groups, halogen atoms, nitro groups, and $C_{1-6}$ alkyl groups; a 1,2,3,4-tetrahydronaphthalene ring; a quinoline ring; a quinoline ring substituted with a $C_{1-6}$ alkyl group; an isoquinoline ring; a 2-oxo-α-chromene ring; a 2-oxo-α-chromene ring substituted with 1 to 3 substituents selected from the group consisting of $C_{1-6}$ alkyl groups, $C_{1-6}$ alkoxy groups, and $C_{1-6}$ alkoxy $C_{1-6}$ alkyl groups; a cinnolin ring; a cinnolin ring substituted with a $C_{1-6}$ alkyl group; a phthalazindione ring; a benzothiazol ring; a benzothiazol ring substituted with a $C_{1-6}$ alkyl group; a benzodioxorane ring; or a benzobutyrolactone ring, and the remaining groups of $R^{11}$ to $R^{55}$ are identical or different and represent a hydrogen atom, a $C_{1-4}$ alkyl group, a $C_{1-4}$ alkoxy group, a trifluoromethyl group, a nitro group, or a halogen atom] or a pharmaceutically-acceptable salt thereof.

In the compounds of the general formula (2), at least one of $R^{11}$ to $R^{55}$ may represent a $C_{5-14}$ alkyl group; a $C_{2-6}$ alkynyl group; a $C_{3-8}$ cycloalkyl group; a $C_{3-8}$ cycloalkoxy group; a $C_{2-10}$ alkanoyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkyl group, a di($C_{1-6}$ alkyl)amino $C_{2-6}$ alkoxycarbonyl group; amono- or di($C_{1-6}$ alkyl)amino group; a $C_{2-10}$ alkanoylamino group; a $C_{2-6}$ alkanoylamino group substituted with a $C_{1-6}$ alkyl group; a benzoylamino group; a carbamoyl group; a carbamoyl group mono- or di-substituted with $C_{1-6}$ alkyl or phenyl groups; an N-(N', N'-di($C_{1-6}$ alkyl)amino $_{1-6}$ alkyl) carbamoyl group; a cyano group; a cyano $C_{1-6}$ alkyl group; a $C_{1-6}$ alkylsulfonyl group; a phenylsulfonyl group; a $C_{1-6}$ alkylthio $C_{1-6}$ alkyl group; a phenylsulfonyl $C_{1-6}$ alkylthio group wherein the benzene ring in the phenylsulfonyl is substituted with 1 to 5 halogen atoms; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an α-cyanobenzyl group; an α-cyanobenzyl group substituted with 1 to 5 halogen atoms; a benzyl group substituted with a bicyclo[2.2.1]-hept-5-en-2,3-dicarboxyimidyl group; a benzoyl group; a styryl group; a styryl group substituted with 1 to 5 substituents selected from the group consisting of $C_{1-6}$ alkoxy groups and di($C_{1-6}$ alkyl)amino alkyl groups, a pyrrolidino group; a piperidino group; a morpholino group; a pyridyl group; a pyrimidinyl group; a pyrimidinyl group substituted with 1 to 3 substituents selected from the group consisting of $C_{1-6}$ alkyl groups and $C_{1-6}$ alkoxy groups; a phthalimidoyl group; a phthalimidoyl group substituted with 1 to 3 halogen atoms; an N-carbazolyl group; a dioxopiperidinyl group substituted with 1 to 3 $C_{1-6}$ alkyl groups; a phenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from the group consisting of halogen atoms, $C_{1-6}$ alkyl groups, and $C_{1-6}$ alkoxy groups; a pyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of halogen atoms, $C_{1-6}$ alkyl groups, and $C_{2-6}$ alkoxycarbonyl groups; halogen atoms, $C_{1-6}$ alkyl groups, and $C_{2-6}$ alkoxycarbonyl groups; a thienopyrimidinylthio group; a thienopyrimidinylthio group substituted with 1 to 3 $C_{1-6}$ alkyl groups; a thienopyridylthio group; a thienopyridylthio group substituted with 1 to 3 $C_{1-6}$ alkyl groups; a benzothiazolylthio group; a benzothiazolylthio group substituted with 1 to 3 halogen atoms; or a group represented by the formula: —$SO_2NR^8R^9$ [wherein $R^8$ and $R^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively $R^8$ and $R^9$, taken together with the nitrogen atom to which they are bonded, form a 3,5-dioxopiperadino group, a pyrrolidinyl group, a piperidino group, or a morpholino group], or alternatively, The two groups adjacent to each other of $R^{11}$ to $R^{55}$, taken together with the benzene ring to which they are bonded, may form a phthalimide ring; a phthalimide ring substituted with a $C_{1-6}$ alkyl group; an indole ring; an indane ring; an indazole ring; a benzotriazole ring; an S,S-dioxobenzothiophene ring; a 2,3-dihydroimidazo[2,1-b] benzothiazole ring; a dibenzofuran ring; a dibenzofuran ring substituted with a $C_{1-6}$ alkoxy group; a fluorene ring; a fluorene ring substituted with a halogen atom; a pyrene ring; a carbostyryl ring; a carbostyryl ring substituted with a $C_{1-6}$ alkyl group; a naphthalene ring; a naphthalene ring substituted with 1 to 3 substituents selected from the group consisting of cyano groups, halogen atoms, nitro groups, and $C_{1-6}$ alkyl groups; a 1,2,3,4-tetrahydronaphthalene ring; a quinoline ring; a quinoline ring substituted with a $C_{1-6}$ alkyl group; an isoquinoline ring; a 2-oxo -α-chromene ring; a 2-oxo-α-chromene ring substituted with 1 to 3 substituents selected from the group consisting of $C_{1-6}$ alkyl groups, $C_{1-6}$ alkoxy groups, and $C_{1-6}$ alkoxy $C_{1-6}$ alkyl groups; a cinnolin ring; a cinnolin ring substituted with a $C_{1-6}$ alkyl group; a phthalazindione ring; a benzothiazol ring; a benzothiazol ring substituted with a $C_{1-6}$ alkyl group; a benzodioxorane ring; or a benzobutyrolactone ring, and the remaining groups of $R^{11}$ to $R^{55}$ may be identical or different and represent a hydrogen atom, a $C_{1-4}$ alkyl group, a $C_{1-4}$ alkoxy group, a trifluoromethyl group, a nitro group, or a halogen atom.

In this case, it is preferable that at least one of $R^{11}$ to $R^{55}$ represent a $C_{5-14}$ alkyl group; a $C_{2-6}$ alkynyl group; a $C_{3-8}$ cycloalkyl group; a C3-8 cycloalkoxy group; a $C_{2-10}$ alkanoyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkyl group; a di($C_{1-6}$ alkyl)amino $C_{2-6}$ alkoxycarbonyl group; a mono- or di($C_{1-6}$ alkyl)amino group; a $C_{2-10}$ alkanoylamino group; a $C_{2-6}$ alkanoylamino group substituted with a $C_{1-6}$ alkyl group; a carbamoyl group; a carbamoyl mono- or di-substituted with $C_{1-6}$ alkyl or phenyl groups; an N—(N',N'-di($C_{1-6}$ alkyl) amino $C_{1-6}$ alkyl)carbamoyl group; a cyano group; a cyano $C_{1-6}$ alkyl group; a $C_{1-6}$ alkylsulfonyl group; a phenylsulfonyl group; a $C_{1-6}$ alkylthio $C_{1-6}$ alkyl group; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an α-cyanobenzyl group; an α-cyanobenzyl group substituted with 1 to 5 halogen atoms; a benzoyl group; a pyrrolidino group; a piperidino group; a morpholino group; a pyridyl group; a pyrimidinyl group; a pyrimidinyl group substituted with 1 to 3 substituents selected from the group consisting of $C_{1-6}$ alkyl groups and $C_{1-6}$ alkoxy groups; a pyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of go halogen atoms, $C_{1-6}$ alkyl groups, and $C_{2-6}$ alkoxycarbonyl groups; or a group represented by the formula: —SO$_2$NR$^8$R$^9$ [wherein R$^8$ and R$^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively $R^8$ and $R^9$, taken together with the nitrogen atom to which they are bonded, form a 3,5-dioxopiperadino group, apyrrolidinyl group, a piperidino group, or a morpholino group]
and the remaining groups of $R^{11}$ to $R^{55}$ be identical or different and represent a hydrogen atom, a $C_{1-4}$ alkyl group, a $C_{1-4}$ alkoxy group, a trifluoromethyl group, a nitro group, or a halogen atom.

On the other hand, in the compounds of the general formula (2), at least one of $R^{11}$ to $R^{55}$ may represent a group represented by the formula: —Y—(CR$^{61}$R$^{62}$)$_m$—(CR$^{63}$R$^{64}$)$_n$—R$^{77}$ [wherein Y represents an oxygen or sulfur atom; R$^{61}$, R$^{62}$, R$^{63}$, and R$^{64}$ are identical or different and represent a hydrogen atom, a halogen atom, a $C_{1-4}$ alkyl group, or a trifluoromethyl group; R$^{77}$ represents a halogen atom; a $C_{4-14}$ alkyl group; a $C_{3-8}$ cycloalkyl group; a $C_{2-10}$ alkenyl group; a $C_{2-6}$ alkynyl group; a phenyl group; a phenyl group substituted with 1 to 3 substituents selected from the group consisting of nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms; a cyano group; a carboxyl group; a $C_{1-6}$ alkoxy group; a $C_{1-6}$ hydroxyalkyl group; a $C_{3-8}$ cycloalkoxy group; a $C_{1-6}$ alkoxy $C_{1-6}$ alkoxy group; a $C_{1-6}$ alkoxy $C_{1-6}$ alkoxy $C_{1-6}$ alkoxy group; a $C_{1-6}$ alkylthio group; a $C_{2-6}$ alkanoyloxy group; a $C_{2-6}$ alkanoyloxy $C_{1-6}$ alkyl group; a phenoxy group; a phenylthio group; an N—($C_{1-6}$ alkyl) toluidino group; a pyrrolidino group; a piperidino group; a morpholino group; a pyridyl group; a pyridyl group substituted with a $C_{1-6}$ alkyl group; a piperidino group substituted with a $C_{1-6}$ alkyl group; apyridyl group substituted with a $C_{1-6}$ alkoxy group; a pyrrolidino group substituted with a $C_{1-6}$ alkyl group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperadinyl group; a piperadin-1-yl group substituted with a $C_{1-6}$ alkyl group at the 4-position; a homopiperidinyl group; a homopiperidinyl group substituted with a $C_{1-6}$ alkyl group; a pyridylthio group; a quinolyl group; a furyl group; an oxetanyl group; an oxolanyl group; a dioxolanyl group; a dioxolanyl group substituted with a $C_{1-6}$ alkyl group; an oxanyl group; a dioxanyl group; a dioxanyl group substituted with a $C_{1-6}$ alkyl group; a benzodioxanyl group; a pyrrolidon-1-yl group; a pyrrolidinyl group; an N—($C_{1-6}$ alkyl)pyrrolidinyl group; a piperidinyl group; an N—($C_{1-6}$ alkyl)piperidinyl group; a pyrrolyl group; a thienyl group; a thiazolyl group; a thiazolyl group substituted with 1 to 3 $C_{1-6}$ alkyl groups; a 2,6-purindion-7-yl group substituted with $C_{1-6}$ alkyl group(s); a furfuryl group; a di($C_{1-6}$ alkyl)amino group; a $C_{2-6}$ alkoxycarbonyl group; or a di($C_{1-6}$ alkyl)amino $C_{1-6}$ alkoxy group; m is an integer of 1 to 6; and n is an integer of 0 to 6], and the remaining groups of $R^{11}$ to $R^{55}$ may be identical or different and represent a hydrogen atom, a $C_{1-4}$ alkyl group, a $C_{1-4}$ alkoxy group, a trifluoromethyl group, a nitro group, or a halogen atom.

In this case, it is preferable that at least one of $R^{11}$ to $R^{55}$ represent a group represented by the formula: —O—$(CR^{61}R^{62})_m$—$(CR^{63}R^{64})_n$—$R^{77}$ [wherein $R^{61}$, $R^{62}$, $R^{63}$, and $R^{64}$ are identical or different and represent a hydrogen atom, a halogen atom, a $C_{1-4}$ alkyl group, or a trifluoromethyl group; $R^{77}$ represents a di($C_{1-6}$ alkyl)amino group; a di($C_{1-6}$ alkyl)amino $C_{1-6}$ alkoxy group; a piperidyl group; a piperidinyl group substituted with a $C_{1-6}$ alkyl group; a piperidino group; a piperidino group substituted with a $C_{1-6}$ alkyl group; a pyridyl group; a pyridinyl group substituted with a $C_{1-6}$ alkyl group; a pyridinyl group substituted with a $C_{1-6}$ alkoxy group; a pyridylthio group; a pyrrolidino group; a pyrrolidino group substituted with a $C_{1-6}$ alkyl group; a pyrrolidon-1-yl group; a pyrrolidinyl group; a pyrrolidinyl group substituted with a $C_{1-6}$ alkyl group; a pyrrolyl group; a thienyl group; a thiazolyl group; a morpholino group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperadinyl group; a piperadin-1-yl group substituted with a $C_{1-6}$ alkyl group at the 4-position; a homopiperidinyl group; or a homopiperidinyl group substituted with a $C_{1-6}$ alkyl group; m is an integer of 1 to 6; and n is an integer of 0 to 6], and the remaining groups of $R^{11}$ to $R^{55}$ are identical or different and represent a hydrogen atom, a $C_{1-6}$ alkyl group, a $C_{1-4}$ alkoxy group, a trifluoromethyl group, a nitro group, or a halogen atom.

In addition, in the compounds of the general formula (2), the compounds wherein $R^{11}$, $R^{22}$, $R^{44}$, and $R^{55}$ represent a hydrogen atom, that is, only $R^{33}$ at the para position of the hydroxyformamidino group on the benzene ring is a non-hydrogen atom substituent, are preferred.

It was discovered by the present inventors that the compounds of the general formulae (1) and (2) described above exhibit an inhibiting activity of 20-HETE synthase. Therefore, these compounds are useful as therapeutic agents for kidney diseases, cerebrovascular diseases, or circulatory diseases.

The terms used in the present invention are defined in the following. In the present invention, "$C_{x-y}$" means that the group following the "$C_{x-y}$" has the number of x-y of carbon atoms.

The term "halogen atom" refers to a fluorine, chlorine, bromine, or iodine atom.

The term "$C_{1-4}$, $C_{1-6}$, $C_{1-8}$, and $C_{1-14}$ alkyl group" means straight-chain or branched alkyl groups having 1 to 4, 1 to 6, 1 to 8, and 1 to 14 carbon atoms, respectively. For example, as a $C_{1-14}$ alkyl group, mention may be made of a methyl group, an ethyl group, a propyl group, an isopropyl group, a butyl group, an isobutyl group, a tert-butyl group, a pentyl group, an isopentyl group, a hexyl group, an isohexyl group, a heptyl group, an octyl group, a nonyl group, or a decyl group, or the like.

The term "$C_{1-14}$ alkyl group substituted with 1 to 6 halogen atoms" means a straight-chain or branched alkyl group having 1 to 14 carbon atoms, substituted with 1 to 6 halogen atoms. A methyl or ethyl group substituted with 1 to 4 halogen atoms is preferred. As an example thereof, mention may be made of a difluoromethyl group, a dibromomethyl group, a trifluoromethyl group, or a trifluoroethyl group, or the like. Among these groups, a trifluoromethyl group is preferable.

The term "$C_{2-6}$ alkenyl" means a straight-chain or branched alkenyl group having a double bond, and 2 to 6 carbon atoms. As an example thereof, mention may be made of an ethenyl group, a propenyl group, or a butenyl group, or the like.

The term "$C_{2-6}$ alkynyl group" means a straight-chain or branched alkynyl group having a triple bond, and 2 to 6 carbon atoms. As an example thereof, mention may be made of an ethynyl group, a propynyl group, or a butynyl group, or the like.

The term "$C_{3-8}$ cycloalkyl group" means a cyclic alkyl group having 3 to 8 carbon atoms, including, for example, a cyclopropyl group, a cyclopentyl group, or a cyclohexyl group, or the like.

The term "$C_{3-8}$ cycloalkyl $C_{1-6}$ alkyl group" means a group having a combined structure of a $C_{3-8}$ cycloalkyl group and a $C_{1-6}$ alkyl group, including, for example, a cyclopropylmethyl group, a cyclobutylmethyl group, a cyclopentylmethyl group, or a cyclohexylmethyl group, or the like.

The term "$C_{1-6}$ alkoxy group" means a straight-chain or branched alkoxy group having 1 to 6 carbon atoms. As an example thereof, mention may be made of a methoxy group, an ethoxy group, a propoxy group, an isopropoxy group, a 2,2-dimethylpropoxy group, a butoxy group, a tert-butoxy group, a 3-methylbutoxy group, a 3,3-dimethylbutoxy group, a 3-methylpentoxy group, or a 4-methylpentoxy group, or the like.

The term "$C_{1-6}$ alkoxy $C_{1-6}$ alkyl group" means a group having a combined structure of a $C_{1-6}$ alkoxy group and a $C_{1-6}$ alkyl group. As an example thereof, mention maybe made of a methoxymethyl group, an ethoxymethyl group, a methoxyethyl group, an ethoxyethyl group, a propoxyethyl group, an isopropoxyethyl group, a butoxyethyl group, or a tert-butoxyethyl group, or the like.

The term "$C_{3-8}$ cycloalkoxy group" means a cycic alkoxy group having 3 to 8 carbon atoms, including, for example, a cyclopropyloxy group, a cyclopentyloxy group, or a cyclohexyloxy group, or the like.

The term "$C_{2-10}$ alkanoyl group" means a straight-chain or branched alkanoyl group having 2 to 10 carbon atoms. As an example thereof, mention may be made of an acetyl group, a propionyl group, a butyryl group, an isobutylyl group, or a valeryl group, or the like. Among these groups, an acetyl group is preferable.

The term "$C_{1-6}$ hydroxyalkyl" means a $C_{1-6}$ alkyl group substituted with hydroxyl group(s). As an example thereof, mention may be made of a hydroxymethyl group, a 1-hydroxyethyl group, a 2-hydroxyethyl group, a 3-hydroxypropyl group, a 2,3-dihydroxyethyl group, or the like. Among these groups, a hydroxymethyl group, a 1-hydroxyethyl group, a 2-hydroxyethyl group, or a 3-hydroxypropyl group is in particular, preferable.

The term "$C_{2-6}$ alkanoyloxy $C_{1-6}$ alkyl group" means a group wherein the hydroxyl group(s) of above $C_{1-6}$ hydroxyalkyl group is/are substituted with $C_{2-6}$ alkanoyloxy group(s), including, for example, a 2,3-diacetoxyethyl group. The term "$C_{1-6}$ hydroxyalkyl group substituted with 1 to 6 halogen atoms" means a $C_{1-6}$ hydroxyalkyl group substituted with 1 to 6 halogen atoms. As an example thereof, mention may be made of a hydroxyfluoromethyl group, a 1-hydroxy-2-fluoroethyl group, a 2-hydroxy-2-fluoroethyl group, a 3-hydroxy-2-chloropropyl group, a 2,3- dihydroxy-3-bromopropyl group, a 1,1,1,3,3,3-hexafluoro-2-hydroxypropyl group, or the like. Among these groups, a 1,1,1,3,3,3-hexafluoro-2-hydroxypropyl group is preferable.

The term "$C_{2-6}$ alkoxycarbonyl group" means a group having a combined structure of a straight-chain or branched $C_{1-5}$ alkoxy group and a carbonyl group. As an example thereof, mention may be made of a methoxycarbonyl group, an ethoxycarbonyl group, a propoxycarbonyl group, an isopropoxycarbonyl group, or a butoxycarbonyl group, or the like, and among these groups, a methoxycarbonyl group or a propoxycarbonyl group is preferable.

The term "$C_{2-6}$ alkoxycarbonyl $C_{1-6}$ alkyl group" means a group having a combined structure of a $C_{2-6}$ alkoxycarbonyl group and a $C_{1-6}$ alkyl group. Therefore, a $C_{2-6}$ alkoxycarbonyl $C_{1-6}$ alkyl group may be represented by the general formula: —(CH$_2$)$_k$—COOR$^{14}$ (wherein k is an integer of 1 to 6; R$^{14}$ is a $C_{1-6}$ alkyl group), including, for example, —CH$_2$COOCH$_3$ (a methoxycarbonylmethyl group), —CH$_2$COOCH$_2$CH$_3$ (an ethoxycarbonylmethyl group), —CH$_2$CH$_2$COOCH$_3$ (a methoxycarbonylethyl group), —CH$_2$CH$_2$COOCH$_2$CH$_3$ (an ethoxycarbonylethyl group), or the like. Among these groups, an ethoxycarbonylmethyl group is particularly preferable.

The term "di($_{1-6}$ alkyl)amino $C_{2-6}$ alkoxycarbonyl" means a group having a combined structure of an amino group substituted with two $C_{1-6}$ alkyl groups and a $C_{2-6}$ alkoxycarbonyl group. As an example thereof, mention may be made of an N,N-diethylaminoethoxycarbonyl group, or an N,N-dibutylaminopropoxycarbonyl group, or the like. In particular, an N,N-diethylaminoethoxycarbonyl group is preferable.

The term "mono- or di($C_{1-6}$ alkyl)amino group" means an amino group substituted with one or two $C_{1-6}$ alkyl groups. As an example thereof, mention may be made of a methylamino group, an ethylamino group, a dimethylamino group, or a diethylamino group, or the like. Among these groups, a dimethylamino group is preferable.

The term "$C_{2-10}$ alkanoylamino group" means an amino group substituted with a $C_{2-10}$ alkanoyl group, and as an example thereof, an acetylamino group may be given. In addition, as an example of "$C_{2-10}$ alkanoylamino group substituted with $C_{1-6}$ alkyl", mention may be made of an N-acetyl-N-methylamino group.

As an example of "carbamoyl group mono- or di-substituted with $C_{1-6}$ alkyl or phenyl groups", mention may be made of an N-methylcarbamoyl group, a N-butylcarbamoyl group, or an N-phenylcarbamoyl group. As an example of "N—(N',N'-di($C_{1-6}$ alkyl)amino $C_{1-6}$ alkyl)carbamoyl group", mention may be made of an N—(N',N'-diethylaminoethyl)carbamoyl group.

The term "cyano $C_{1-6}$ alkyl group" means a group having a combined structure of a cyano group and a $C_{1-6}$ alkyl group. As an example thereof, mention may be made of a cyanomethyl group, a cyanoethyl group, or a cyanopropyl group. Among these groups, a cyanomethyl group is particularly preferable.

As an example of "phenoxy group substituted with 1 to 3 substituents selected from the group consisting of nitro groups, thiol groups, phenoxy groups, $C_{1-6}$ alkyl groups, $C_{1-6}$ alkoxy groups, and halogen atoms", mention may be made of a 2-methylphenoxy group, a 3-methylphenoxy group, a 4-methylphenoxy group, a 2-methoxyphenoxy group, a 3-methoxyphenoxy group, a 4-methoxyphenoxy group, a 2-chlorophenoxy group, a 3-chlorophenoxy group, or a 4-chlorophenoxy group, or the like. Among these groups, a 2-methylphenoxy group, a 4-methylphenoxy group, a 2-methoxyphenoxy group, a 4-methoxyphenoxy group, or a 4-chlorophenoxy group is preferable.

The term "$C_{1-6}$ alkylsulfonyl group" means a group having a combined structure of a $C_{1-6}$ alkyl group and a sulfonyl group (—SO$_2$—). As an example thereof, mention may be made of a methylsulfonyl group, an ethylsulfonyl group, a propylsulfonyl group, an isopropylsulfonyl group, a butylsulfonyl group, an isobutylsulfonyl group, a tert-butylsulfonyl group, a pentylsulfonyl group, or an isopentylsulfonyl group, or the like. A methylsulfonyl group is preferable.

The term "$C_{1-6}$ alkylthio $C_{1-6}$ alkyl group" means a group having a combined structure of a $C_{1-6}$ alkylthio group and a $C_{1-6}$ alkyl group. As an example thereof, a methylthiomethyl group, or a 2-methylthioethyl group, or the like may be given, and a methylthiomethy group is preferable.

The term "phenylsulfonyl $C_{1-6}$ alkylthio wherein the benzene ring is substituted with 1 to 5 halogen atoms" means a group having a combined structure of a substituted phenylsulfonyl group and a $C_{1-6}$ alkylthio group. As an example thereof, a 4 chhlorophenylsulfonylmethylthio group or the like may be given.

As an example of the "phenyl group substituted with 1 to 3 substituents selected from the group consisting of cyano groups, halogen atoms, $C_{1-6}$ alkyl groups, and $C_{1-6}$ alkoxy groups", mention may be made of a 4-cyanophenyl group, a 4-chlorophenyl group, a 4-methylphenyl group, or a 4-methoxyphenyl group, or the like. Among these groups, a 4-cyanophenyl group is preferable. As the "α-cyanobenzyl group substituted with 1 to 5 halogen atoms", for example, an α-cyano-4-chlorobenzyl group or the like may be given.

As an example of the "styryl group substituted with 1 to 5 substituents selected from the group consisting of $C_{1-6}$ alkoxy groups and di($C_{1-6}$ alkyl)amino alkyl groups", mention may be made of a 4-methoxystyryl group, or an 4-N,N-dimethylaminostyryl group, or the like.

As an example of the "pyrimidinyl group substituted with 1 to 3 substituents selected from the group consisting of $C_{1-6}$ alkyl groups and $C_{1-6}$ alkoxy groups", mention may be made of a 6-methoxypyrimidin-4-yl group, or a 2-methylpyrimidin-4-yl group, or the like.

As an example of the "phthalimidoyl group substituted with 1 to 3 halogen atoms", a 5-chloro-N-phthalimidoyl group or the like may be given.

As an example of the "dioxopiperidinyl group substituted with 1 to 3 $C_{1-6}$ alkyl groups", a 2,6-dioxo-3-ethylpiperidin-3-yl group or the like may be given.

As an example of the "phenylsulfonylamino group substituted with 1 to 3 $C_{1-6}$ alkyl groups", a 4-methylphenylsulfonylamino group or the like may be given. As an example of the "$C_{1-6}$ alkylaminosulfonyl $C_{1-6}$ alkyl group", a methylaminosulfonylmethyl group or the like may be given.

As an example of the "oxadiazolyl group substituted with substituted phenyl group wherein the substituents in the substituted phenyl group are 1 to 3 substituents selected from the group consisting of halogen atoms, $C_{1-6}$ alkyl groups, and $C_{1-6}$ alkoxy groups", mention maybe made of a group wherein an oxadiazole ring is substituted with a phenyl group substituted with a tert-butyl group, or a methoxy group, or a bromine atom. More particularly, a 5-(p-tert-butylphenyl)oxadiazolin-2-yl group, a 5-(m-methoxyphenyl)oxadiazolin-2-yl group, or a 5-(5-bromo-3-methoxyphenyl)oxadiazolin-2-yl group, or the like may be given.

As an example of "pyrazolyl group substituted with 1 to 3 substituents selected from the group consisting of halogen atoms, $C_{1-6}$ alkyl groups, and trifluoromethyl groups", a 3-trifluoromethylpyrazolyl group or the like may be given.

As an example of "furyl group substituted with 1 to 3 substituents selected from the group consisting of halogen atoms, $C_{1-6}$ alkyl groups, and $C_{2-6}$ alkoxycarbonyl groups", mention may be made of a furyl group substituted with a methyl group, or an ethoxycarbonyl group, or the like, and more particularly, a 5-methyl-4-ethoxycarbonyl-2-furyl group or the like.

As the "thienopyrimidinylthio group substituted with 1 to 3 $C_{1-6}$ alkyl groups", a substituted thienopyrimidinylthio group wherein the fused ring is substituted with one methyl or ethyl group is preferable, and more particularly, a group wherein a thiophene ring is substituted with a methyl group is more preferable.

As the "thienopyridylthio group substituted with 1 to 3 $C_{1-6}$ alkyl groups", a substituted thienopyridylthio group wherein the fused ring is substituted with one methyl or ethyl group is preferable, and more particularly, a group wherein a thiophene ring is substituted with a methyl group is more preferable.

As the "benzothiazolylthio group substituted with 1 to 3 halogen atoms", a benzothiazolylthio group wherein the fused ring is substituted with one halogen atom is preferable, and more particularly, a group wherein the benzene ring is substituted with a chlorine atom is more preferable.

As the "isoxazolyl group substituted with 1 to 3 $C_{1-6}$ alkyl groups", an isoxazolyl group substituted with one or two methyl or ethyl groups is preferable, and more particularly, a 5-methylisoxazoly-3-yl group is more preferable.

As the "thiazolyl group substituted with 1 to 3 $C_{1-6}$ alkyl groups", a thiazolyl group substituted with one or two methyl or ethyl groups is preferable.

As the "pyridyl group substituted with 1 to 3 $C_{1-6}$ alkyl groups", a pyridyl group substituted with one or two methyl or ethyl groups, and in particular, a 2-methylpyridin-6-yl group is preferable.

As the "pyrimidinyl group substituted with 1 to 3 $C_{1-6}$ alkyl groups", a pyrimidinyl group substituted with one or two methyl or ethyl groups is preferable, and more particularly, a 2,4-dimethylpyrimidin-6-yl group is more preferable.

As the "pyrimidinyl group substituted with 1 to 3 $C_{1-6}$ alkoxy groups", a pyrimidinyl group substituted with one or two methoxy or ethoxy groups is preferable, and more particularly, a 4-methoxypyrimidin-6-yl group, or a 2,4-dimethylpyrimidin-6-yl group is more preferable.

As the "pyridazinyl group substituted with 1 to 3 $C_{1-6}$ alkoxy groups", a pyridazinyl group substituted with one or two methoxy or ethoxy groups is preferable.

The term "$C_{2-10}$ alkenyl group" means a straight-chain or branched alkenyl group having a double bond, and 2 to 10 carbon atoms. As an example thereof, mention may be made of an ethenyl group, a propenyl group, or a butenyl group, or the like, and more particularly, a 1,5-dimethyl-4-hexenyl group, or the like.

The term "$C_{1-6}$ alkylthio group" means a straight-chain or branched alkylthio group having 1 to 6 carbon atoms. As an example thereof, mention may be made of a methylthio group, an ethylthio group, a propylthio group, an isopropylthio group, a butylthio group, an isobutylthio group, a tert-butylthio group, a pentylthio group, or an isopentylthio group, or the like, and a methylthio group is particularly preferable.

The term "$C_{2-6}$ alkanoyloxy group" means a group having a combined structure of a $C_{2-6}$ alkanoyl group and an oxy group (—O—). As an example thereof, mention may be made of an acetyloxy group, a propionyloxy group, a butyryloxy group, an isobutyryloxy group, or a valeryloxy group, or the like.

As an example of "phenyl group substituted with 1 to 3 substituents selected from the group consisting of nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms", mention may be made of a 4-chlorophenyl group, a 4-fluorophenyl group, a 2,5-difluorophenyl group, a 2,5-dichlorophenyl group, an o-phenethylphenyl group, a 4-methylthiophenyl group, a m-phenoxyphenyl group, a 4-methylphenyl group, a 3-methylphenyl group, a 2-methylphenyl group, a 2-methoxyphenyl group, a 3-methoxyphenyl group, a 4-methoxyphenyl group, a 2,3-dimethoxyphenyl group, a 2,4-dimethoxyphenyl group, a 4-methoxycarbonylphenyl group, a p-phenylphenyl group, or a m-cyanophenyl group, or the like.

The term "$C_{1-6}$ alkoxy $C_{1-6}$ alkoxy group" means a group having a combined structure of a $C_{1-6}$ alkoxy group and a $C_{1-6}$ alkoxy group. As an example thereof, mention may be made of a methoxymethoxy group, a methoxyethoxy group, an ethoxyethoxy group, or a methoxypropoxy group, or the like.

Examples of the "$C_{1-6}$ alkoxy $C_{1-6}$ alkoxy $C_{1-6}$ alkoxy group" include $CH_3OCH_2CH_2OCH_2CH_2O$— and the like.

Examples of the "di($C_{1-6}$ alkyl)amino group" include —N($CH_3$)2, —N($CH_2CH_3$)$_2$, —N($CH_2CH_2CH_3$)$_2$, and the like.

Examples of the "di($C_{1-6}$ alkyl)amino $C_{1-6}$ alkoxy group" include —OCH$_2$N(CH$_3$)$_2$, —OCH$_2$CH$_2$N (CH$_3$)2, —OCH$_2$CH$_2$N(CH$_2$CH$_3$)$_2$, and the like The term "N—($C_{1-6}$ alkyl) toluidino group" means a group having a structure wherein a toluidino group (CH$_3$—C$_6$H$_4$—NH—) is substituted with a $C_{1-6}$ alkyl group and preferably is substituted with a methyl or ethyl group. In particular, an N-ethyl-m-toluidino group is preferable.

The "furyl group" includes a 2-furyl or 3-furyl group.

The "oxetanyl group" has a structure of a saturated 4-membered ring having one oxygen atom as a hetero atom, and includes a 2-oxetanyl group, or a 3-oxetanyl group.

The "oxolanyl group" has a structure of a saturated 5-membered ring having one oxygen atom as a hetero atom, and includes a 2-oxolanyl group, or a 3-oxolanyl group.

The "dioxolanyl group" refers to a mono-valent group derived by eliminating hydrogen atom from a saturated 5-membered ring having two oxygen atoms as hetero atoms (dioxolane), preferably from a 1,3-dioxolane ring. In the dioxolanyl group, the ring thereof may be substituted with $C_{1-6}$ alkyl group(s). As an example thereof, a 2,2-dimethy-1,3-dioxolan-4-yl group or the like may be given.

The "oxanyl group" has a structure of a saturated 6-membered ring having one oxygen atom as a hetero atom, and includes a 2-oxanyl, a 3-oxanyl group, or a 4-oxanyl group.

The "dioxanyl group" refers to a mono-valent group derived by eliminating hydrogen atom from a saturated 6-membered ring having two oxygen atoms as hetero atoms (dioxane), preferably from a 1,3-dioxane ring. In the dioxanyl group, the ring thereof may be substituted with $C_{1-6}$ alkyl group(s). As an example thereof, a 5,5-dimethyl-1,3-dioxan-2-yl group or the like may be given.

The "benzodioxanyl group" refers to a mono-valent group derived by eliminating hydrogen atom from a benzodioxane ring, preferably a 1,4-benzodioxane ring. As an example thereof, a 1,4-benzodioxan-2-yl group or the like may be given.

The "piperidinyl group" includes a 2-piperidinyl, a 3-piperidinyl group, or a 4-piperidinyl group. In addition, in the piperidinyl group, the nitrogen atom present therein may be substituted with a $C_{1-6}$ alkyl group, and an N-methylpiperidinyl group is preferred.

The "piperidino group" refers to a mono-valent group derived by eliminating a hydrogen atom present on the nitrogen atom of piperidine.

The "pyridyl group" includes a 2-pyridyl group, 3-pyridyl group, or a 4-pyridyl group. In the pyridyl group, the ring thereof may be substituted with a $C_{1-6}$ alkyl group, preferably a methyl group. As an example thereof, a 6-methyl-2-pyridyl group may be given.

The "pyridylthio group" has a combined structure of a pyridyl group and one thio group, and includes a pyridin-2-ylthio group, a pyridin-3-ylthio,group, or a pyridin-4-ylthio group, and a pyridin-2-yl group is preferable.

The "pyrrolidino group" refers to a mono-valent group derived by eliminating a hydrogen atom present on the nitrogen atom of pyrrolidine.

The "pyrrolidon-1-yl group" includes a 2-pyrrolidon-1-yl or 3-pyrrolidon-1-yl group.

The "pyrrolidinyl group" includes a 2-pyrrolidinyl group or 3-pyrrolidinyl group. In the pyrrolidinyl group, the nitrogen atom present thereon may be substituted with a $C_{1-6}$ alkyl group. As an example thereof, an N-methyl-2-pyrrolidinyl group or the like may be given.

The "quinolyl" includes a 2-quinolyl group, a 3-quinolyl group, a 4-quinolyl group, a 5-quinolyl group, a 6-quinolyl group, a 7-quinolyl group, or a 8-quinolyl group, and a 2-quinolyl group is preferable.

The "pyrrolyl group" includes a 1-pyrrolyl group, a 2-pyrrolyl group, or a 3-pyrrolyl group, and a 1-pyrrolyl group (N-pyrrolyl group) is preferable.

The "thienyl group" includes a 2-thienyl group, or a 3-thienyl group.

The "thiazolyl group" includes a 2-thiazolyl group, a 4-thiazolyl group, or a 5-thiazolyl group. In addition, in the thiazolyl group, the ring thereof may be substituted with a $C_{1-6}$ alkyl group. As an example thereof, a 4-methyl-5-thiazolyl group or the like may be given.

The "morpholino group" refers to a mono-valent group derived by eliminating a hydrogen atom present on the nitrogen atom of morpholine.

The "furfuryl group" means a 2-furfuryl group.

The "2,6-purindion-7-yl group" refers to a mono-valent group derived from 2,6-purindione wherein oxo groups (=O) are bonded to the carbon atoms at the 2-position and the 6-position of the purine ring and a group derived by eliminating the hydrogen atom present on the nitrogen atom at the 7-position. For the "2,6-purindion-7-yl substituted with $C_{1-6}$ alkyl group(s)", it is preferable that one or two nitrogen atoms on the group be substituted with a $C_{1-6}$ alkyl group, and in particular, a methyl group. As an example thereof, a 1,3-dimethyl-2,6-purindion-7-yl group or the like may be given.

Any two groups of $R^1$ to $R^5$ adjacent to each other in the general formula (1), taken together with the benzene ring to which they are bonded, may form the ring structures described above. In these rings, the following rings may be specially mentioned.

As the "phthalimide ring substituted with a $C_{1-6}$ alkyl group", a ring substituted with a methyl or ethyl group is preferable, and more particularly, for example, a ring substituted with a methyl group such as an N-methylphthalimide ring is more preferable.

As the "dibenzofuran ring substituted with a $C_{1-6}$ alkoxy group", a ring substituted with a methoxy or ethoxy group is preferable, and particularly, a ring substituted with a methoxy group is more preferable.

As the "fluorene ring substituted with a halogen atom", a ring substituted with a chlorine or bromine atom is preferred, and furthermore, a ring substituted with a bromine atom is more preferable.

As the "carbostyryl ring substituted with a $C_{1-6}$ alkyl group", a ring substituted with a methyl or ethyl group is preferable and furthermore, a ring substituted with a methyl group is more preferable.

As the "naphthalene ring substituted with 1 to 3 substituents selected from the group consisting of cyano groups, halogen atoms, nitro groups, and $C_{1-6}$ alkyl groups", a ring substituted with 1 to 3 cyano groups, halogen atoms; nitro groups, methyl groups or ethyl groups is preferable, and particularly, a ring substituted with a cyano group, a bromine or chlorine atom, a nitro group or a methyl group is more preferable.

As the "quinoline ring substituted with a $C_{1-5}$ alkyl group", a ring substituted with a methyl or ethyl group is preferred, and in particular, a quinoline ring substituted with a methyl group is more preferable.

As the "2-oxo-α-chromene ring substituted with 1 to 3 substituents selected from the group consisting of $C_{1-6}$ alkyl groups, $C_{1-6}$ alkoxy groups, and $C_{1-6}$ alkoxy $C_{1-6}$ alkyl groups", a ring substituted with a methyl group, an ethyl group, a methoxy group, an ethoxy group, a methoxymethyl group, a methoxyethyl group, an ethoxymethyl group, or an ethoxyethyl group is preferred, and in particular, a ring substituted with a methyl or methoxy methyl group is more preferable.

As the "cinnolin ring substituted with a $C_{1-6}$ alkyl group", a ring substituted with a methyl or ethyl group is preferred, and in particular, a ring substituted with a methyl group is more preferable.

As the "benzothiazol ring substituted with a $C_{1-6}$ alkyl group", the ring substituted with a methyl or ethyl group is preferred and furthermore, a ring substituted with a methyl group is more preferable.

In addition, in the present invention, the term "pharmaceutically-acceptable salt" refers to a salt with an alkali metal, an alkali earth metal, ammonium, an alkylammonium, or the like, as well as, a salt with a mineral acid or an organic acid. As an example thereof, mention may be made of sodium salts, potassium salts, calcium salts, ammonium salts, aluminum salts, triethylammonium salts, acetates, propionates, butyrates, formates, trifluoroacetates, maleates, tartarates, citrates, stearates, succinates, ethylsuccinates, lactobionates, gluconates, glucoheptonates, benzoates, methanesulfonates, ethanesluefonates, 2-hydroxyethanesulfonates, benzenesulfonates, para-toluenesulfonates, laurylsulfates, malates, aspartates, glutamates, adipates, salts with cysteine, salts with N-acetylcysteines, hydrochlorides, hydrobromides, phosphates, sulfates, hydroiodides, nicotinates, oxalates, picrates, thiocyanates, undecanates, salts with polymeric acrylic acid, salts with carboxyvinyl polymers, or the like.

The compounds represented by the general formula (1) of the present invention may be prepared by or according to the methods described in Japanese Patent Application, Toku-Kai-Sho 61-165360 (which is incorporated herein by reference.)

For example, the compounds of the present invention may be synthesized by reacting aniline derivatives substituted with $R^1$ to $R^5$ described below

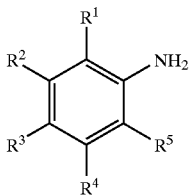

with orthoformates such as trimethyl orthoformate, triethyl orthoformate, or the like in the presence or absence of a catalytic amount of an organic acid such as acetic acid, a mineral acid such as hydrochloric acid, or a salt of a mineral acid and an amine such as pyridine hydrochloride, for 2 to 72 hours at a temperature preferably in the range of room temperature to 150° C., and more preferably in the range of 70 to 100° C. to obtain an intermediate, and subsequently treating the intermediate, after isolation or in the state as produced, with hydroxylamine in a solvent such as ethanol.

The aniline derivatives described above may be prepared, for example, by the following method. Herein, in order to simplify the explanation, the aniline derivatives wherein $R^1$, $R^2$, $R^4$, and $R^5$ are hydrogen atoms and $R^3$ is a group represented by the formula: $-Y-(CR^{61}R^{62})_m-(CR^{63}R^{64})_n-R^7$, are employed.

At first, a compound represented by the formula (a):

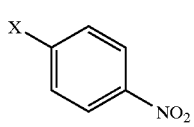

(wherein X represents a halogen atom) and a compound, for example, represented by the following formula (b):

$$R^7(CR^{63}R^{64})_n-(CR^{61}R^{62})_m YH \quad (b)$$

(wherein $R^7$, Y, $R^{61}$, $R^{62}$, m, $R^{63}$, $R^{64}$, and n have the same meanings as described above) are reacted in the presence of a base to obtain a compound represented by the following formula (c).

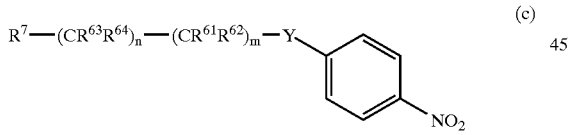

Subsequently, the compound represented by the formula (c) described above is derived to an aniline derivative represented by the following formula (d) by means of a general method for reducing an aromatic nitro group to an aromatic amino group.

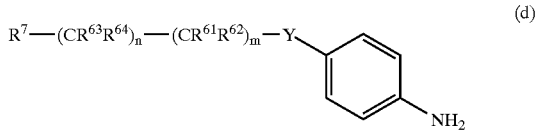

The inhibitors for production of 20-HETE according to the present invention comprise compounds represented by the general formula (1) or the pharmaceutically-acceptable salts thereof as active ingredients, and effectively inhibit the production of 20-HETE.

In addition, the inhibitors for production of 20-HETE of the present invention are useful as medicines, and in particular, therapeutic agents for kidney diseases, cerebrovascular diseases, or circulatory diseases.

The dose of the medicines (including therapeutic agents for kidney diseases, cerebrovascular diseases, or circulatory diseases), as well as the inhibitors for production of 20-HETE according to the present invention, is preferably in a range of 1 to 2000 mg per day as the compounds represented by the general formula (1) or the pharmaceutically-acceptable salts thereof, in the case of an adult human subject to be treated. They may be administered in a single dose or divided into several doses per day. The doses may vary depending on the usage, as well as, the age, weight, and conditions of each individual patient, and the like.

The medicines (therapeutic agents for kidney diseases, cerebrovascular diseases, or circulatory diseases) as well as, the inhibitors for production of 20-HETE according to the present invention may be administered orally or parenterally, in the form of tablets, capsules, granules, powders, troches, ointments, creams, emulsions, suspensions, suppositories, injectable solutions, or the like, each of which maybe produced according to the conventional formulation methods (for example, methods defined in the 12$^{th}$ revision of Japanese Pharmacopeia). These preparation forms may be selected depending on the conditions and ages of the patients, as well as the purpose of the treatment. Upon manufacturing preparations in various formulations, conventional fillers (for example, crystalline cellulose, starch, lactose, mannitol, or the like), binders (for example, hydroxypropylcellulose, polyvinylpyrrolidone, or the like), lubricants (for example, magnesium stearate, talc, or the like), disintegrants (for example, carboxymethylcellulose calcium, or the like), and the like, may be employed.

BEST MODES FOR CARRYING OUT THE INVENTION

In the following, the present invention is illustrated in detail by the following examples. However, it should be understood that the present invention is not limited to the examples described below.

EXAMPLE 1

Synthesis of N-(4-butyl-2-methylphenyl)-N'-hydroxy-formamidine

4-Butyl-2-methylaniline (129.18 g) and ethyl orthoformate (234.66 g) were stirred for 11 hours at 100° C. Subsequently, the excess of the ethyl orthoformate was removed. The obtained crude product was dissolved in methanol (200 ml). To a methanol solution (500 ml) of hydroxylamine hydrochloride (65.59 g), a methanol solution (350 ml) of sodium methoxide (51.02 g) was added dropwise at 0° C. to neutralize. The precipitated sodium chloride was filtered off. The filtrate was added dropwise to the methanol solution of the crude product, and subsequently, the mixture was stirred for 15 hours at room temperature. The methanol was removed. The obtained residue was dissolved in 800 ml of chloroform, and subsequently, washed with water and saturated brine. The organic layer was dried over anhydrous magnesium sulfate and then the solvent was removed. The obtained residue was washed with hexane to yield 63.66 g of crude crystals of the target compound. One portion of the crude crystals (35.47 g) was recrystallized from hexane:ethyl acetate (1:4) to yield 29.85g of the target compound as a colorless powder (Compound 1 in Table 1 described below).

Melting point: 131.5–134.0° C.

EXAMPLE 2

Synthesis of N-(4-tert-butylphenyl)-N'-hydroxyformamidine 4-tert-Butylaniline (3.9 g) and ethyl orthoformate (7.9 g) were stirred for 6.5 hours at 100° C. Subsequently, the excess of the ethyl orthoformate was removed. The obtained crude product was dissolved in methanol (10 ml). To a methanol solution (20 ml) of hydroxylamine hydrochloride (2.1 g), a methanol solution (15 ml) of sodium methoxide (1.6 g) was added droipwse at 0° C. to neutralize. The precipitated sodium chloride was filtered off. The filtrate was added dropwise to the methanol solution of the crude product, and subsequently, the mixture was stirred for 1.5 hours at room temperature. The methanol was removed. The obtained residue was dissolved in 50 ml of chloroform, and subsequently, washed with water and saturated brine. The organic layer was dried over anhydrous magnesium sulfate and then concentrated. The obtained residue was purified by silica gel column chromatography (hexane:ethyl acetate= 4:1) to yield 1.65 g of the target compound (Compound 2 in Table 1 described below).

Melting point: 113.5–114.5° C.

EXAMPLE 3

Synthesis of N-(4-methoxycarbonylphenyl)-N'-hydroxyformamidine

A mixture of 4-aminobenzoic acid methyl ester (1.98 g) and ethyl orthoforniate (4.07 g) was stirred for 16 hours at 100° C. Subsequently, the excess of the ethyl orthoformate was removed. To the obtained residue, a methanol solution (16 ml) of hydroxylamine prepared from hydroxylamine hydrochloride (1.50 g) and sodium methoxide (1.10 g) was added, and the mixture was stirred for 6 hours at room temperature. The solvent was removed and subsequently, to the residue, chloroform was added. Subsequently, it was washed successively with water and saturated brine. The organic layer was dried over anhydrous magnesium sulfate and the solvent was removed. The residue was purified by silica gel column chromatography (eluent; n-hexane:ethyl acetate), and subsequently, by recrystallized from chloroform—methanol to yield the target compound (Compound 123 in Table 1 described below) (0.32 g) as a colorless powder.

Melting point: 167.0–167.5° C.

EXAMPLE 4

Synthesis of N-(2-aminosulfonylphenyl)-N'-hydroxyformamidine

A mixture of 2-aminobenzsulfonamide (3.0 g), ethyl orthoformate (5.15 g), and ethyl acetate (20 ml) was stirred for 5 hours at 100° C. Subsequently, the excess of the ethyl orthoformate was removed. To a methanol solution (30 ml) of the residue, a methanol solution (40 ml) of hydroxylamine prepared from hydroxylamine hydrochloride (1.50 g) and sodium methoxide (1.10 g) was added, and the mixture was stirred for 2 days at room temperature. The solvent was removed and subsequently, to the residue, chloroform was added, and washed successively with water and saturated brine. The organic layer was dried over anhydrous magnesium sulfate and the solvent was removed. The residue was purified by silica gel column chromatography (eluent:ethyl acetate) to yield the target compound (Compound 236 in Table 1 described below) (0.73 g) as a colorless powder.

Melting point: 130.5–131.5° C.

EXAMPLE 5

Synthesis of N-[4-(pyridin-2-ylmethoxy)phenyl]-N'-hydroxyformamidine

A mixture of 4-(pyridin-2-ylmethoxy)aniline (1.715 g) and ethyl orthoformate (2.613 g) was stirred for 14 hours at 100° C. Subsequently, the excess of the ethyl orthoformate was removed. To a methanol solution (20 ml) of the residue, a 1M methanol solution (10 ml) of hydroxylamine was added, and the mixture was stirred for 2.5 days at room temperature. The solvent was removed and subsequently, to the residue, chloroformwas added. Subsequently, it was washed with water and saturated brine. The organic layer was dried over anhydrous magnesium sulfate and the solvent was removed. The obtained residue was purified by recrystallization from ethyl acetate to yield the target compound (Compound 345 in Table 1 described below) (0.524 g) as a colorless powder.

Melting point: 159.5–161.0° C.

EXAMPLE 6

Synthesis of N-[4-(benzylthio)phenyl]-N'-hydroxyformamidine

A mixture of 4-(benzylthio) aniline (1.18 g) and ethyl orthoformate (1.78 g) was stirred for 12 hours at 100° C. Subsequently, the excess of the ethyl orthoformate was removed. To a methanol solution (20 ml) of the residue, a 1M methanol solution (10 ml) of hydroxylamine was added, and the mixture was stirred for 2.5 days at room temperature. The solvent was removed and subsequently, to the residue, chloroformwas added. Subsequently, it was washed with water and saturated brine. The organic layer was dried over anhydrous magnesium sulfate and the solvent was removed. The obtained residue was recrystallized from ethyl acetate to yield the target compound (Compound 441 in Table 1 described below) (0.43 g) as a colorless powder.

Meeting point: 166° C.

EXAMPLE 7

The compounds shown in Table 1 described below were obtained by carrying out the similar procedures as those of Example 1. The compounds obtained in Examples 1 to 6, together with the other compounds are also shown in Table 1.

The Rf values in Table 1 corresponds to the Rf values in the case of development with a mixture of ethyl acetate: hexane (1:2) (no mark) or in the case of development with a mixture of chloroform:methanol (9:1) (marked as *), employing thin layer chromatography Silica gel 60 $F_{254}$, produced by Merck, or NH-TLC plates, produced by Fuji Silysia Chemical Ltd. In addition, the term "post" or "nega" denotes data of the cation peak (M+H) or the anion peak (M–H), observed in a positive mode or a negative mode upon measurement of mass spectrum by means of the ESI method.

TABLE 1

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 1 | 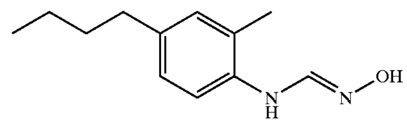 | 131.5–134.0 | 207 | 207 | | 205 | 0.56 | SiO2 (NH) | EtOAc:MeOH = 95:5 | 100.5 | 3.5 |
| Comp. 2 | 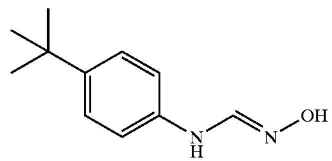 | 113.5–114.5 | 193 | | 191 | | 0.13 | SiO2 | Hexane:AcOEt = 2:1 | 97.0 | 7.8 |
| Comp. 3 | 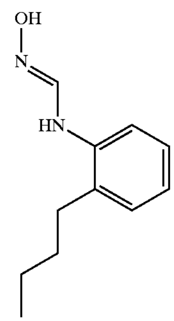 | 84.5–85.5 | 193 | | 191 | | 0.22 | SiO2 | Hexane:AcOEt = 2:1 | 98.9 | |
| Comp. 4 | 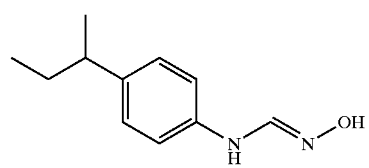 | 101.0–102.5 | | | 191 | | 0.15 | SiO2 | Hexane:AcOEt = 2:1 | 107.6 | 3 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 5 | 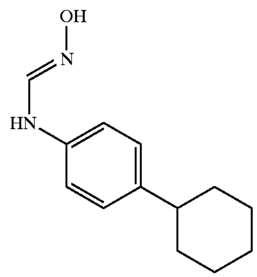 | 153.0–154.0 | 219 | | 217 | | 0.13 | SiO2 | Hexane:AcOEt = 2:1 | 99.9 | 3.8 |
| Comp. 6 | 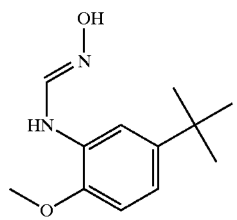 | 119.5–120.5 | 223 | | 221 | | 0.20 | SiO2 | Hexane:AcOEt = 2:1 | 99.9 | |
| Comp. 7 | 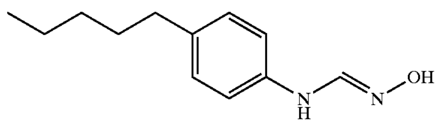 | 122.5–124.0 | 207 | | 205 | | 0.14 | SiO2 | Hexane:AcOEt = 2:1 | 110.5 | 12.1 |
| Comp. 8 | 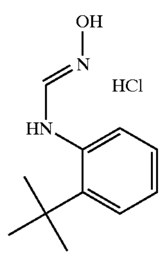 | 141.0–142.0 | 193 | | 191 | | 0.21 | SiO2 | Hexane:AcOEt = 2:1 | 99.9 | |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 9 | 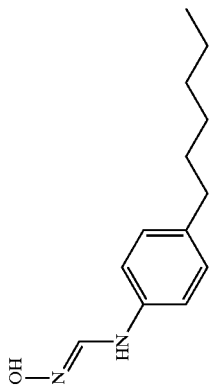 | 108.0–110.0 | 221 | | 219 | | 0.15 | SiO2 | Hexane:AcOEt = 2:1 | 99.9 | 4.9 |
| Comp. 10 | 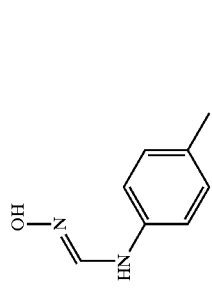 | 143.5–144.5 | 185 | | 151 | | 0.12 | SiO2 | Hexane:AcOEt = 2:1 | 89.5 | 669.0 |
| Comp. 11 | 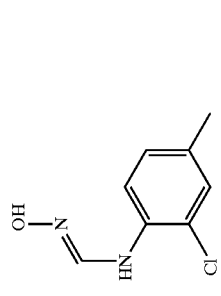 | 151.0–152.5 | | | 183 | | 0.18 | SiO2 | Hexane:AcOEt = 2:1 | 92.7 | 297.1 |
| Comp. 12 | 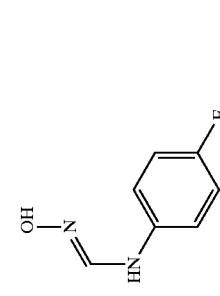 | 139.5–140.5 | 155 | | | | 0.08 | SiO2 | Hexane:AcOEt = 2:1 | 77.1 | 1415.5 |

TABLE 1-continued

| Comp. | Chemical Structure | mp. | M+H (ESI) | M+H (APCI) | M−H (ESI) | M−H (APCI) | Rf value | TLC* | Developing solvent | Inhibition rate (1 μM) | IC50 (nM) |
|---|---|---|---|---|---|---|---|---|---|---|---|
| Comp. 13 | 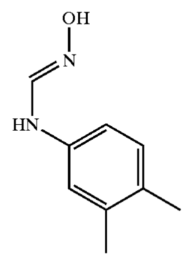 | 116.0–118.0 | 165 | | 163 | | 0.12 | SiO2 | Hexane:AcOEt = 2:1 | 95.9 | 117.9 |
| Comp. 14 | 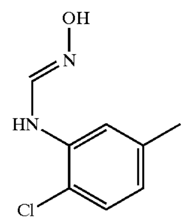 | 151.0–153.0 | | | 183 | | 0.19 | SiO2 | Hexane:AcOEt = 2:1 | 91.7 | 162.8 |
| Comp. 15 | 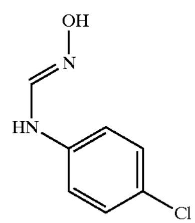 | 155.5–156.0 | 171 | | 169 | | 0.10 | SiO2 | Hexane:AcOEt = 2:1 | 92.9 | 287.7 |
| Comp. 16 | 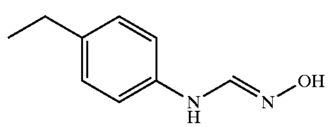 | 141.0–142.0 | 165 | | 163 | | 0.12 | SiO2 | Hexane:AcOEt = 2:1 | 97.6 | 6.6 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 17 | 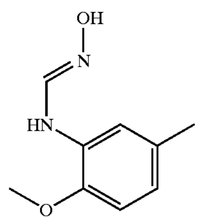 | 136.5–139.0 | 181 | | 179 | | 0.15 | SiO2 | Hexane:AcOEt = 2:1 | 85.3 | |
| Comp. 18 | 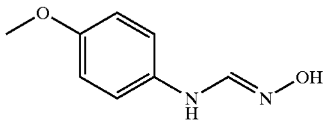 | 139.0–140.0 | 167 | | 165 | | 0.06 | SiO2 | Hexane:AcOEt = 2:1 | 94.6 | 45.2 |
| Comp. 19 | 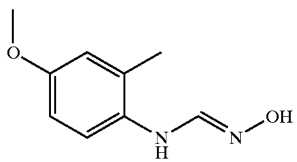 | 144.0–145.0 | 181 | | 179 | | 0.08 | SiO2 | Hexane:AcOEt = 2:1 | 88.0 | 337.6 |
| Comp. 20 | 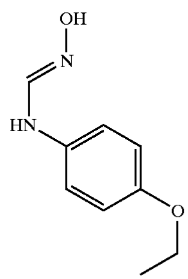 | 149.0–150.0 | 181 | | 179 | | 0.07 | SiO2 | Hexane:AcOEt = 2:1 | 97.5 | 227.6 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 21 | 3-ethylphenyl oxime structure | 115.5–116.5 | 165 | | 163 | | 0.14 | SiO2 | Hexane:AcOEt = 2:1 | 81.1 | |
| Comp. 22 | 2,4-dimethylphenyl oxime structure | 139.0–141.0 | | | | | 0.16 | SiO2 | Hexane:AcOEt = 2:1 | 95.7 | |
| Comp. 23 | 3-chlorophenyl oxime structure | 110.0–111.5 | 171 | | 169 | | 0.12 | SiO2 | Hexane:AcOEt = 2:1 | 82.8 | 475.8 |
| Comp. 24 | 3,4-dichlorophenyl oxime structure | 119.0–120.5 | 205 | | | | 0.10 | SiO2 | Hexane:AcOEt = 2:1 | 89.2 | 519.7 |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 25 | 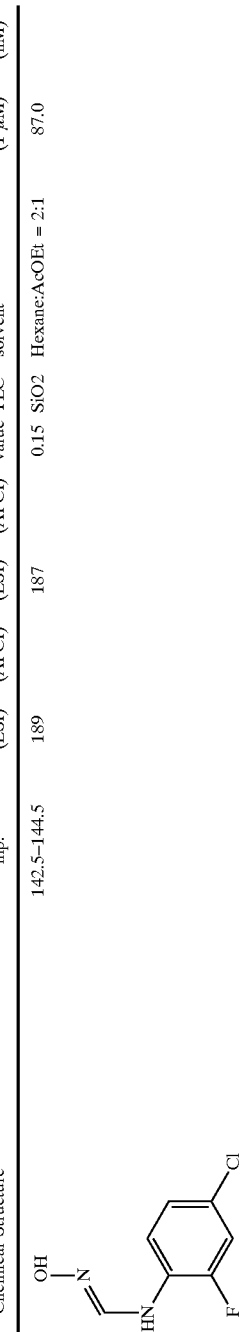 | 142.5–144.5 | 189 | | 187 | | 0.15 | SiO2 | Hexane:AcOEt = 2:1 | 87.0 | |
| Comp. 26 | 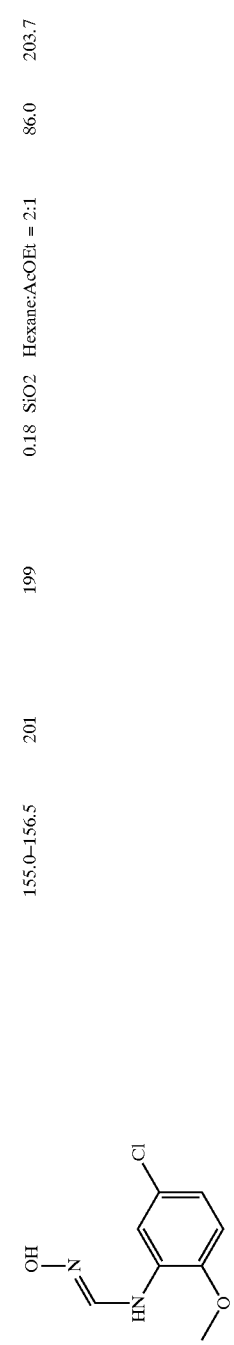 | 155.0–156.5 | 201 | | 199 | | 0.18 | SiO2 | Hexane:AcOEt = 2:1 | 86.0 | 203.7 |
| Comp. 27 | 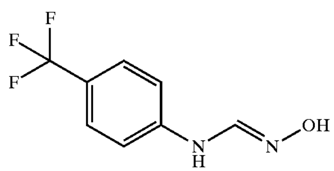 | 140.5–142.0 | 205 | | 203 | | 0.10 | SiO2 | Hexane:AcOEt = 2:1 | 103.3 | 1.7 |
| Comp. 28 | 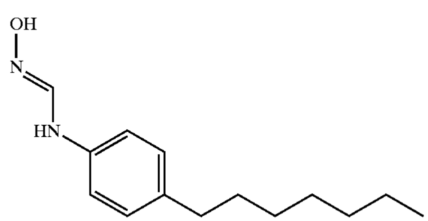 | 119.0–120.5 | 235 | | 233 | | 0.15 | SiO2 | Hexane:AcOEt = 2:1 | 92.5 | 4.7 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 29 | 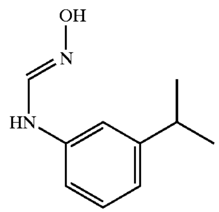 | 93.0–94.5 | 179 | | 177 | | 0.13 | SiO2 | Hexane:AcOEt = 2:1 | 93.6 | |
| Comp. 30 | 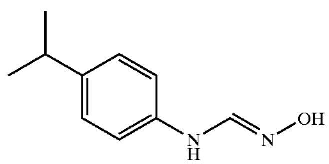 | 143.0–143.5 | 179 | | 177 | | 0.12 | SiO2 | Hexane:AcOEt = 2:1 | 103.0 | 2.4 |
| Comp. 31 | 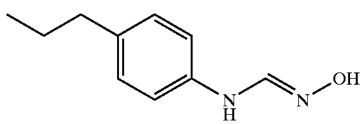 | 131.0–132.0 | 179 | | | | 0.12 | SiO2 | Hexane:AcOEt = 2:1 | 97.8 | 6.6 |
| Comp. 32 | 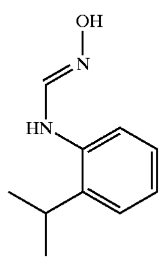 | 114.0–115.0 | 179 | | | | 0.16 | SiO2 | Hexane:AcOEt = 2:1 | 87.2 | |
| Comp. 33 | 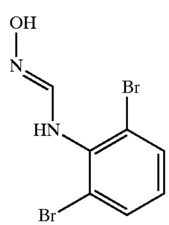 | 171.0 | | | 291 | | 0.23 | SiO2 | Hexane:AcOEt = 2:1 | 91.9 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 34 | 2,4-dibromo-phenyl hydroxyiminomethyl amine | 163.0–163.5 | 293 | | 291 | | 0.17 | SiO2 | Hexane:AcOEt = 2:1 | 90.6 | 79.7 |
| Comp. 35 | 4-bromo-2-chloro-phenyl hydroxyiminomethyl amine | 161.0 | | | | | | | | 95.4 | 86.5 |
| Comp. 36 | 4-bromo-phenyl hydroxyiminomethyl amine | 163.0–164.0 | 215 | | 213 | | 0.17 | SiO2 | Hexane:AcOEt = 2:1 | 98.3 | 136.5 |
| Comp. 37 | methyl 4-(hydroxyiminomethyl-amino)benzoate | 167.0–167.5 | 195 | | 193 | | 0.06 | SiO2 | Hexane:AcOEt = 2:1 | 92.7 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 38 | 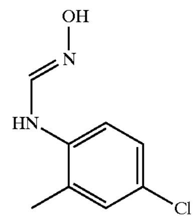 | 151.0–152.5 | 185 | | 183 | | 0.13 | SiO2 | Hexane:AcOEt = 2:1 | 89.8 | 79.8 |
| Comp. 39 | 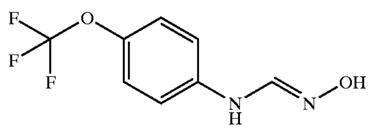 | 110.0–113.0 | 221 | | 219 | | 0.10 | SiO2 | Hexane:AcOEt = 2:1 | 99.0 | 22 |
| Comp. 40 | 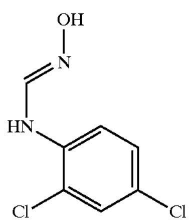 | 160.0–161.0 | 205 | | 203 | | 0.16 | SiO2 | Hexane:AcOEt = 2:1 | 98.2 | |
| Comp. 41 | 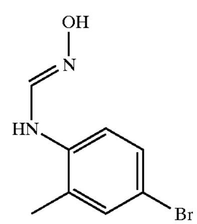 | 161.0–161.5 | 229 | | 227 | | 0.13 | SiO2 | Hexane:AcOEt = 2:1 | 96.6 | 49.0 |

TABLE 1-continued

| Comp. | Chemical Structure | mp. | M + H (ESI) | M + H (APCI) | M – H (ESI) | M – H (APCI) | Rf value | TLC* | Developing solvent | Inhibition rate (1 μM) | IC50 (nM) |
|---|---|---|---|---|---|---|---|---|---|---|---|
| Comp. 42 | 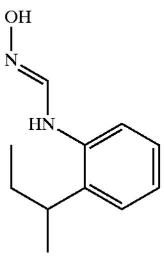 | 144.0–145.0 | | | | | 0.44 | SiO2 | CHCl3:MeOH = 9:1 | 99.9 | |
| Comp. 43 | 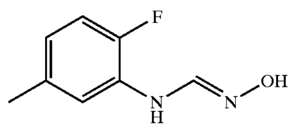 | 123.0–124.0 | 169 | | 167 | | 0.30 | SiO2 | CHCl3:MeOH = 9:1 | | 168.1 |
| Comp. 44 | 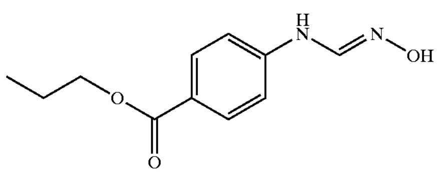 | 145.0–146.0 | 223 | | 221 | | 0.32 | SiO2 | CHCl3:MeOH = 9:1 | | 8.1 |
| Comp. 45 | 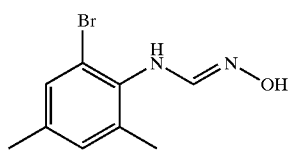 | 163.5–164.5 | 243 | | | | 0.45 | SiO2 | CHCl3:MeOH = 9:1 | 53.5 | |
| Comp. 46 | 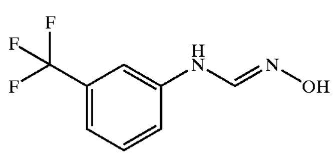 | 100.5–102.0 | 205 | | 203 | | 0.24 | SiO2 | CHCl3:MeOH = 9:1 | 48.5 | 355.3 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 47 | 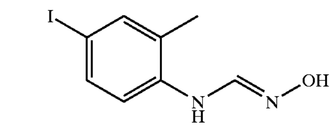 | 166.0–166.5 | 277 | | 275 | | 0.37 | SiO2 | CHCl3:MeOH = 9:1 | 94.8 | 6.5 |
| Comp. 48 | 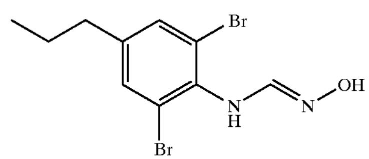 | 155.0–156.0 | 335 | | | | 0.52 | SiO2 | CHCl3:MeOH = 9:1 | | |
| Comp. 49 | 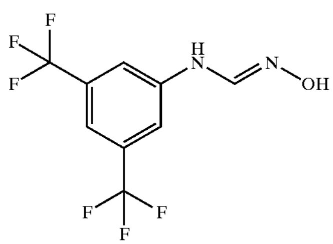 | 122.5–124.0 | | | 271 | | 0.44 | SiO2 | CHCl3:MeOH = 9:1 | 46.7 | |
| Comp. 50 | 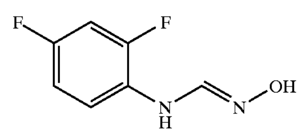 | 155.5–156.5 | 173 | | 171 | | 0.34 | SiO2 | CHCl3:MeOH = 9:1 | | 25.5 |
| Comp. 51 | 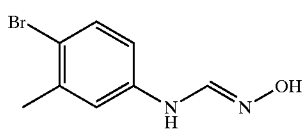 | 157.0–158.0 | 229 | | 227 | | 0.42 | SiO2 | CHCl3:MeOH = 9:1 | 50.2 | 21.8 |
| Comp. 52 | 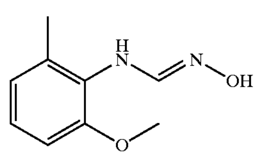 | 145.0–146.0 | 181 | | | | 0.43 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 53 | 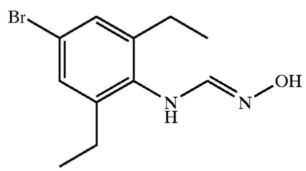 | 159.0–160.0 | 271 | | | | 0.66 | SiO2 | CHCl3:MeOH = 9:1 | | |
| Comp. 54 | 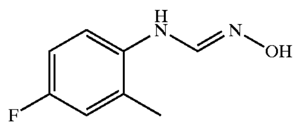 | 162.5–163.5 | | | | | 0.43 | SiO2 | CHCl3:MeOH = 9:1 | | |
| Comp. 55 | 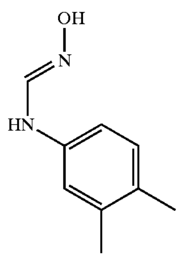 | 130.5–132.0 | 277 | | 275 | | 0.5 | SiO2 | CHCl3:MeOH = 9:1 | 31.3 | |
| Comp. 56 | 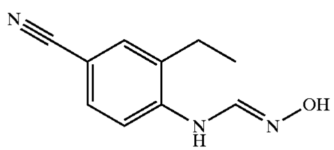 | 144.0–145.5 | 190 | | 188 | | 0.42 | SiO2 | CHCl3:MeOH = 9:1 | 50.6 | |
| Comp. 57 | 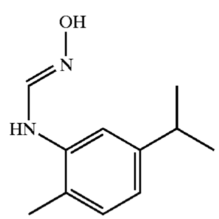 | | 193 | | 191 | | 0.22 | SiO2 | Hexane:AcOEt = 2:1 | 59.1 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 58 | 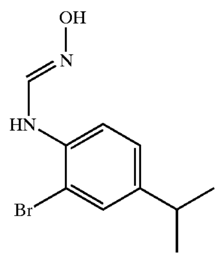 | 146.5–148.0 | 257 | | 255 | | 0.21 | SiO2 | Hexane:AcOEt = 2:1 | 99.9 | 7.1 |
| Comp. 59 | 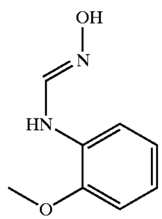 | | 167 | | 165 | | 0.13 | SiO2 | Hexane:AcOEt = 2:1 | 49.0 | |
| Comp. 60 | 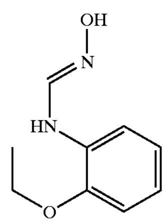 | | 181 | | 179 | | 0.15 | SiO2 | Hexane:AcOEt = 2:1 | | |
| Comp. 61 | 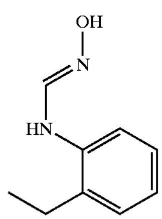 | | | | 163 | | 0.17 | SiO2 | Hexane:AcOEt = 2:1 | | |

TABLE 1-continued

| Comp. | Chemical Structure | mp. | M + H (ESI) | M + H (APCI) | M - H (ESI) | M - H (APCI) | Rf value | TLC* | Developing solvent | Inhibition rate (1 μM) | IC50 (nM) |
|---|---|---|---|---|---|---|---|---|---|---|---|
| Comp. 62 | 3-methylphenyl formamide oxime | | 151 | | | | 0.12 | SiO2 | Hexane:AcOEt = 2:1 | 69.5 | |
| Comp. 63 | 2,3-dimethylphenyl formamide oxime | | 165 | | 163 | | 0.15 | SiO2 | Hexane:AcOEt = 2:1 | 49.3 | |
| Comp. 64 | 3,5-dimethylphenyl formamide oxime | | | | 163 | | 0.13 | SiO2 | Hexane:AcOEt = 2:1 | | |

TABLE 1-continued

| Comp. | Chemical Structure | mp. | M + H (ESI) | M + H (APCI) | M – H (ESI) | M – H (APCI) | Rf value | TLC* | Developing solvent | Inhibition rate (1 μM) | IC50 (nM) |
|---|---|---|---|---|---|---|---|---|---|---|---|
| Comp. 65 | 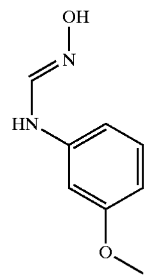 | | 167 | | 165 | | 0.08 | SiO2 | Hexane:AcOEt = 2:1 | 59.3 | |
| Comp. 66 | 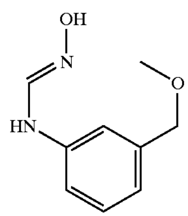 | | 181 | | 179 | | 0.10 | SiO2 | Hexane:AcOEt = 2:1 | 41.2 | |
| Comp. 67 | 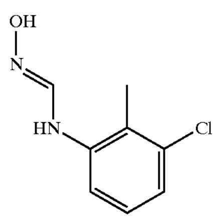 | | 185 | | 183 | | 0.15 | SiO2 | Hexane:AcOEt = 2:1 | 48.4 | |
| Comp. 68 | 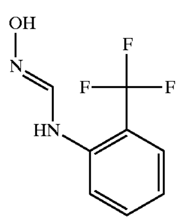 | | 205 | | 203 | | 0.15 | SiO2 | Hexane:AcOEt = 2:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 69 | 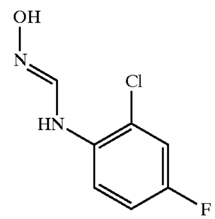 | | 189 | | 187 | | 0.15 | SiO2 | Hexane:AcOEt = 2:1 | 58.7 | |
| Comp. 70 | 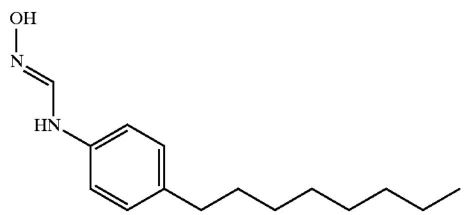 | | 249 | | 247 | | 0.15 | SiO2 | Hexane:AcOEt = 2:1 | 32.9 | |
| Comp. 71 | 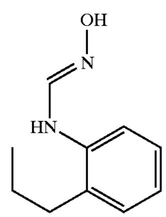 | | 179 | | 177 | | 0.18 | SiO2 | Hexane:AcOEt = 2:1 | 42.5 | |
| Comp. 72 | 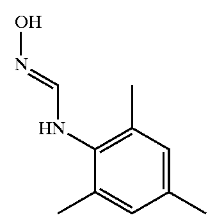 | 168.0–169.0 | 179 | | | | 0.12 | SiO2 | Hexane:AcOEt = 2:1 | 99.2 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 73 | 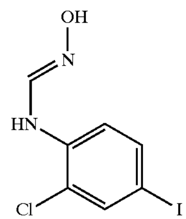 | | 297 | | 295 | | 0.18 | SiO2 | Hexane:AcOEt = 2:1 | 99.9 | |
| Comp. 74 | 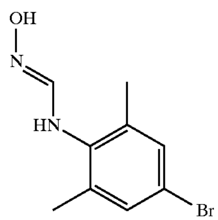 | | 243 | | 241 | | 0.11 | SiO2 | Hexane:AcOEt = 2:1 | 43.7 | |
| Comp. 75 | 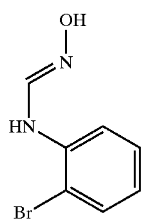 | | 215 | | 213 | | 0.16 | SiO2 | Hexane:AcOEt = 2:1 | 48.9 | |
| Comp. 76 | 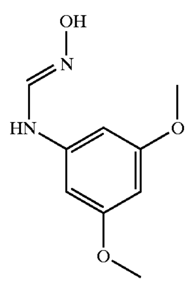 | | | | 195 | | 0.08 | SiO2 | Hexane:AcOEt = 2:1 | 35.1 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 77 | 4-bromo-2-(trifluoromethyl)phenyl derivative | | | | 281 | | 0.17 | SiO2 | Hexane:AcOEt = 2:1 | 49.0 | |
| Comp. 78 | 3,4-dimethoxyphenyl derivative | | 197 | | 195 | | 0.03 | SiO2 | Hexane:AcOEt = 2:1 | 36.3 | |
| Comp. 79 | 2-fluorophenyl derivative | | 155 | | 153 | | 0.15 | SiO2 | Hexane:AcOEt = 2:1 | 35.3 | |
| Comp. 80 | 2-chloro-5-(trifluoromethyl)phenyl derivative | | 239 | | 237 | | 0.32 | SiO2 | Hexane:AcOEt = 2:1 | 37.2 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 81 | HO-N=CH-NH-(2,3-dichlorophenyl) | | 205 | | 203 | | 0.14 | SiO2 | Hexane:AcOEt = 2:1 | 51.3 | |
| Comp. 82 | HO-N=CH-NH-(3-bromophenyl) | 133.5–134.5 | 215 | | 213 | | 0.12 | SiO2 | Hexane:AcOEt = 2:1 | 70.9 | |
| Comp. 83 | HO-N=CH-NH-(2,5-di-tert-butylphenyl) | | 249 | | | | 0.46 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 84 | 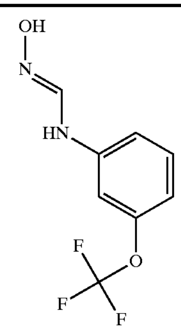 | | 221 | | 219 | | 0.27 | SiO2 | CHCl3:MeOH = 9:1 | | |
| Comp. 85 | 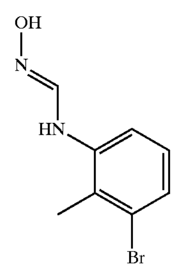 | | 229 | | 227 | | 0.37 | SiO2 | CHCl3:MeOH = 9:1 | | |
| Comp. 86 | 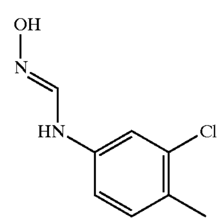 | | 185 | | 183 | | 0.29 | SiO2 | CHCl3:MeOH = 9:1 | 58.7 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 87 | 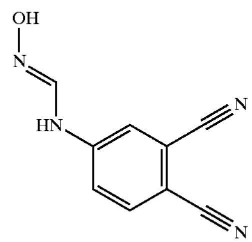 | | 187 | | | | 0.22 | SiO2 | CHCl3:MeOH = 9:1 | | |
| Comp. 88 | 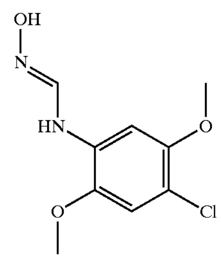 | | 231 | | 229 | | 0.31 | SiO2 | CHCl3:MeOH = 9:1 | | |
| Comp. 89 | 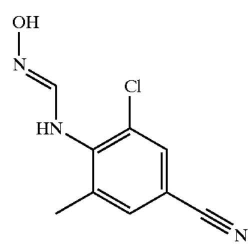 | | 210 | | 208 | | 0.32 | SiO2 | CHCl3:MeOH = 9:1 | | |
| Comp. 90 | 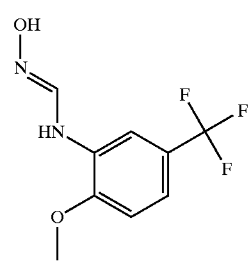 | | 235 | | | | 0.33 | SiO2 | CHCl3:MeOH = 9:1 | 36.5 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 91 | HO-N=CH-NH-(3-iodophenyl) | | 263 | | | | 0.27 | SiO2 | CHCl3:MeOH = 9:1 | 36.6 | |
| Comp. 92 | HO-N=CH-NH-(4-cyano-3-trifluoromethylphenyl) | | 230 | | 228 | | 0.51 | SiO2 | CHCl3:MeOH = 9:1 | | |
| Comp. 93 | HO-N=CH-NH-(4-ethynylphenyl) | | | | | | 0.21 | SiO2 | CHCl3:MeOH = 9:1 | | |
| Comp. 94 | HO-N=CH-NH-(4-ethoxy-2-nitrophenyl) | | 226 | | 224 | | 0.29 | SiO2 | CHCl3:MeOH = 9:1 | 41.2 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 95 | 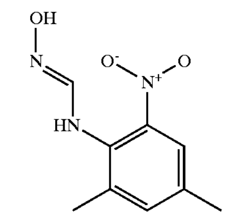 | | 210 | | 208 | | 0.32 | SiO2 | CHCl3:MeOH = 9:1 | 44.5 | |
| Comp. 96 | 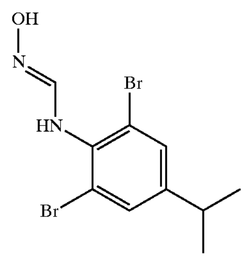 | | 335 | | | | 0.40 | SiO2 | CHCl3:MeOH = 9:1 | | |
| Comp. 97 | 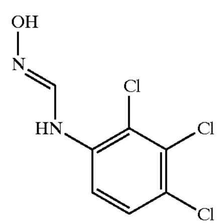 | | 239 | | 237 | | 0.32 | SiO2 | CHCl3:MeOH = 9:1 | | |
| Comp. 98 | 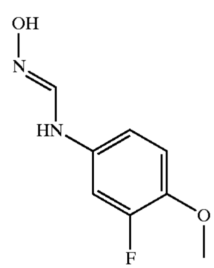 | | 185 | | | | 0.21 | SiO2 | CHCl3:MeOH = 9:1 | 43.9 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 99 | 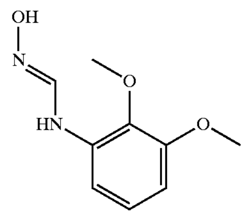 | | 197 | | 195 | | 0.29 | SiO2 | CHCl3:MeOH = 9:1 | 40.8 | |
| Comp. 100 | 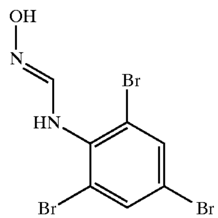 | | 370 | | 368 | | 0.38 | SiO2 | CHCl3:MeOH = 9:1 | 44.3 | |
| Comp. 101 | 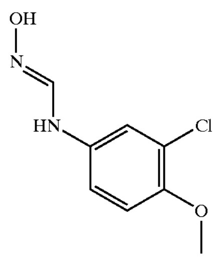 | | 201 | | 199 | | 0.24 | SiO2 | CHCl3:MeOH = 9:1 | 52.4 | |
| Comp. 102 | 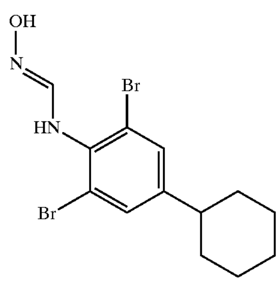 | | 375 | | 373 | | 0.41 | SiO2 | CHCl3:MeOH = 9:1 | 44.4 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 103 | 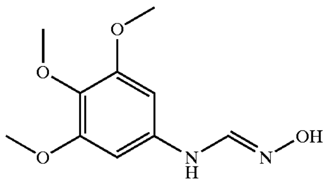 | 143.0–146.0 | 227 | | 225 | | 0.21 | SiO2 | CHCl3:MeOH = 9:1 | | |
| Comp. 104 | 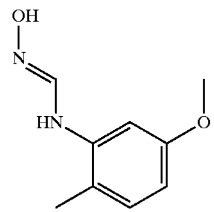 | | 181 | | | | 0.39 | SiO2 | CHCl3:MeOH = 9:1 | 31.9 | |
| Comp. 105 | 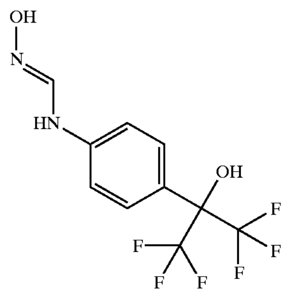 | | 303 | | 301 | | 0.12 | SiO2 | CHCl3:MeOH = 9:1 | 46.7 | |
| Comp. 106 | 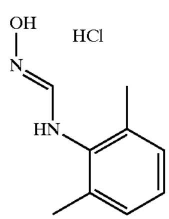 | | 165 | | 163 | | 0.25 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 107 | (5-methyl-2-nitrophenyl aminomethylene oxime) | | 196 | | 194 | | 0.37 | SiO2 | CHCl3:MeOH = 9:1 | | |
| Comp. 108 | (4,5-dimethoxy-2-chlorophenyl aminomethylene oxime) | | 231 | | | | 0.39 | SiO2 | CHCl3:MeOH = 9:1 | 36.4 | |
| Comp. 109 | (3-chloro-4-cyanophenyl aminomethylene oxime) | | 196 | | 194 | | 0.13 | SiO2 | CHCl3:MeOH = 9:1 | | |
| Comp. 110 | (2-ethyl-6-methylphenyl aminomethylene oxime) | | | | | | 0.13 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 111 | 2,4,6-trifluorophenyl derivative | | 191 | | | | 0.37 | SiO2 | CHCl3:MeOH = 9:1 | | |
| Comp. 112 | 4-cyanophenyl derivative | | | | 160 | | 0.24 | SiO2 | CHCl3:MeOH = 9:1 | 37.4 | |
| Comp. 113 | 2-cyano-4-chlorophenyl derivative | | 196 | | 194 | | 0.08 | SiO2 | CHCl3:MeOH = 9:1 | | |
| Comp. 114 | 3,4-diethoxyphenyl derivative · HCl | | | | 223 | | 0.21 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 115 | 2,4,5-trichlorophenyl structure | | 239 | | 237 | | 0.4 | SiO2 | CHCl3:MeOH = 9:1 | | |
| Comp. 116 | 2,5-dimethoxyphenyl structure | | 197 | | 195 | | 0.37 | SiO2 | CHCl3:MeOH = 9:1 | | |
| Comp. 117 | 2-bromo-4-chlorophenyl structure | | 249 | | 247 | | 0.39 | SiO2 | CHCl3:MeOH = 9:1 | 71.6 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 118 | (2,5-diethoxyphenyl derivative) | | 225 | | 223 | | 0.41 | SiO2 | CHCl3:MeOH = 9:1 | | |
| Comp. 119 | (3,5-di-tert-butylphenyl derivative) | | 249 | | | | 0.27 | SiO2 | CHCl3:MeOH = 9:1 | | |
| Comp. 120 | (2,3-difluorophenyl derivative) | | 173 | | 171 | | 0.37 | SiO2 | CHCl3:MeOH = 9:1 | | |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 121 | 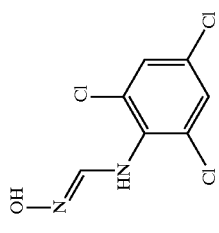 | 166.5–167.0 | | | 237 | | 0.29 | SiO2 | EtOAc:hexane = 1:2 | 72.0 | |
| Comp. 122 | 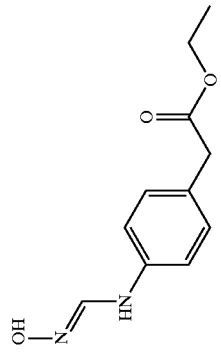 | 106.0–107.5 | 223 | | 221 | | 0.05 | SiO2 | EtOAc:hexane = 1:2 | 94.7 | 28.9 |
| Comp. 123 | 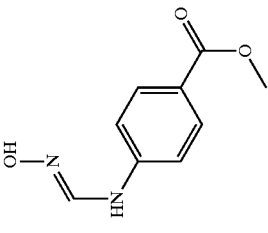 | 167.0–167.5 | | 195 | 193 | | 0.47 | SiO2 (NH) | EtOAc:MeOH = 95:5 | 92.7 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 124 | (3-phenoxyphenyl formaldoxime NH structure) | 100.0–102.0 | | | 227 | | 0.12 | SiO2 | EtOAc:hexane = 1:2 | 92.2 | 354.5 |
| Comp. 125 | (2-methoxy-6-trifluoromethylphenyl formaldoxime NH structure) | 138.0–139.5 (dec.) | | | | | | | | 67.6 | |
| Comp. 126 | (4-fluoro-2-nitrophenyl formaldoxime NH structure) | 172.5–173.0 (dec.) | | | | | | | | 34.9 | |
| Comp. 127 | (ethyl 3-aminobenzoate formaldoxime structure) | 137.5–138.5 | | 209 | | 207 | 0.53 | SiO2 (NH) | EtOAc:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 128 | 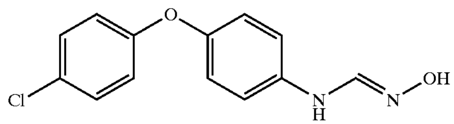 | 143.0–145.0 | 263 | | | | 0.26 | SiO2 | CHCl3:MeOH = 9:1 | 102.0 | 7.0 |
| Comp. 129 | 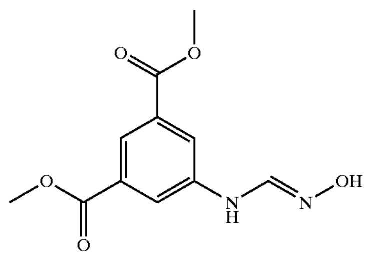 | 183.0–183.5 | | 253 | 251 | | 0.50 | SiO2 (NH) | EtOAc:MeOH = 95:5 | | |
| Comp. 130 | 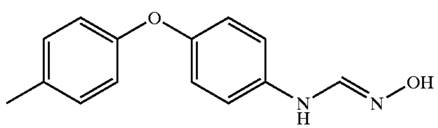 | 155.0–156.0 | 243 | | 241 | | 0.10 | SiO2 | EtOAc:hexane = 1:2 | 116.5 | 6.9 |
| Comp. 131 | 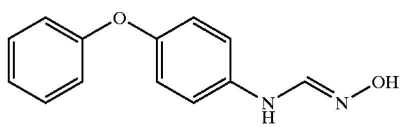 | 144.0–145.5 | 229 | | 227 | | 0.09 | SiO2 | EtOAc:hexane = 1:2 | 89.2 | 26 |
| Comp. 132 | 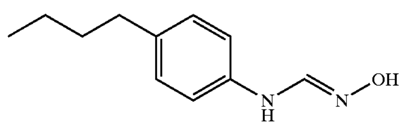 | 122.0–123.5 | | | | | | | | 117.6 | 3.9 |
| Comp. 133 | 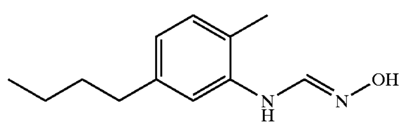 | 116.5–117.5 | | | | | | | | 48.6 | 720 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 134 | 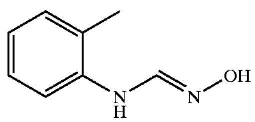 | 154.0–154.5 | | | | | | | | 57.4 | 3625 |
| Comp. 135 | 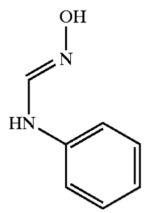 | | 137 | | 135 | | 0.10 | SiO2 | EtOAc:hexane = 1:2 | 49.3 | |
| Comp. 136 | 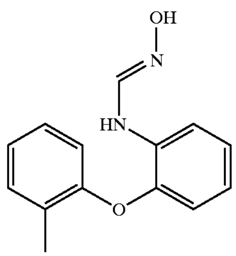 | | 243 | | 241 | | 0.17 | SiO2 | EtOAc:hexane = 1:2 | | |
| Comp. 137 | 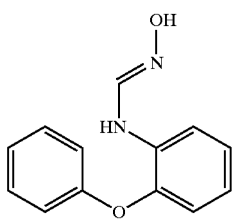 | | 229 | | 227 | | 0.15 | SiO2 | EtOAc:hexane = 1:2 | | |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 138 | 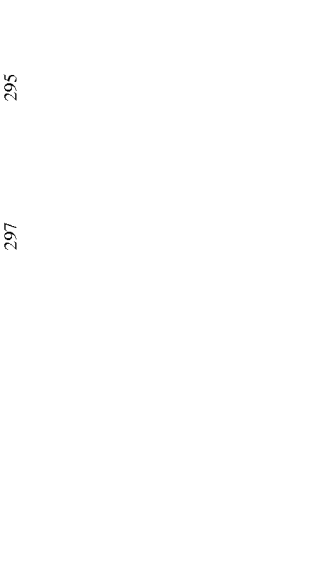 | | 297 | | 295 | | 0.11 | SiO2 | EtOAc:hexane = 1:2 | 44.0 | |
| Comp. 139 | 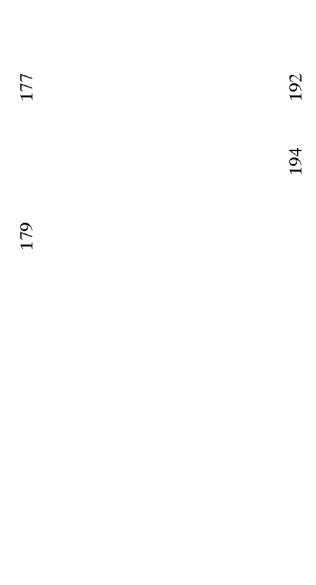 | | 179 | | 177 | | 0.13 | SiO2 | EtOAc:hexane = 1:2 | 69.7 | |
| Comp. 140 | 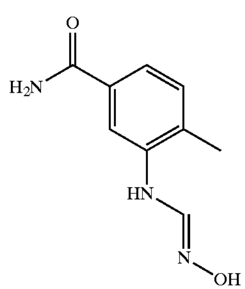 | | | 194 | | 192 | 0.23 | SiO2 (NH) | AcOEt:EtOH = 90:10 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 141 | acetamido-phenyl formaldoxime | | | 194 | 192 | | 0.06 | SiO2 | CHCl3:MeOH = 95:5 | | |
| Comp. 142 | phthalazine-dione formaldoxime | | | | 219 | | 0.22 | SiO2 | AcOEt:EtOH = 90:10 | | |
| Comp. 143 | nitro-methylphenyl formaldoxime | | 196 | 194 | | | 0.25 | SiO2 | CHCl3:MeOH = 95:5 | 37.3 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 144 | (2-methylsulfonylphenyl)-NH-CH=N-OH | | | 215 | 213 | | 0.13 | SiO2 | CHCl3:MeOH = 95:5 | | |
| Comp. 145 | (3-methylsulfonylphenyl)-NH-CH=N-OH | | | | 213 | | 0.11 | SiO2 | CHCl3:MeOH = 95:5 | | |
| Comp. 146 | (3-methoxy-5-trifluoromethylphenyl)-NH-CH=N-OH | | | 235 | 233 | | 0.25 | SiO2 (NH) | AcOEt | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 147 | 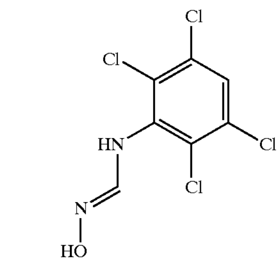 | | | 273 | 271 | | 0.26 | SiO2 (NH) | AcOEt | | |
| Comp. 148 | 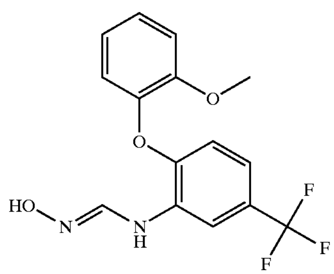 | | | 327 | 325 | | 0.32 | SiO2 (NH) | AcOEt | | |
| Comp. 149 | 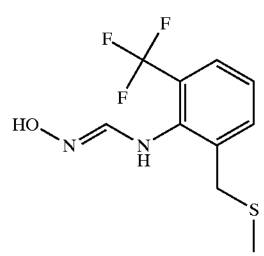 | | | 265 | 263 | | 0.34 | SiO2 (NH) | AcOEt | 36.5 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 150 | 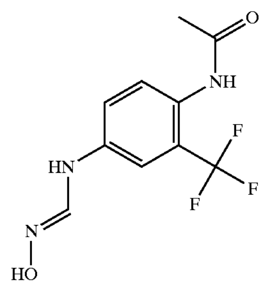 | | | 262 | 260 | | 0.15 | SiO2 (NH) | AcOEt | 34.1 | |
| Comp. 151 | 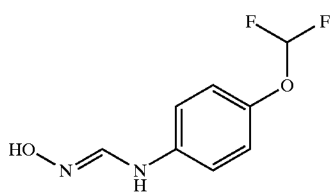 | | | 203 | 201 | | 0.20 | SiO2 (NH) | AcOEt | 108.2 | |
| Comp. 152 | 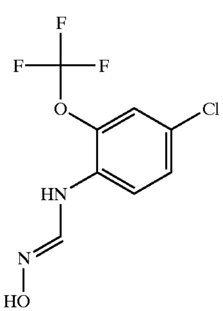 | | | 255 | 253 | | 0.28 | SiO2 (NH) | AcOEt | | |
| Comp. 153 | 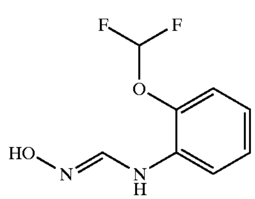 | | | 203 | 201 | | 0.29 | SiO2 (NH) | AcOEt | 39.4 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 154 | 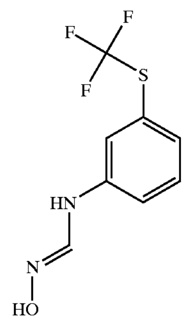 | | | 237 | 235 | | 0.24 | SiO2 (NH) | AcOEt | | |
| Comp. 155 | 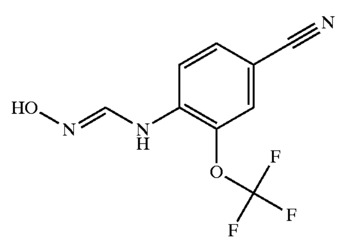 | | | 246 | 244 | | 0.23 | SiO2 (NH) | AcOEt | | |
| Comp. 156 | 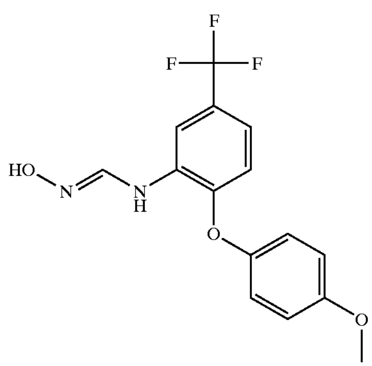 | | | 327 | 325 | | 0.32 | SiO2 (NH) | AcOEt | 39.4 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 157 | 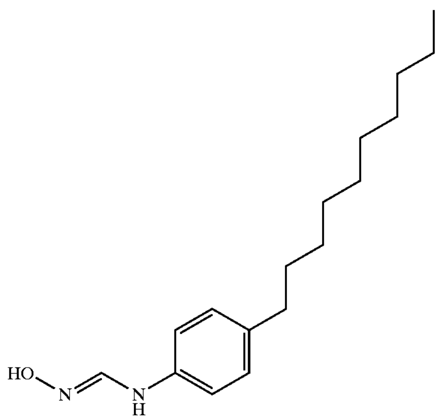 | | | 277 | 275 | | 0.28 | SiO2 (NH) | AcOEt | 121.4 | |
| Comp. 158 | 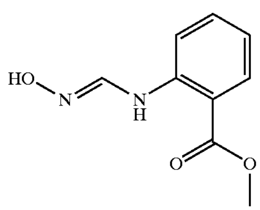 | | | 195 | 193 | | 0.24 | SiO2 (NH) | AcOEt | | |
| Comp. 159 | 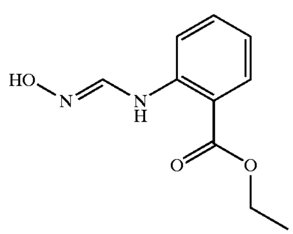 | | | 209 | 207 | | 0.26 | SiO2 (NH) | AcOEt | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 160 | 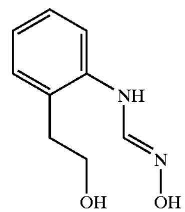 | | 181 | | 179 | | 0.21 | SiO2 (NH) | EtOAc:MeOH = 95:5 | | |
| Comp. 161 | 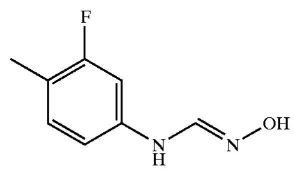 | 156.0–157.0 | | 169 | | 167 | 0.51 | SiO2 (NH) | EtOAc:MeOH = 95:5 | 88.6 | 13.4 |
| Comp. 162 | 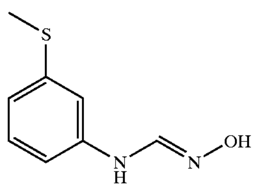 | | 183 | | 181 | | 0.49 | SiO2 (NH) | EtOAc:MeOH = 95:5 | 62.6 | |
| Comp. 163 | 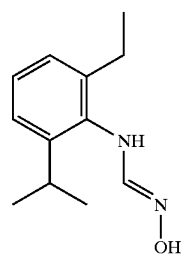 | | 207 | | | 205 | 0.61 | SiO2 (NH) | EtOAc:MeOH = 95:5 | 40.0 | |
| Comp. 164 | 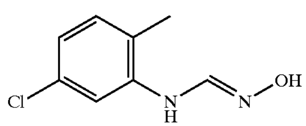 | | | 186 | | 184 | 0.55 | SiO2 (NH) | EtOAc:MeOH = 95:5 | 86.7 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 165 | 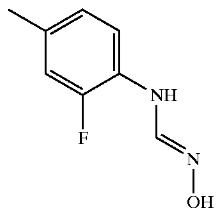 | | | 169 | | | 0.54 | SiO2 (NH) | EtOAc:MeOH = 95:5 | 105.7 | |
| Comp. 166 | 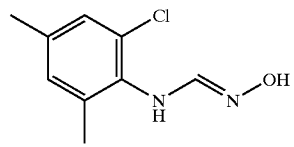 | | | 200 | | | 0.56 | SiO2 (NH) | EtOAc:MeOH = 95:5 | | |
| Comp. 167 | 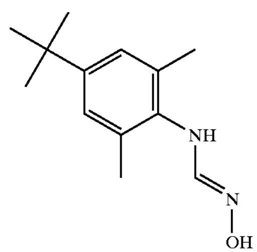 | | | 221 | | 219 | 0.58 | SiO2 (NH) | EtOAc:MeOH = 95:5 | | |
| Comp. 168 | 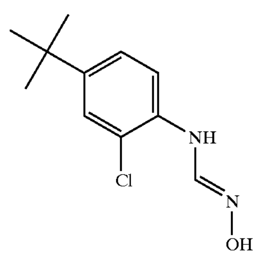 | | | 228 | 226 | | 0.57 | SiO2 (NH) | EtOAc:MeOH = 95:5 | 61.9 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 169 | 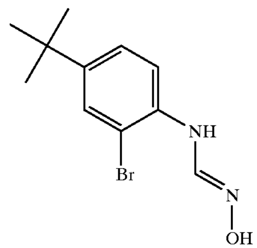 | | 272 | | 270 | | 0.57 | SiO2 (NH) | EtOAc:MeOH = 95:5 | 104.1 | |
| Comp. 170 | 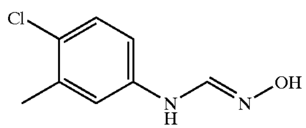 | | | 186 | | 184 | 0.50 | SiO2 (NH) | EtOAc:MeOH = 95:5 | 99.8 | |
| Comp. 171 | 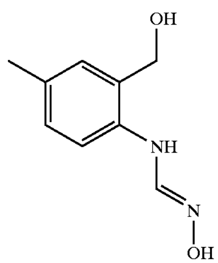 | | | 181 | | | 0.23 | SiO2 (NH) | EtOAc:MeOH = 95:5 | 54.1 | |
| Comp. 172 | 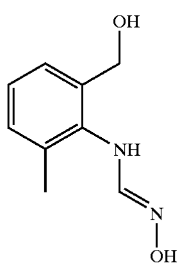 | | | 181 | | | 0.21 | SiO2 (NH) | EtOAc:MeOH = 95:5 | | |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 173 | 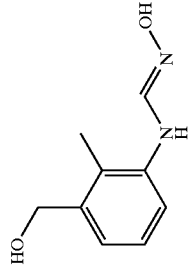 | | 181 | | | 179 | 0.30 | SiO2 (NH) | EtOAc:MeOH = 95:5 | | |
| Comp. 174 | 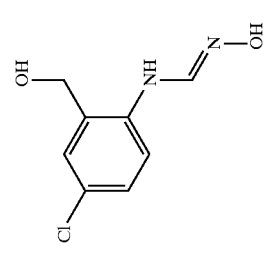 | | 202 | | | | 0.22 | SiO2 (NH) | EtOAc:MeOH = 95:5 | 62.4 | |
| Comp. 175 | 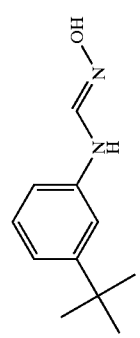 | | 193 | | | 191 | 0.56 | SiO2 (NH) | EtOAc:MeOH = 95:5 | 69.9 | |
| Comp. 176 | 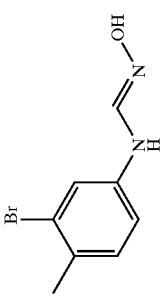 | | 230 | | | 228 | 0.51 | SiO2 (NH) | EtOAc:MeOH = 95:5 | 67.0 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 177 | Br-phenyl(ethyl)-NH-CH=N-OH | | 244 | | 242 | | 0.53 | SiO2 (NH) | EtOAc:MeOH = 95:5 | 85.4 | |
| Comp. 178 | isopropyl-methyl-phenyl-NH-CH=N-OH | 121.0–122.5 | 193 | | | 191 | 0.52 | SiO2 (NH) | EtOAc:MeOH = 95:5 | 91.4 | 9.0 |
| Comp. 179 | propyl-phenyl-NH-CH=N-OH | | 179 | | | 177 | 0.54 | SiO2 (NH) | EtOAc:MeOH = 95:5 | 63.5 | |
| Comp. 180 | 2,6-dichlorophenyl-NH-CH=N-OH | | 206 | | 204 | | 0.59 | SiO2 (NH) | EtOAc:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 181 | 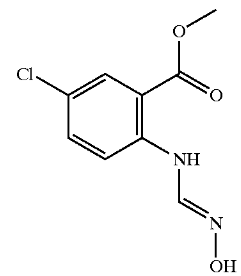 | | | | 227 | | 0.54 | SiO2 (NH) | EtOAc:MeOH = 95:5 | | |
| Comp. 182 | 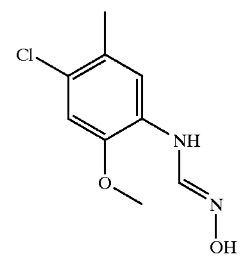 | | | 216 | 214 | | 0.56 | SiO2 (NH) | EtOAc:MeOH = 95:5 | 90.2 | |
| Comp. 183 | 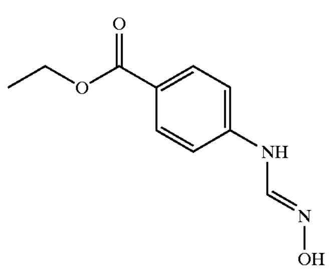 | | | 209 | 207 | | 0.50 | SiO2 (NH) | EtOAc:MeOH = 95:5 | 92.0 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 184 | 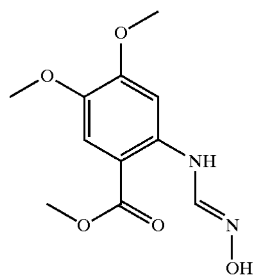 | | | 255 | 253 | | 0.48 | SiO2 (NH) | EtOAc:MeOH = 95:5 | | |
| Comp. 185 | 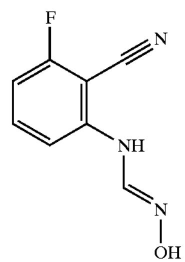 | | | 180 | 178 | | 0.36 | SiO2 (NH) | EtOAc:MeOH = 95:5 | | |
| Comp. 186 | 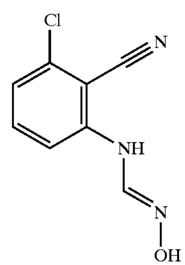 | | | 197 | 195 | | 0.29 | SiO2 (NH) | EtOAc:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 187 | 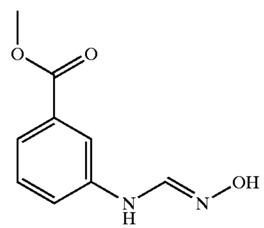 | | | 195 | 193 | | 0.50 | SiO2 (NH) | EtOAc:MeOH = 95:5 | | |
| Comp. 188 | 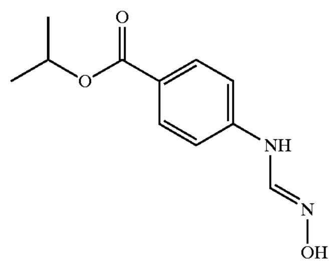 | | | 223 | 221 | | 0.50 | SiO2 (NH) | EtOAc:MeOH = 95:5 | 59.1 | |
| Comp. 189 | 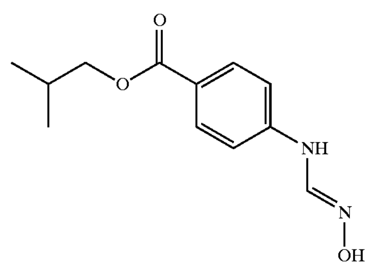 | | | 237 | 235 | | 0.50 | SiO2 (NH) | EtOAc:MeOH = 95:5 | 116.8 | |
| Comp. 190 | 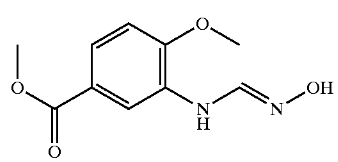 | | | 225 | 223 | | 0.51 | SiO2 (NH) | EtOAc:MeOH = 95:5 | 44.9 | |

TABLE 1-continued

| Comp. | Chemical Structure | mp. | M + H (ESI) | M + H (APCI) | M – H (ESI) | M – H (APCI) | Rf value | TLC* | Developing solvent | Inhibition rate (1 μM) | IC50 (nM) |
|---|---|---|---|---|---|---|---|---|---|---|---|
| Comp. 191 | (ethyl 4,5-dimethoxy-2-((hydroxyimino)methylamino)benzoate) | | 269 | | 267 | | 0.50 | SiO2 (NH) | EtOAc:MeOH = 95:5 | | |
| Comp. 192 | (methyl 4-chloro-2-((hydroxyimino)methylamino)benzoate) | | | 230 | 228 | | 0.56 | SiO2 (NH) | EtOAc:MeOH = 95:5 | | |
| Comp. 193 | (methyl 3-((hydroxyimino)methylamino)-4-methylbenzoate) | | 209 | | | 207 | 0.52 | SiO2 (NH) | EtOAc:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 194 | 3-chloro-4-cyanophenyl formamide oxime | | 197 | | | 195 | 0.44 | SiO2 (NH) | EtOAc:MeOH = 95:5 | 67.5 | |
| Comp. 195 | 2,6-dimethoxyphenyl formamide oxime | | 197 | | | | 0.51 | SiO2 (NH) | EtOAc:MeOH = 95:5 | | |
| Comp. 196 | 4,5-dimethoxy-2-cyanophenyl formamide oxime | | | | | 220 | 0.52 | SiO2 (NH) | EtOAc:MeOH = 95:5 | 46.9 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 197 | 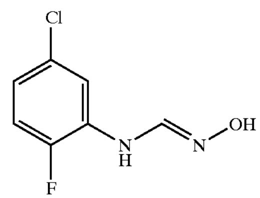 | | | 190 | 188 | | 0.57 | SiO2 (NH) | EtOAc:MeOH = 95:5 | | |
| Comp. 198 | 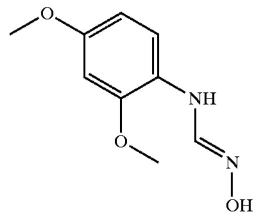 | | | 197 | | | 0.50 | SiO2 (NH) | EtOAc:MeOH = 95:5 | 81.8 | |
| Comp. 199 | 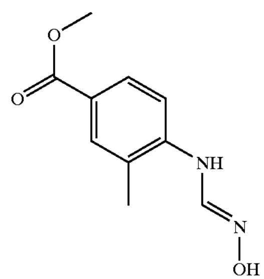 | | | 209 | 207 | | 0.50 | SiO2 (NH) | EtOAc:MeOH = 95:5 | 85.6 | |
| Comp. 200 | 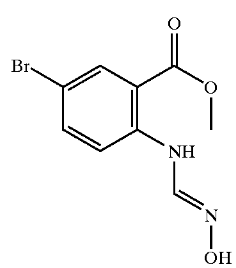 | | | 274 | 272 | | 0.50 | SiO2 (NH) | EtOAc:MeOH = 95:5 | 53.3 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 201 | 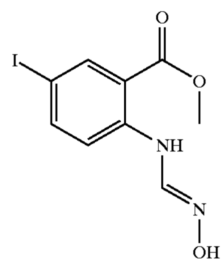 | | 321 | | 319 | | 0.50 | SiO2 (NH) | EtOAc:MeOH = 95:5 | 70.1 | |
| Comp. 202 | 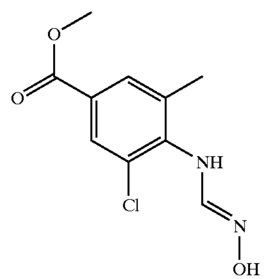 | | | 244 | | 242 | 0.53 | SiO2 (NH) | EtOAc:MeOH = 95:5 | 31.6 | |
| Comp. 203 | 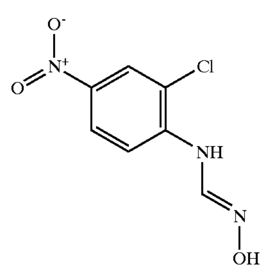 | | | 217 | | 215 | 0.45 | SiO2 (NH) | EtOAc:MeOH = 95:5 | 51.1 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 204 | 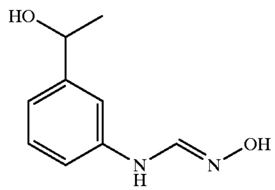 | | | 181 | | 179 | 0.30 | SiO2 (NH) | EtOAc:MeOH = 95:5 | | |
| Comp. 205 | 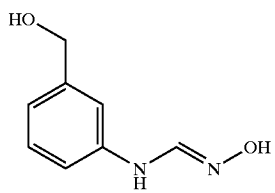 | | | 167 | | 165 | 0.25 | SiO2 (NH) | EtOAc:MeOH = 95:5 | | |
| Comp. 206 | 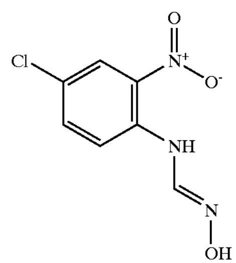 | | | 217 | | | 0.49 | SiO2 (NH) | EtOAc:MeOH = 95:5 | | |
| Comp. 207 | 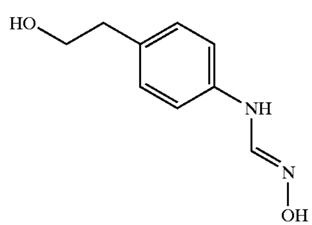 | 138.0–140.0 | | 181 | | 179 | 0.29 | SiO2 (NH) | EtOAc:MeOH = 95:5 | 90.7 | 11.6 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 208 | 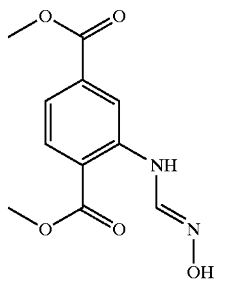 | | | 253 | 251 | | 0.53 | SiO2 (NH) | EtOAc:MeOH = 95:5 | | |
| Comp. 209 | 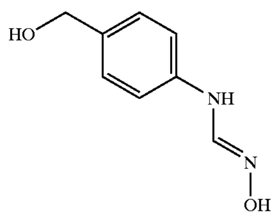 | 169.5–170.0 | | 167 | 165 | | 0.27 | SiO2 (NH) | EtOAc:MeOH = 95:5 | 102.2 | 151.6 |
| Comp. 210 | 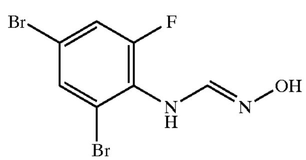 | | | 313 | 311 | | 0.58 | SiO2 (NH) | EtOAc:MeOH = 95:5 | 78 | |
| Comp. 211 | 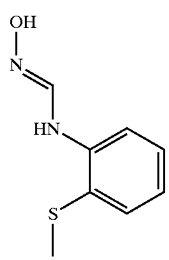 | | 183 | | 181 | | 0.35 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 212 | 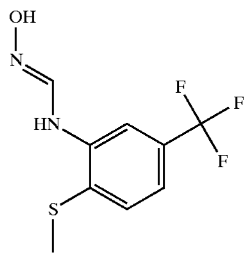 | | 251 | | 249 | | 0.35 | SiO2 | CHCl3:MeOH = 9:1 | | |
| Comp. 213 | 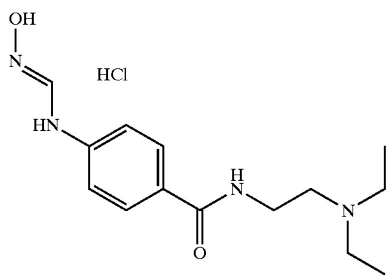 | | 279 | | | | 0.15 | SiO2 | CHCl3:MeOH = 9:1 | | |
| Comp. 214 | 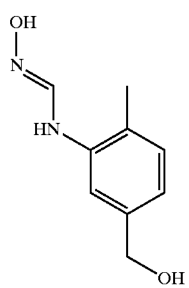 | | 181 | | 179 | | 0.12 | SiO2 | CHCl3:MeOH = 9:1 | 31.9 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 215 | (pentafluorophenyl-NH-CH=N-OH) | | | | 225 | | 0.25 | SiO2 | CHCl3:MeOH = 9:1 | 36.1 | |
| Comp. 216 | (2-methyl-3-fluorophenyl-NH-CH=N-OH) | | | | 167 | | 0.31 | SiO2 | CHCl3:MeOH = 9:1 | | |
| Comp. 217 | (4-dimethylaminophenyl-NH-CH=N-OH · 2HCl) | | 253 | | | | 0.4 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 218 | 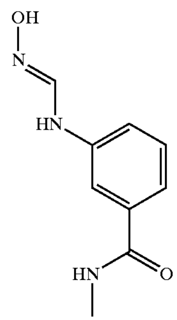 | | 194 | | | | 0.08 | SiO2 | CHCl3:MeOH = 9:1 | | |
| Comp. 219 | 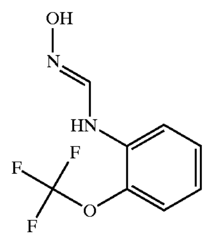 | | 221 | | 219 | | 0.38 | SiO2 | CHCl3:MeOH = 9:1 | | |
| Comp. 220 | 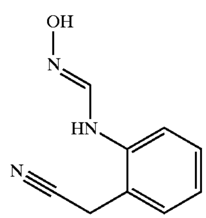 | | 176 | | 174 | | 0.28 | SiO2 | CHCl3:MeOH = 9:1 | | |
| Comp. 221 | 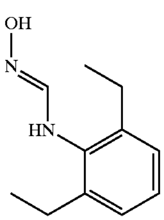 | | 193 | | 191 | | 0.35 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 222 | 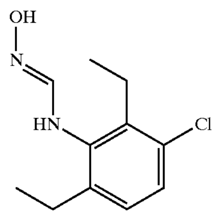 | | | | 225 | | 0.29 | SiO2 | CHCl3:MeOH = 9:1 | | |
| Comp. 223 | 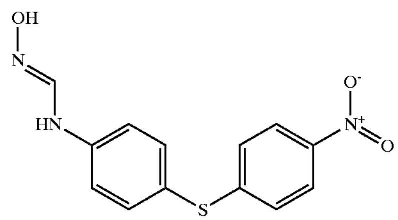 | | 290 | | 288 | | 0.34 | SiO2 | CHCl3:MeOH = 9:1 | 52.2 | |
| Comp. 224 | 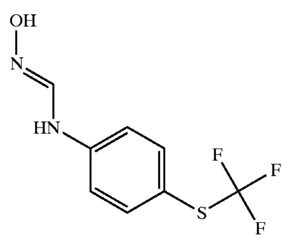 | | 237 | | 235 | | 0.31 | SiO2 | CHCl3:MeOH = 9:1 | 47.1 | |
| Comp. 225 | 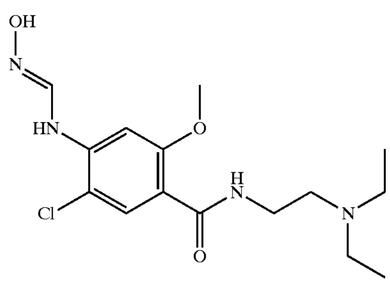 | | 343 | | 341 | | 0.05 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 226 | 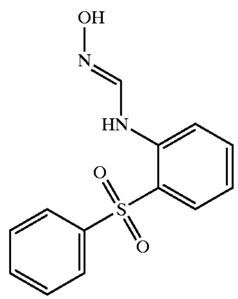 | | 277 | | 275 | | 0.37 | SiO2 | CHCl3:MeOH = 9:1 | | |
| Comp. 227 | 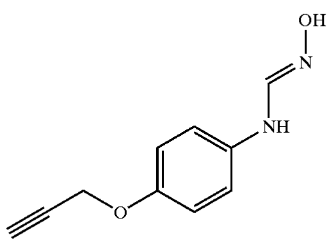 | 139.0–141.0 | 191 | | 189 | | 0.31 | SiO2 | AcOEt | 117.8 | 39.7 |
| Comp. 228 | 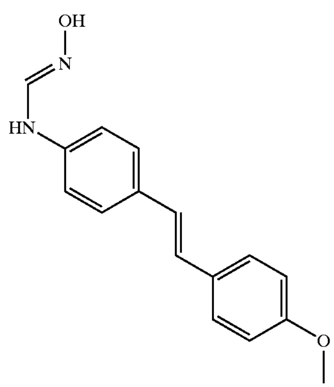 | | | | 267 | | 0.15 | SiO2 | EtOAc:hexane = 1:2 | 72.0 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 229 | 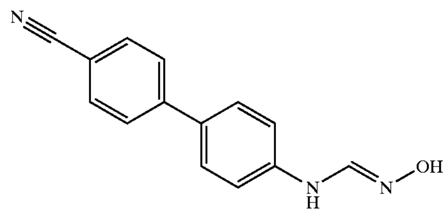 | 194.0–195.0 | 238 | | 236 | | 0.34 | SiO2 | CHCl3:MeOH = 9:1 | 99.3 | 16.0 |
| Comp. 230 | 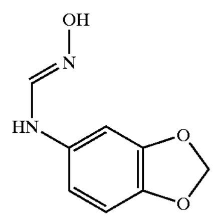 | 165.0–165.5 | 181 | | 179 | | 0.07 | SiO2 | EtOAc:hexane = 1:2 | | |
| Comp. 231 | 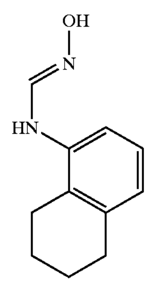 | 168.5–169.0 | 191 | | 189 | | 0.16 | SiO2 | EtOAc:hexane = 1:2 | 92.9 | 196.5 |
| Comp. 232 | 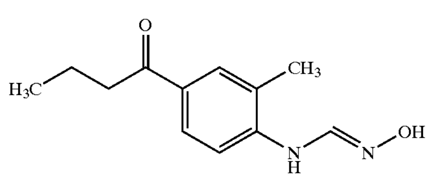 | 154.0–155.0 | | | | | | | | 86.0 | 6.6 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 233 | 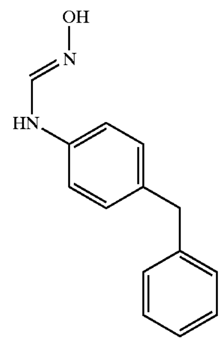 | 118.0–119.5 | 227 | | 225 | | 0.10 | SiO2 | EtOAc:hexane = 1:2 | 87.5 | 51.9 |
| Comp. 234 | 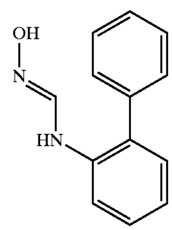 | 111.0–113.0 | 213 | | 211 | | 0.15 | SiO2 | EtOAc:hexane = 1:2 | 74.1 | |
| Comp. 235 | 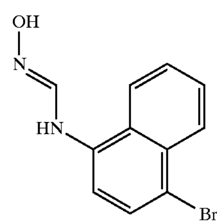 | 167.5–168.0 | | | 263 | | 0.13 | SiO2 | EtOAc:hexane = 1:2 | 77.8 | 5915.9 |
| Comp. 236 | 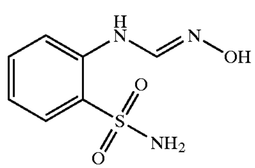 | 130.5–131.5 | | | | | | | | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 237 | 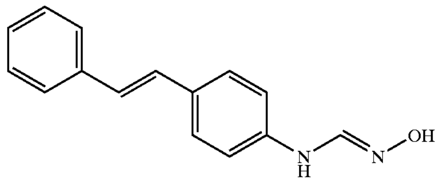 | 197.5–198.0 | | | 237 | | 0.17 | SiO2 | EtOAc:hexane = 1:2 | 96.6 | 26.2 |
| Comp. 238 | 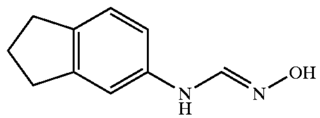 | 142.5–144.0 | 177 | | 175 | | 0.12 | SiO2 | EtOAc:hexane = 1:2 | 101.6 | 30.0 |
| Comp. 239 | 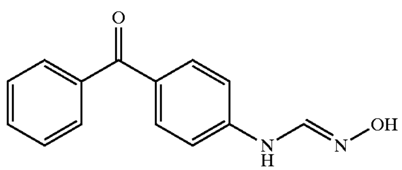 | 182.5–183.0 | | | | | | | | | 4078 |
| Comp. 240 | 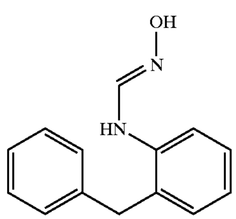 | | 227 | | 225 | | 0.15 | SiO2 | EtOAc:hexane = 1:2 | | |
| Comp. 241 | 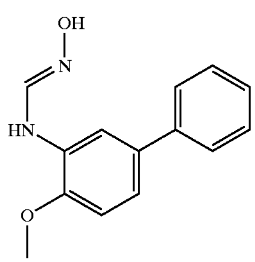 | | 243 | | | | 0.15 | SiO2 | EtOAc:hexane = 1:2 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 242 | 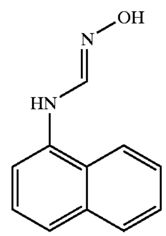 | | 187 | | 185 | | 0.13 | SiO2 | EtOAc:hexane = 1:2 | 50.6 | |
| Comp. 243 | 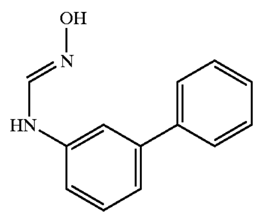 | | 213 | | 211 | | 0.11 | SiO2 | EtOAc:hexane = 1:2 | | |
| Comp. 244 | 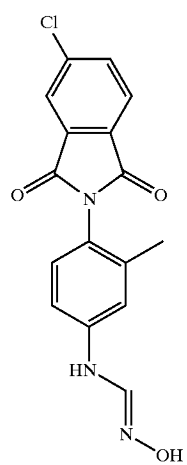 | | | 330 | 328 | 328 | 0.49 | SiO2 | CHCl3:MeOH = 95:5 | 32.7 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 245 | 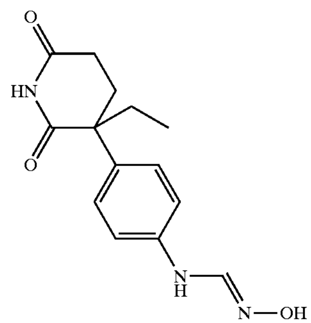 | | | 276 | 274 | 274 | 0.38 | SiO2 (NH) | AcOEt:EtOH = 90:10 | 55.4 | |
| Comp. 246 | 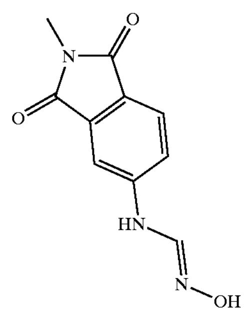 | | | 220 | 218 | 218 | 0.22 | SiO2 | CHCl3:MeOH = 95:5 | | |
| Comp. 247 | 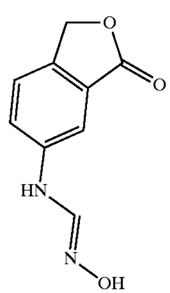 | | | 193 | 191 | 191 | 0.15 | SiO2 | CHCl3:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 248 | 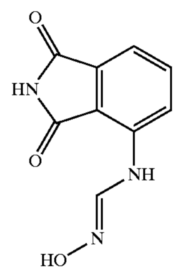 | | | 206 | 204 | | 0.64 | SiO2 | AcOEt:EtOH = 90:10 | | |
| Comp. 249 | 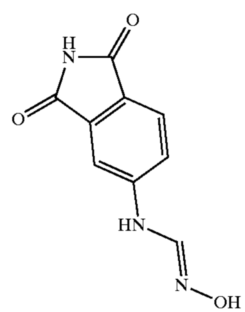 | | | 206 | 204 | | 0.6 | SiO2 | AcOEt:EtOH = 90:10 | | |
| Comp. 250 | 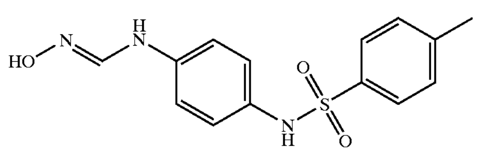 | | | 306 | 304 | 304 | 0.3 | SiO2 (NH) | AcOEt:EtOH = 90:10 | | |

TABLE 1-continued

| Comp. | Chemical Structure | mp. | M+H (ESI) | M+H (APCI) | M−H (ESI) | M−H (APCI) | Rf value | TLC* | Developing solvent | Inhibition rate (1 μM) | IC50 (nM) |
|---|---|---|---|---|---|---|---|---|---|---|---|
| Comp. 251 | 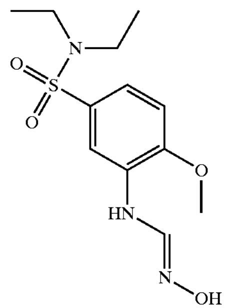 | | | 302 | 300 | 300 | 0.3 | SiO2 | CHCl3:MeOH = 95:5 | | |
| Comp. 252 | 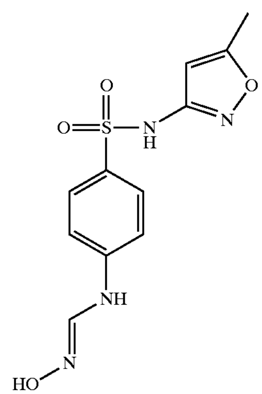 | | | | 295 | | 0.24 | SiO2 | CHCl3:MeOH = 95:5 | | |
| Comp. 253 | 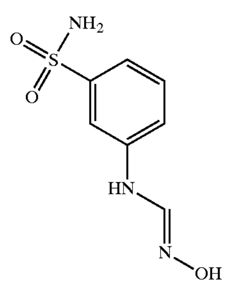 | | | 216 | 214 | 214 | 0.27 | SiO2 (NH) | AcOEt:EtOH = 90:10 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 254 | 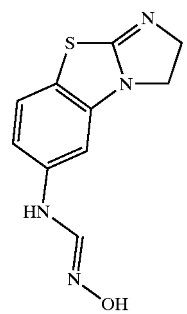 | | | | 233 | | 0.56 | SiO2 (NH) | AcOEt:EtOH = 90:10 | | |
| Comp. 255 | 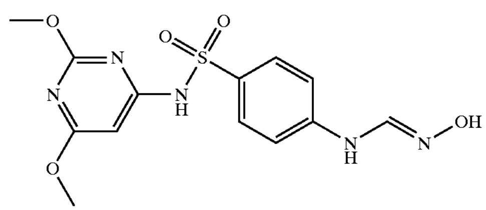 | | | 354 | 352 | 352 | 0.57 | SiO2 | AcOEt:EtOH = 90:10 | | |
| Comp. 256 | 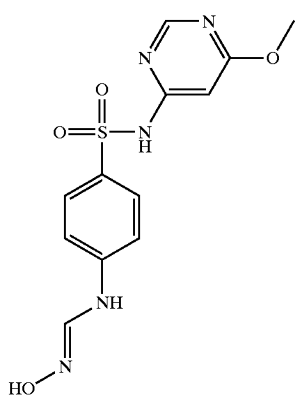 | | | | 321 | | 0.28 | SiO2 | CHCl3:MeOH = 95:5 | | |

TABLE 1-continued

| Comp. | Chemical Structure | mp. | M+H (ESI) | M+H (APCI) | M−H (ESI) | M−H (APCI) | Rf value | TLC* | Developing solvent | Inhibition rate (1 μM) | IC50 (nM) |
|---|---|---|---|---|---|---|---|---|---|---|---|
| Comp. 257 | 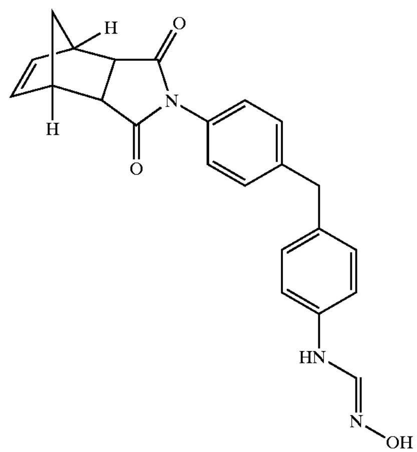 | | | 388 | 386 | 386 | 0.15 | SiO2 | CHCl3:MeOH = 95:5 | | |
| Comp. 258 | 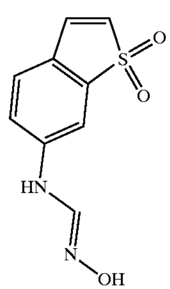 | | | 225 | 223 | 223 | 0.08 | SiO2 | CHCl3:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 259 | 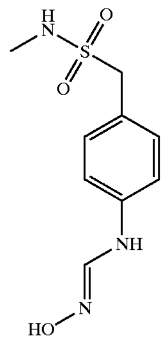 | | | 244 | 242 | | 0.33 | SiO2 (NH) | AcOEt:EtOH = 90:10 | 52.8 | |
| Comp. 260 | 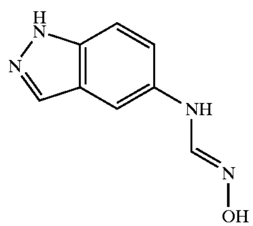 | | 177 | | 175 | 175 | 0.21 | SiO2 | CHCl3:MeOH = 95:5 | | |
| Comp. 261 | 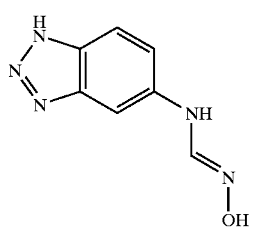 | | 178 | | 176 | 176 | 0.04 | SiO2 | CHCl3:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 262 | indole-NH-CH=N-OH structure | | | 176 | | 174 | 0.03 | SiO2 | CHCl3:MeOH = 95:5 | | |
| Comp. 263 | oxadiazole with bromo-methoxyphenyl and NH-CH=N-OH phenyl | | | 389 | 387 | 387 | 0.26 | SiO2 | CHCl3:MeOH = 95:5 | | |
| Comp. 264 | oxadiazole with methoxyphenyl and NH-CH=N-OH phenyl | | | 311 | 309 | 309 | 0.25 | SiO2 | CHCl3:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 265 | 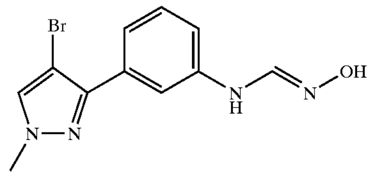 | | | 295 | | 293 | 0.19 | SiO2 | CHCl3:MeOH = 95:5 | | |
| Comp. 266 | 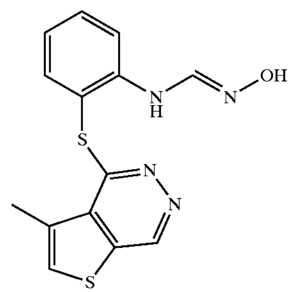 | | 317 | | 315 | | 0.24 | SiO2 | CHCl3:MeOH = 95:5 | | |
| Comp. 267 | 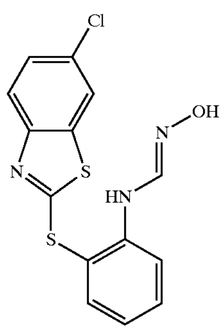 | | | | 334 | | 0.31 | SiO2 | CHCl3:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 268 | 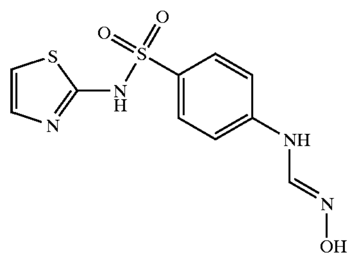 | | 299 | | 297 | 297 | 0.05 | SiO2 | CHCl3:MeOH = 95:5 | | |
| Comp. 269 | 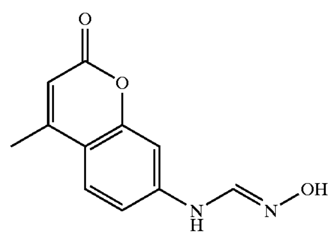 | | 219 | | 217 | 217 | 0.17 | SiO2 | CHCl3:MeOH = 95:5 | | |
| Comp. 270 | 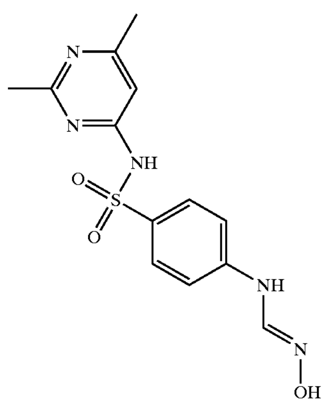 | | 322 | | 320 | 320 | 0.05 | SiO2 | CHCl3:MeOH = 95:5 | | |

TABLE 1-continued
| Comp. | Chemical Structure | mp. | M+H (ESI) | M+H (APCI) | M−H (ESI) | M−H (APCI) | Rf value | TLC* | Developing solvent | Inhibition rate (1 μM) | IC50 (nM) |
|---|---|---|---|---|---|---|---|---|---|---|---|
| Comp. 271 | 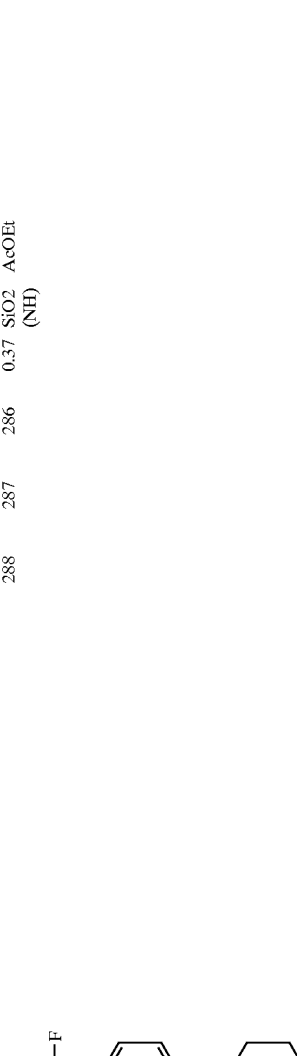 | | | 288 | 287 | 286 | 0.37 | SiO2 (NH) | AcOEt | | |
| Comp. 272 | 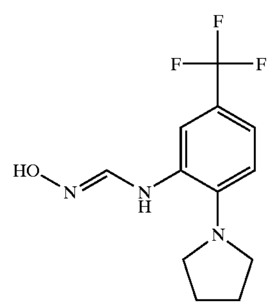 | | | 274 | 272 | 272 | 0.33 | SiO2 (NH) | AcOEt | | |
| Comp. 273 | 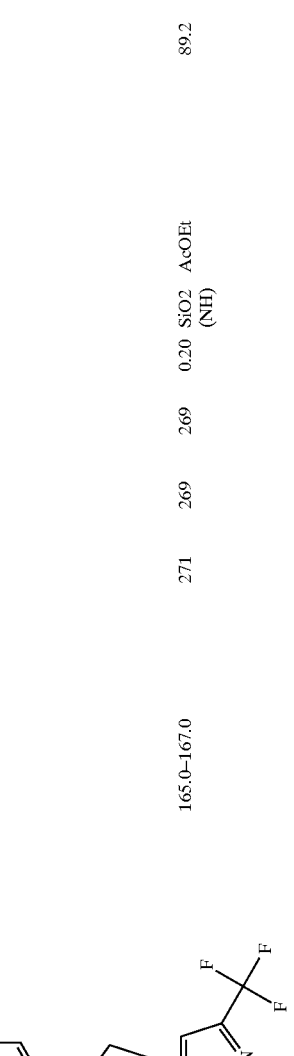 | 165.0–167.0 | | 271 | 269 | 269 | 0.20 | SiO2 (NH) | AcOEt | 89.2 | 96.8 |
| Comp. 274 | 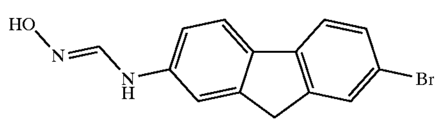 | | | 303 | 301 | 301 | 0.16 | SiO2 (NH) | AcOEt | 94.5 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 275 | 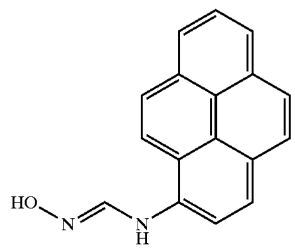 | | 261 | | 259 | 259 | 0.16 | SiO2 (NH) | AcOEt | | |
| Comp. 276 | 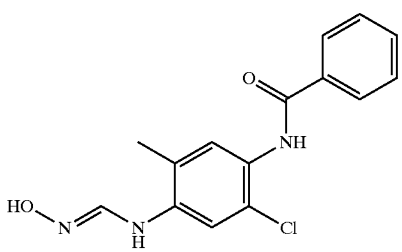 | 207.0–207.5 | 304 | | 302 | 302 | 0.16 | SiO2 (NH) | AcOEt | 71.8 | 55.9 |
| Comp. 277 | 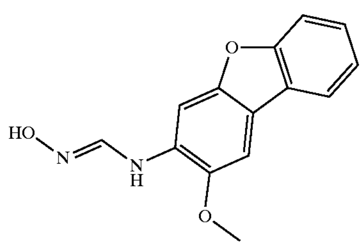 | | 257 | | 255 | 255 | 0.22 | SiO2 (NH) | AcOEt | 76.4 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 278 | 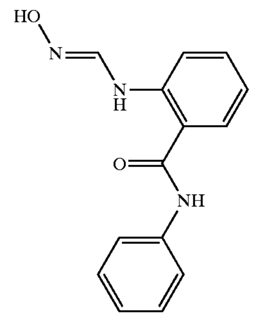 | | 256 | | 254 | | 0.15 | SiO2 (NH) | AcOEt | 65.3 | |
| Comp. 279 | 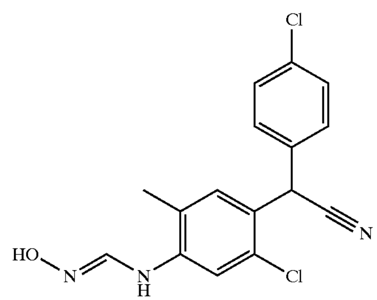 | | 334 | | 332 | 332 | 0.21 | SiO2 (NH) | AcOEt | 42.8 | |
| Comp. 280 | 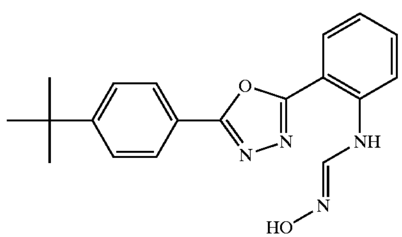 | | 337 | | 335 | 335 | 0.21 | SiO2 (NH) | AcOEt | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 281 | 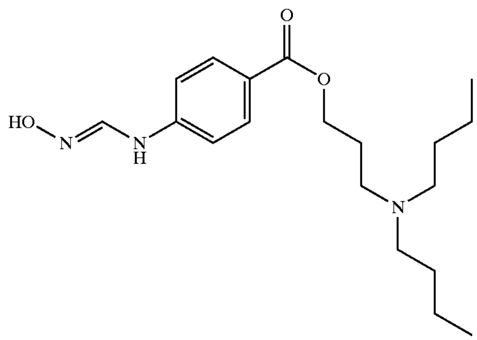 | | 350 | | 348 | 348 | 0.21 | SiO2 (NH) | AcOEt | 50.9 | |
| Comp. 282 | 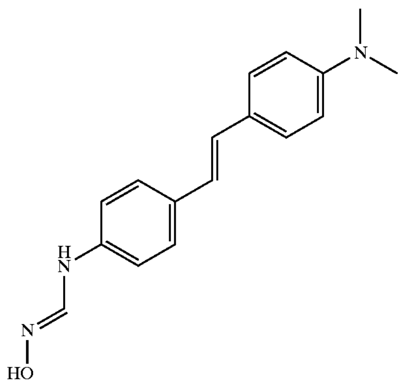 | | 282 | | | 280 | 0.17 | SiO2 (NH) | AcOEt | 122.9 | |
| Comp. 283 | 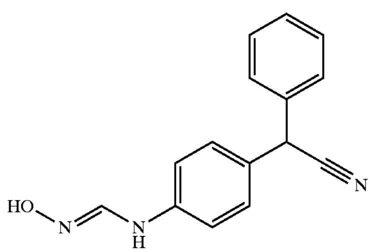 | | 252 | | 250 | 250 | 0.16 | SiO2 (NH) | AcOEt | 62.6 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 284 | 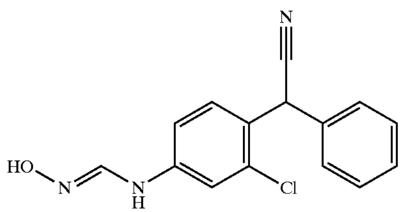 | | 286 | | 284 | 284 | 0.18 | SiO2 (NH) | AcOEt | | |
| Comp. 285 | 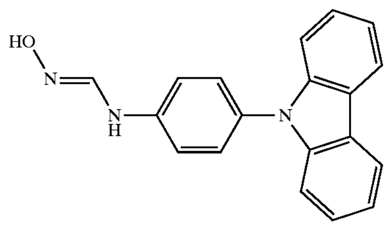 | | 302 | | 300 | 300 | 0.16 | SiO2 (NH) | AcOEt | | |
| Comp. 286 | 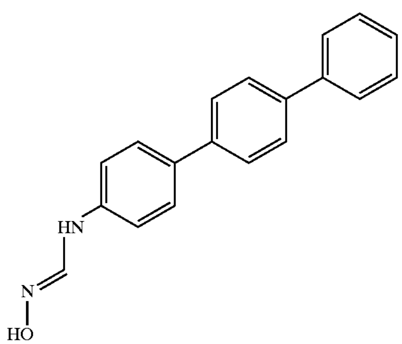 | | 289 | | 287 | 287 | 0.16 | SiO2 (NH) | AcOEt | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 287 | ethyl 2-methyl-5-[4-(hydroxyiminomethylamino)phenyl]furan-3-carboxylate | | 289 | | 287 | 287 | 0.17 | SiO2 (NH) | AcOEt | | |
| Comp. 288 | 2-methyl-5-(hydroxyiminomethylamino)benzothiazole | | 208 | | 206 | 206 | 0.14 | SiO2 (NH) | AcOEt | | |
| Comp. 289 | 4-[4-(hydroxyiminomethylamino)phenyl]-1,2,3-thiadiazole | | 221 | | 219 | 219 | 0.13 | SiO2 (NH) | AcOEt | | |
| Comp. 290 | 4-cyano-1-(hydroxyiminomethylamino)naphthalene | | 212 | | 210 | 210 | 0.42 | SiO2 (NH) | EtOAc:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 291 | 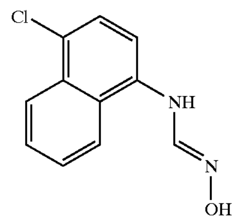 | | 222 | | 220 | 220 | 0.48 | SiO2 (NH) | EtOAc:MeOH = 95:5 | | |
| Comp. 292 | 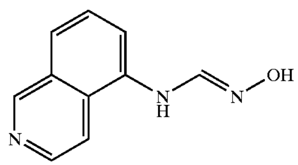 | | | 188 | 186 | 186 | 0.36 | SiO2 (NH) | EtOAc:MeOH = 95:5 | | |
| Comp. 293 | 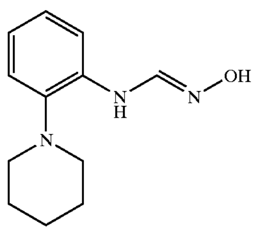 | | 220 | | 218 | 218 | 0.59 | SiO2 (NH) | EtOAc:MeOH = 95:5 | | |
| Comp. 294 | 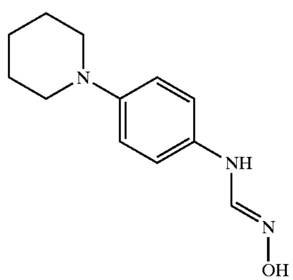 | 162.0–162.5 | 220 | | 218 | 218 | 0.47 | SiO2 (NH) | EtOAc:MeOH = 95:5 | 103.2 | 4.9 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 295 | 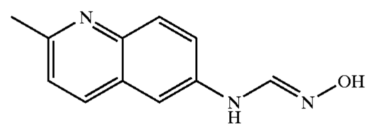 | | | 202 | | 200 | 0.37 | SiO2 (NH) | EtOAc:MeOH = 95:5 | 73.8 | |
| Comp. 296 | 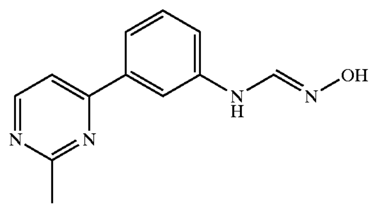 | | | 229 | | 227 | 0.41 | SiO2 (NH) | EtOAc:MeOH = 95:5 | | |
| Comp. 297 | 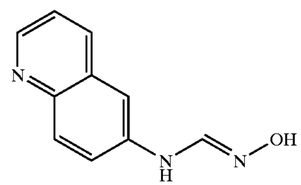 | | | 188 | | 186 | 0.35 | SiO2 (NH) | EtOAc:MeOH = 95:5 | 71.1 | |
| Comp. 298 | 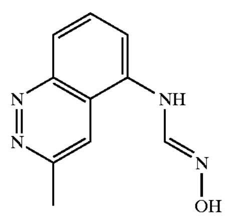 | | | 203 | | 201 | 0.33 | SiO2 (NH) | EtOAc:MeOH = 95:5 | | |
| Comp. 299 | 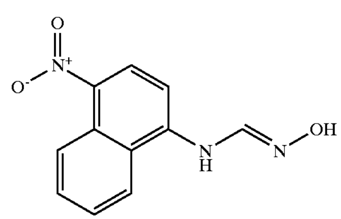 | | | 232 | 230 | 230 | 0.40 | SiO2 (NH) | EtOAc:MeOH = 95:5 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 300 | 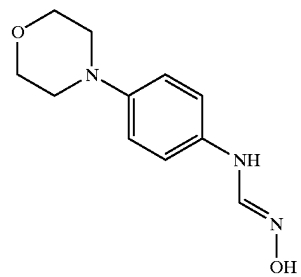 | 182.0–182.5 | | 222 | | 220 | 0.44 | SiO2 (NH) | EtOAc:MeOH = 95:5 | 96.3 | 5.7 |
| Comp. 301 | 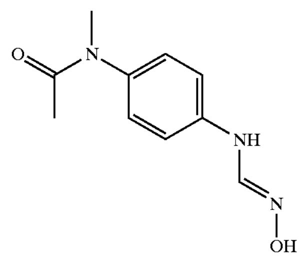 | | | 208 | | 208 | 0.36 | SiO2 (NH) | EtOAc:MeOH = 95:5 | 62.1 | |
| Comp. 302 | 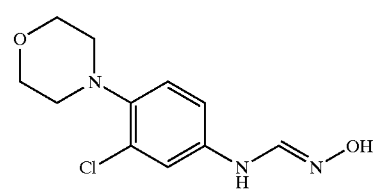 | 177.5–178.0 | | 257 | | 255 | 0.47 | SiO2 (NH) | EtOAc:MeOH = 95:5 | 96.5 | 1.9 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 303 | 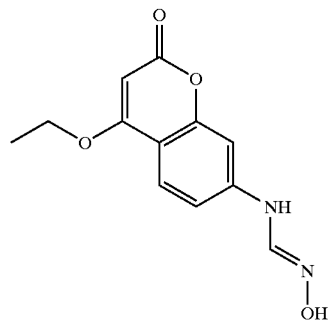 | | 249 | | 247 | 247 | 0.35 | SiO2 (NH) | EtOAc:MeOH = 95:5 | | |
| Comp. 304 | 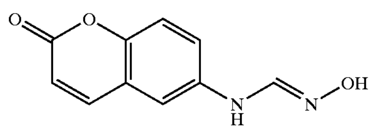 | | | 205 | 203 | | 0.33 | SiO2 (NH) | EtOAc:MeOH = 95:5 | 68.5 | |
| Comp. 305 | 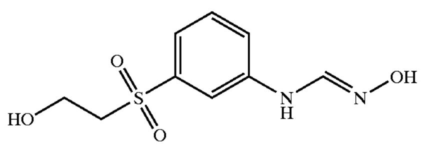 | | | 245 | | 243 | 0.14 | SiO2 (NH) | EtOAc:MeOH = 95:5 | | |
| Comp. 306 | 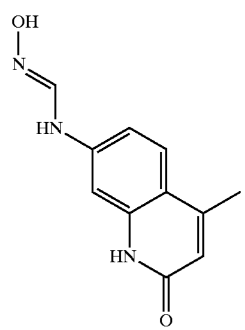 | | | | 216 | | 0.10 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 307 | HCl | | 201 | | | | 0.40 | SiO2 | CHCl3:MeOH = 9:1 | | |
| Comp. 308 | 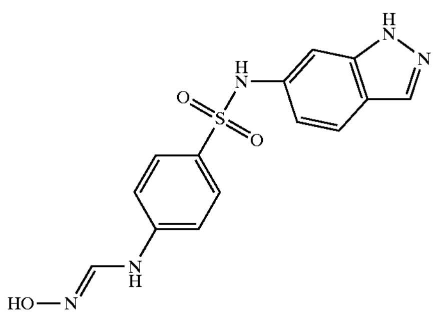 | | 332 | | 330 | | 0.08 | SiO2 | CHCl3:MeOH = 9:1 | | |
| Comp. 309 | 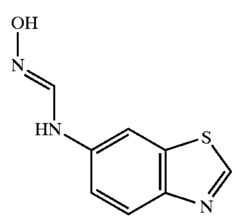 | | 194 | | | | 0.17 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 310 | 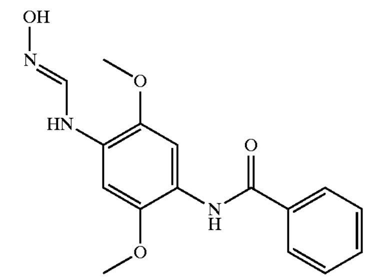 | | 316 | | 314 | | 0.25 | SiO2 | CHCl3:MeOH = 9:1 | | |
| Comp. 311 | 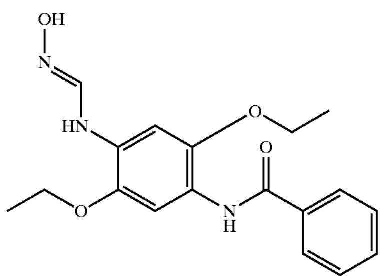 | | 344 | | 342 | | 0.25 | SiO2 | CHCl3:MeOH = 9:1 | | |
| Comp. 312 | 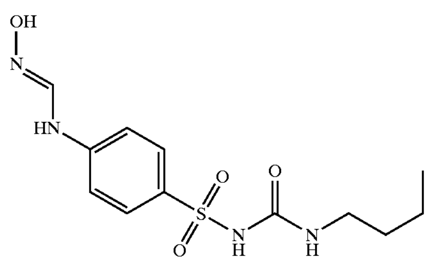 | | 315 | | | | 0.15 | SiO2 | CHCl3:MeOH = 9:1 | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 313 | 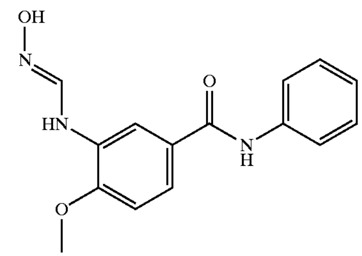 | | 286 | | 284 | | 0.25 | SiO2 | CHCl3:MeOH = 9:1 | | |
| Comp. 314 | 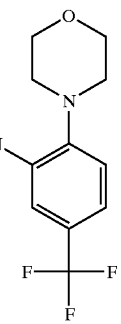 | | 290 | | | | 0.38 | SiO2 | CHCl3:MeOH = 9:1 | | |
| Comp. 315 | 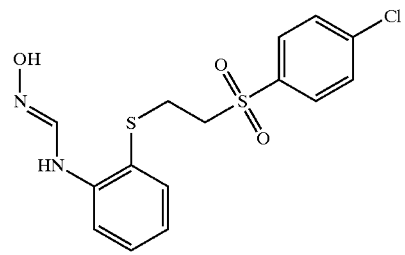 | | 371 | | 369 | | 0.48 | SiO2 | CHCl3:MeOH = 9:1 | 50.7 | |
| Comp. 316 | 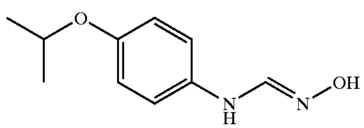 | 144.0–146.0 | 195 | | 193 | | 0.09 | SiO2 | Hexane:AcOEt = 2:1 | 97.9 | 24.0 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 317 | 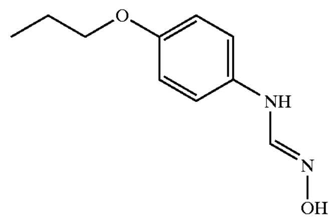 | 132.0–133.0 | | 195 | | | 0.51 | SiO2 (NH) | EtOAc:MeOH = 95:5 | 93.8 | 3.5 |
| Comp. 318 | 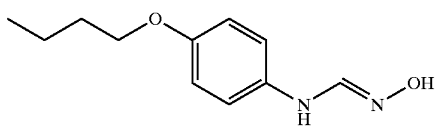 | 136.5–137.5 | 209 | | 207 | | 0.09 | SiO2 | Hexane:AcOEt = 2:1 | | 9.9 |
| Comp. 319 | 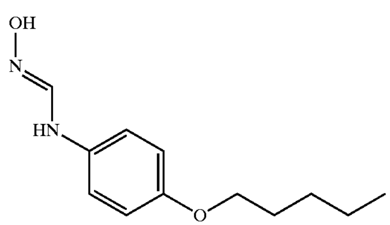 | 126.0–127.0 | 223 | | 221 | | 0.13 | SiO2 | Hexane:AcOEt = 2:1 | 99.9 | 3.8 |
| Comp. 320 | 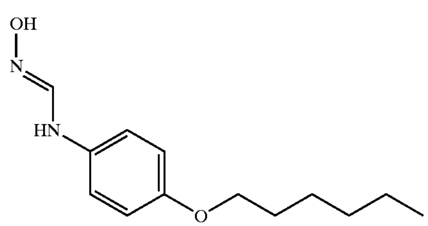 | 125.0–126.0 | 237 | | 235 | | 0.11 | SiO2 | Hexane:AcOEt = 2:1 | 92.5 | 1.3 |

TABLE 1-continued

| Comp. | Chemical Structure | mp. | M+H (ESI) | M+H (APCI) | M-H (ESI) | M-H (APCI) | Rf value | TLC* | Developing solvent | Inhibition rate (1 μM) | IC50 (nM) |
|---|---|---|---|---|---|---|---|---|---|---|---|
| Comp. 321 | *(structure)* | 121–122.5 | 251 | | 249 | | 0.36 | SiO2 (NH) | AcOEt | 99.9 | 3.7 |
| Comp. 322 | *(structure)* | | 265 | | 263 | | 0.36 | SiO2 (NH) | AcOEt | 117.5 | |
| Comp. 323 | *(structure)* | 128.0–130.0 | 279 | | 277 | | 0.12 | SiO2 | Hexane:AcOEt = 2:1 | | 25.9 |
| Comp. 324 | *(structure)* | 148.5–149.5 | 223 | | 221 | | 0.22 | SiO2 | AcOEt | 99 | 3.7 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 325 | 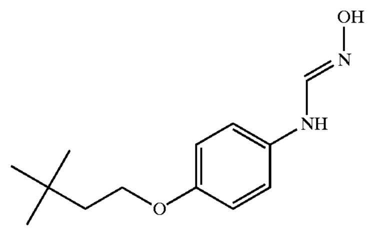 | 123.0–125.0 | 237 | | 235 | | 0.23 | SiO2 | AcOEt | 106 | 2.6 |
| Comp. 326 | 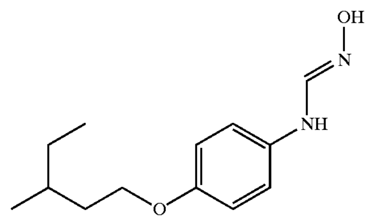 | | 237 | | 235 | | 0.35 | SiO2 (NH) | AcOEt | 110.8 | |
| Comp. 327 | 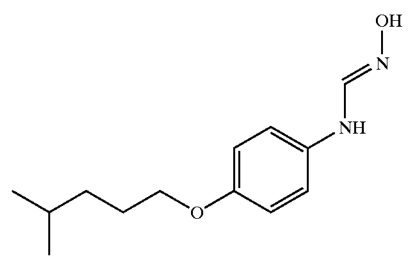 | | | 237 | 235 | | 0.35 | SiO2 (NH) | AcOEt | 110.1 | |
| Comp. 328 | 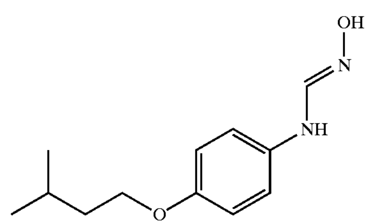 | | 233 | | 221 | | 0.33 | SiO2 (NH) | AcOEt | 121.4 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 329 | 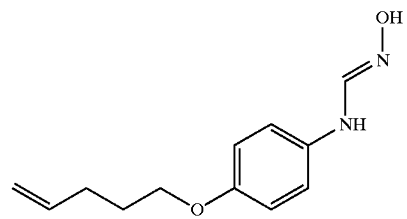 | 127.0–128.0 | | 221 | 219 | | 0.33 | SiO2 (NH) | AcOEt | 121.1 | 0.7 |
| Comp. 330 | 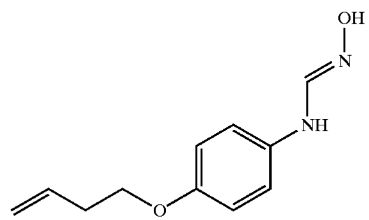 | 122.0–124.0 | 207 | | 205 | | 0.33 | SiO2 (NH) | AcOEt | 118.8 | 2.4 |
| Comp. 331 | 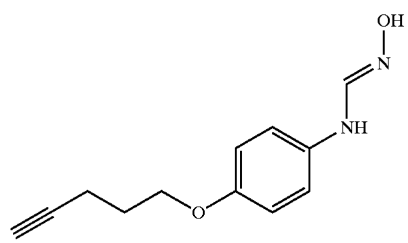 | 139.0–139.5 | | 219 | 217 | | 0.31 | SiO2 (NH) | AcOEt | 118.8 | 3.2 |
| Comp. 332 | 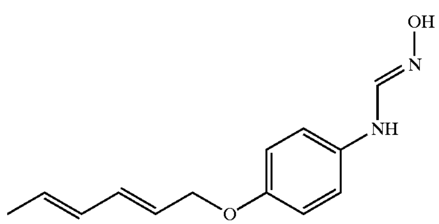 | 169.5–170.0 | 233 | | 231 | | 0.31 | SiO2 (NH) | AcOEt | 110.6 | 2.1 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 333 | ![structure] | 171.5–172.0 | 205 | | 203 | | 0.3 | SiO2 (NH) | AcOEt | 119.3 | 2.2 |
| Comp. 334 | ![structure] | 125.0–126.0 | 221 | | | | 0.23 | SiO2 | AcOEt | 105 | 3.2 |
| Comp. 335 | ![structure] | 139.0–141.0 | 205 | | | | 0.23 | SiO2 | AcOEt | 110 | 1.4 |
| Comp. 336 | ![structure] | 142.5–146.0 | 207 | | 205 | | 0.31 | SiO2 (NH) | AcOEt | 117.6 | 3.2 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 337 | 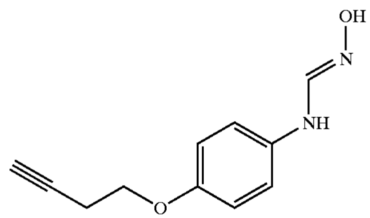 | 135.0–136.5 | 219 | | 217 | | 0.31 | SiO2 (NH) | AcOEt | 119.4 | 2.1 |
| Comp. 338 | 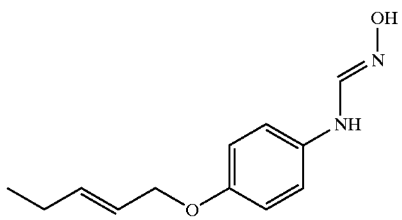 | 100.0–102.0 | 221 | | | 219 | 0.33 | SiO2 (NH) | AcOEt | 119.8 | 0.9 |
| Comp. 339 | 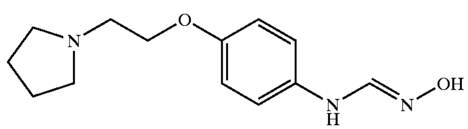 | 113.5–114.5 | 250 | | 248 | | 0.11 | SiO2 | AcOEt | 88 | 124.2 |
| Comp. 340 | 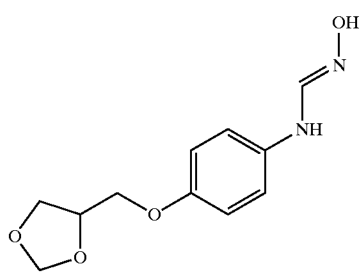 | 157.5–158 | | | | | | | | 97.4 | 3.0 |
| Comp. 341 | 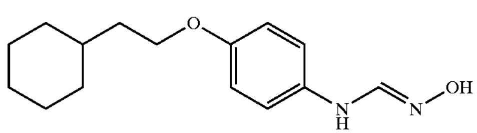 | 129.5–133 | 263 | | 261 | | 0.23 | SiO2 | AcOEt | 104 | 1.2 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 342 | quinoline-CH2-O-C6H4-NH-CH=N-OH | 174.5–175.5 | | | | | | | | 98.5 | 5.3 |
| Comp. 343 | Ph-CH2-O-C6H4-NH-CH=N-OH | 166.5–167.0 | 244 | | | | | | | 84.5 | 3.3 |
| Comp. 344 | 4-pyridyl-CH2-O-C6H4-NH-CH=N-OH | 180–180.5 | 244 | | | | 0.12 | SiO2 | AcOEt | 107 | 37.5 |
| Comp. 345 | 2-pyridyl-CH2-O-C6H4-NH-CH=N-OH | 159.5–161 | | | | | 0.14 | SiO2 | AcOEt | 101 | 23.1 |
| Comp. 346 | MeO-CH2CH2-O-C6H4-NH-CH=N-OH | 104.0–107.0 | | | | | | | | 106.2 | 8.9 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 347 | 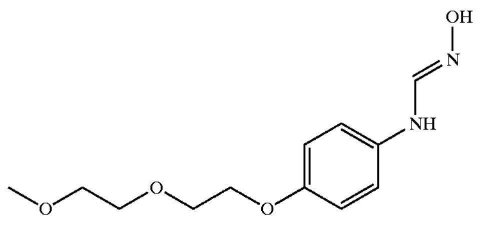 | 80.5–81.5 | 255 | | 253 | | 0.18 | SiO2 | AcOEt | 105 | 3.7 |
| Comp. 348 | 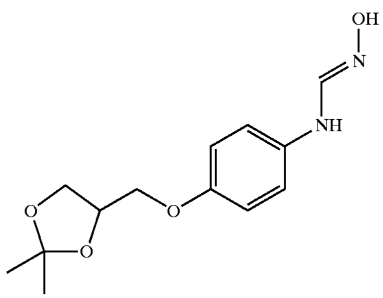 | 128.5–129.5 | 267 | | 265 | | 0.21 | SiO2 | AcOEt | 103 | 3.4 |
| Comp. 349 | 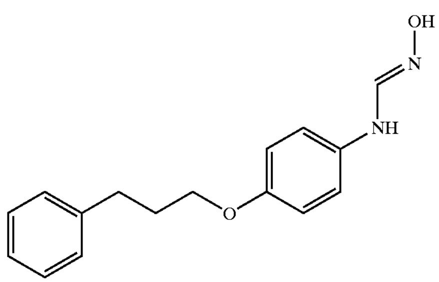 | 152.5–153.0 | 271 | | 269 | | 0.21 | SiO2 | AcOEt | 100 | 1.6 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 350 | 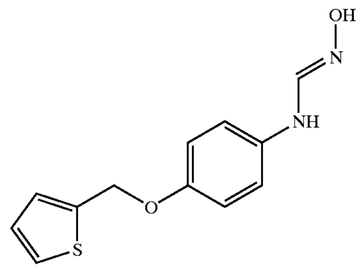 | 168.0–168.5 | 249 | | | | 0.19 | SiO2 | AcOEt | 91 | 1.4 |
| Comp. 351 | 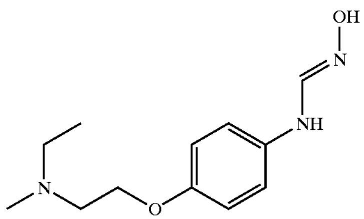 | | 252 | | 250 | | 0.18 | SiO2 | AcOEt | 89 | |
| Comp. 352 | 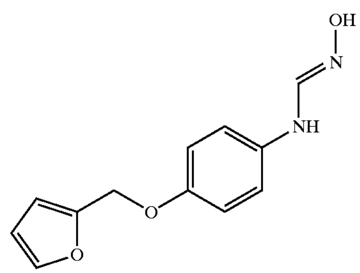 | 158.5–159.5 | 233 | | | | 0.2 | SiO2 | AcOEt | 97 | 4.6 |
| Comp. 353 | 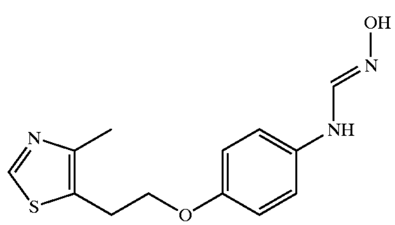 | 158.0–160.0 | 278 | | 276 | | 0.14 | SiO2 | AcOEt | 105 | 3.7 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 354 | *structure* | 113.0–114.0 | 239 | | 237 | | 0.23 | SiO2 | AcOEt | 106 | 3.0 |
| Comp. 355 | *structure* | 141.0–142.0 | 266 | | 264 | | 0.14 | SiO2 | AcOEt | 107 | 5.9 |
| Comp. 356 | *structure* | 141.0–142.5 | 207 | | | | 0.23 | SiO2 | AcOEt | 102 | 2.6 |
| Comp. 357 | *structure* | | 264 | | 262 | | 0.16 | SiO2 | AcOEt | 98 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 358 | (structure) | 138.0–139.5 | 272 | | 270 | | 0.14 | SiO2 | AcOEt | 103 | 3.1 |
| Comp. 359 | (structure) | 132.5–134.5 | 290 | | 288 | | 0.2 | SiO2 | AcOEt | 102 | 1.4 |
| Comp. 360 | (structure) | | 279 | | 277 | | 0.22 | SiO2 | AcOEt | | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 361 | 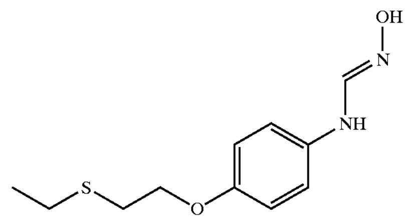 | 104.0–106.0 | 241 | | 239 | | 0.22 | SiO2 | AcOEt | 106 | 2.1 |
| Comp. 362 | 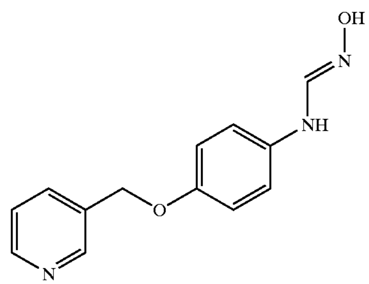 | 156.0–157.0 | 244 | | | | 0.11 | SiO2 | AcOEt | 106 | 2.1 |
| Comp. 363 | 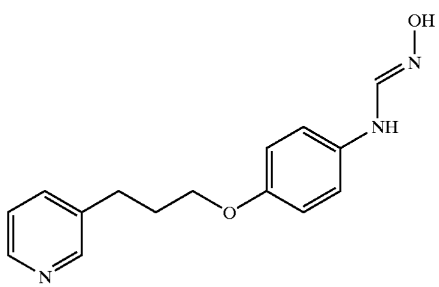 | 154.0–155.0 | 272 | | 270 | | 0.11 | SiO2 | AcOEt | 105 | 0.78 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 364 | 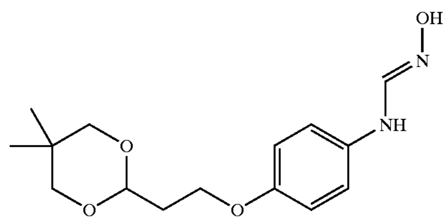 | 136.5–137.5 | 295 | | 293 | | 0.21 | SiO2 | AcOEt | 104 | 2.0 |
| Comp. 365 | 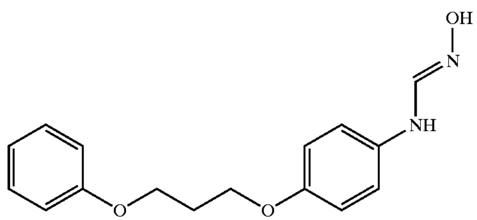 | 143.5–145.0 | 287 | | 285 | | 0.19 | SiO2 | AcOEt | 105 | 1.4 |
| Comp. 366 | 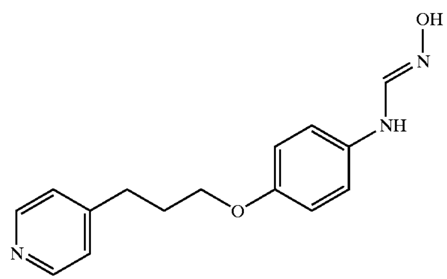 | 188.0–189.0 | 272 | | | | 0.09 | SiO2 | AcOEt | 105 | 1.2 |
| Comp. 367 | 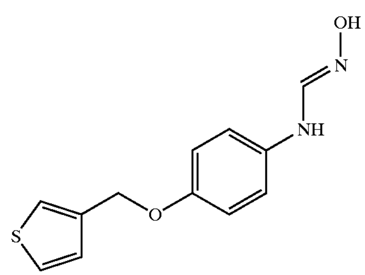 | 165.0–166.0 | 249 | | | | 0.18 | SiO2 | AcOEt | 103 | 2.1 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 368 | HO-N=CH-NH-C6H4-O-CH2-(3-furyl) | 165.5–166.0 | 233 | | | | 0.19 | SiO2 | AcOEt | 96 | 2.5 |
| Comp. 369 | HO-N=CH-NH-C6H4-O-CH2-(6-methylpyridin-2-yl) | 148.5–149.0 | 258 | | | | 0.16 | SiO2 | AcOEt | 105 | 3.1 |
| Comp. 370 | HO-N=CH-NH-C6H4-O-CH2-cycloheptyl | | 263 | 263 | 261 | 261 | 0.33 | SiO2 (NH) | AcOEt | 113.7 | |

TABLE 1-continued

| Comp. | Chemical Structure | mp. | M+H (ESI) | M+H (APCI) | M−H (ESI) | M−H (APCI) | Rf value | TLC* | Developing solvent | Inhibition rate (1 μM) | IC50 (nM) |
|---|---|---|---|---|---|---|---|---|---|---|---|
| Comp. 371 | 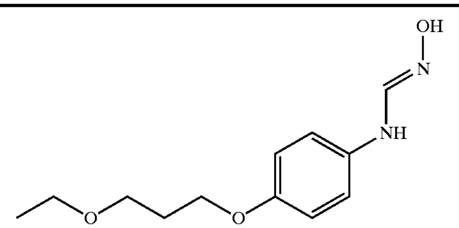 | 93.0–94.0 | 239 | 239 | 237 | 237 | 0.31 | SiO2 (NH) | AcOEt | 110.4 | 0.9 |
| Comp. 372 | 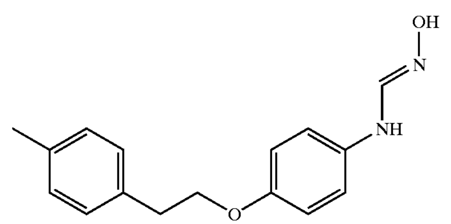 | | | 271 | 269 | 269 | 0.31 | SiO2 (NH) | AcOEt | 100.5 | |
| Comp. 373 | 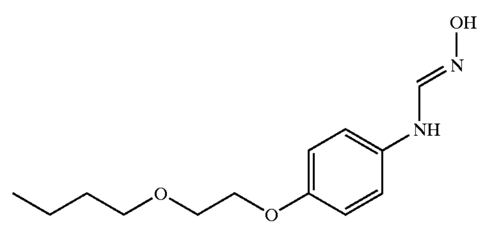 | 97.0–99.0 | | 253 | 251 | 251 | 0.31 | SiO2 (NH) | AcOEt | 115.3 | 0.8 |
| Comp. 374 | 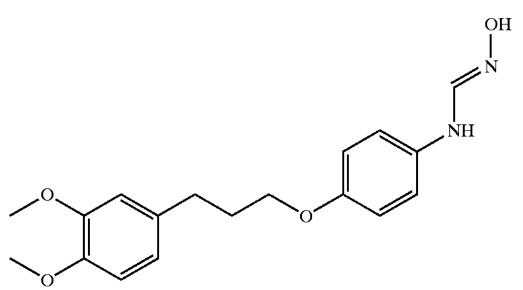 | | 331 | 331 | 329 | 329 | 0.3 | SiO2 (NH) | AcOEt | 119.1 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 375 | 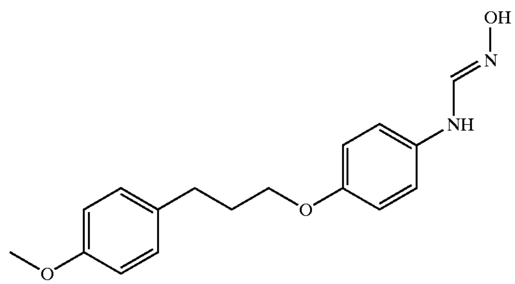 | | 301 | | 299 | 299 | 0.3 | SiO2 (NH) | AcOEt | 117.7 | |
| Comp. 376 | 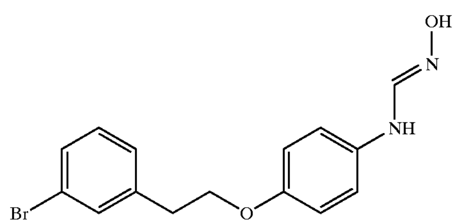 | | 336 | | 333 | 334 | 0.3 | SiO2 (NH) | AcOEt | 114.9 | |
| Comp. 377 | 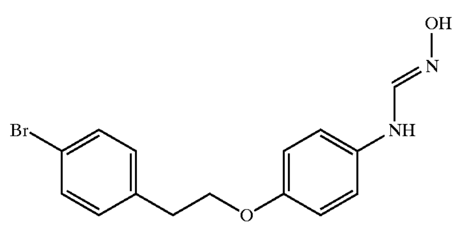 | | 336 | | 334 | 334 | 0.3 | SiO2 (NH) | AcOEt | 107.4 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 378 | 4-[(ethoxycarbonylpentyloxy)phenyl]-N-hydroxyformamidine | | 295 | 293 | 293 | 293 | 0.3 | SiO2 (NH) | AcOEt | 102.4 | |
| Comp. 379 | 4-[2-(2-methoxyphenyl)ethoxy]phenyl-N-hydroxyformamidine | | 287 | 285 | 285 | 285 | 0.27 | SiO2 (NH) | AcOEt | 105.4 | |
| Comp. 380 | geranyloxyphenyl-N-hydroxyformamidine | | 291 | 289 | 289 | 289 | 0.26 | SiO2 (NH) | AcOEt | 118.9 | |
| Comp. 381 | 4-(4-phenylbutoxy)phenyl-N-hydroxyformamidine | | 285 | 283 | 283 | 283 | 0.27 | SiO2 (NH) | AcOEt | 116.0 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 382 | 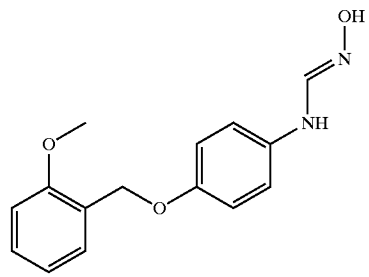 | 153.0–153.5 | | 273 | | | 0.26 | SiO2 (NH) | AcOEt | 122.5 | 3.1 |
| Comp. 383 | 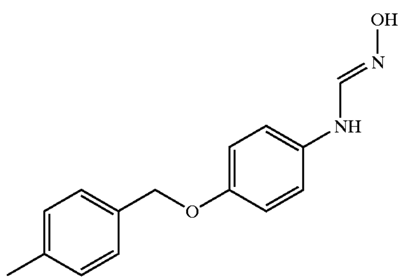 | | | 257 | 255 | 255 | 0.26 | SiO2 (NH) | AcOEt | 116.2 | |
| Comp. 384 | 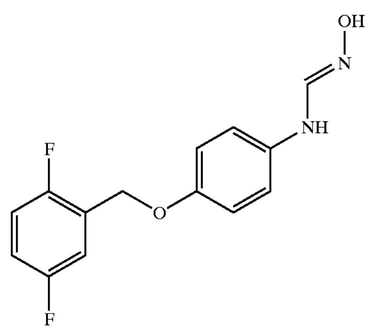 | 167.0–167.5 | | 279 | 277 | | 0.27 | SiO2 (NH) | AcOEt | 117.3 | 2.8 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 385 | 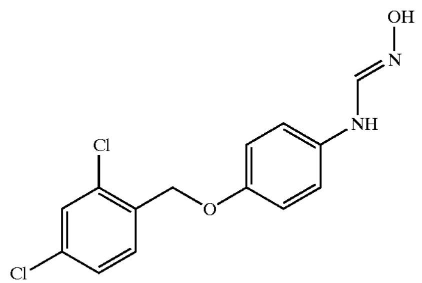 | | | 312 | | 310 | 0.27 | SiO2 (NH) | AcOEt | 109.0 | |
| Comp. 386 | 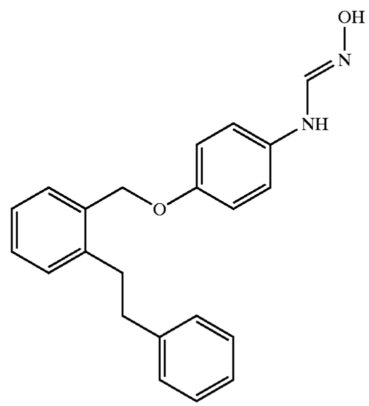 | | | 347 | 345 | | 0.27 | SiO2 (NH) | AcOEt | 105.2 | |
| Comp. 387 | 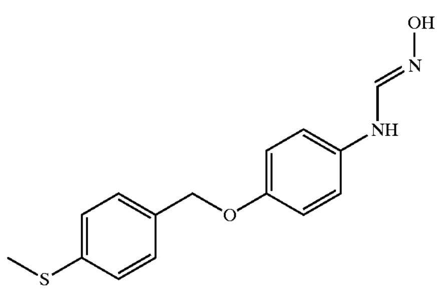 | 163.0–164.0 | 289 | 289 | | | 0.27 | SiO2 (NH) | AcOEt | 97.8 | 0.9 |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 388 | 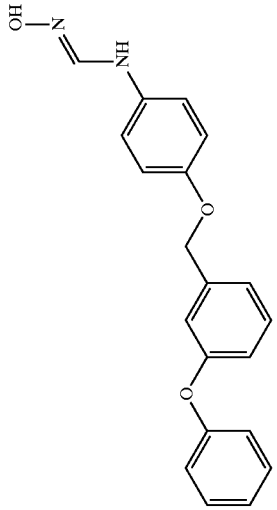 | | 335 | | 333 | 333 | 0.27 | SiO2 (NH) | AcOEt | 96.2 | |
| Comp. 389 | 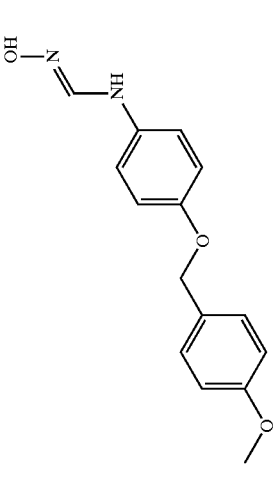 | 167.0–167.5 | 273 | | 271 | 271 | 0.31 | SiO2 (NH) | AcOEt | 105.5 | 1.6 |
| Comp. 390 | 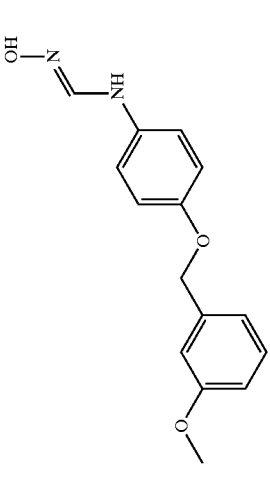 | 152.5–153.5 | 273 | | 271 | 271 | 0.31 | SiO2 (NH) | AcOEt | 112.8 | 2.7 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 391 | *structure* | 161.5–162.0 | 257 | 257 | 255 | 255 | 0.31 | SiO2 (NH) | AcOEt | 113.4 | 2.4 |
| Comp. 392 | *structure* | 165.5–166.0 | 261 | 261 | 259 | | 0.31 | SiO2 (NH) | AcOEt | 109.6 | 2.4 |
| Comp. 393 | *structure* | 143.0–146.0 | 268 | 268 | 266 | 266 | 0.26 | SiO2 (NH) | AcOEt | 124.3 | 1.1 |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 394 | 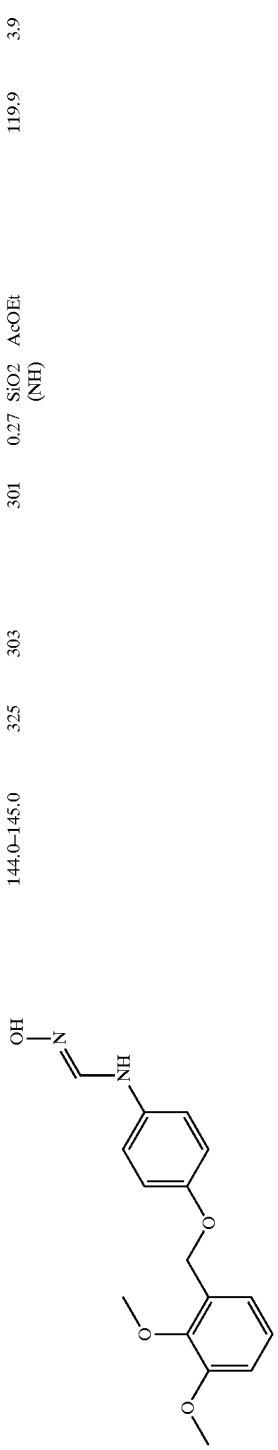 | 144.0–145.0 | 325 | 303 | | 301 | 0.27 | SiO2 (NH) | AcOEt | 119.9 | 3.9 |
| Comp. 395 | 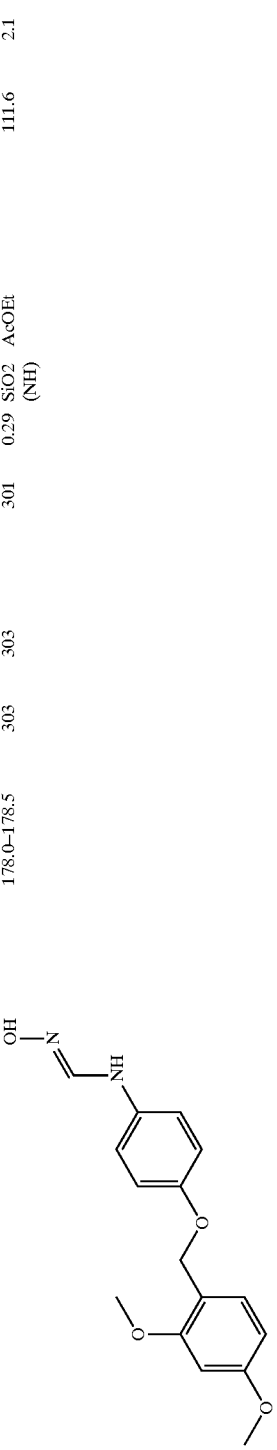 | 178.0–178.5 | 303 | 303 | 321 | 301 | 0.29 | SiO2 (NH) | AcOEt | 111.6 | 2.1 |
| Comp. 396 | 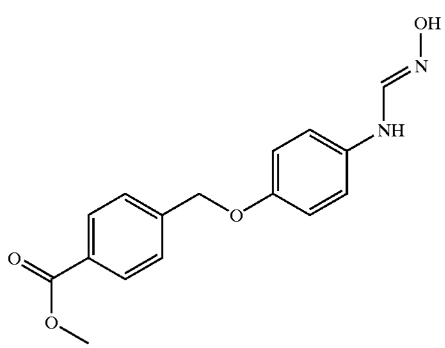 | | 323 | 301 | | 299 | 0.29 | SiO2 (NH) | AcOEt | 102.7 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 397 | 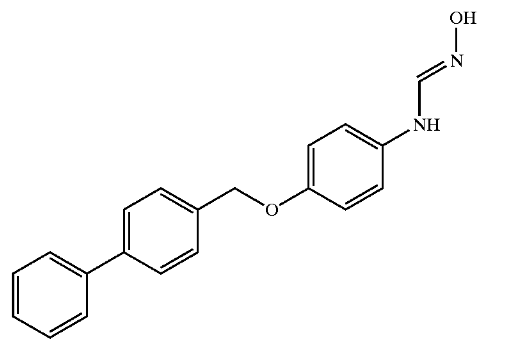 | | | 319 | | | 0.29 | SiO2 (NH) | AcOEt | 99.3 | |
| Comp. 398 | 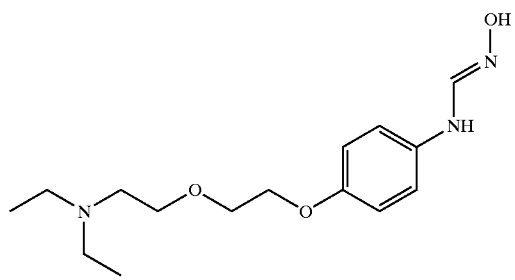 | | 296 | 296 | 294 | 294 | 0.29 | SiO2 (NH) | AcOEt | 95.2 | 2.4 |
| Comp. 399 | 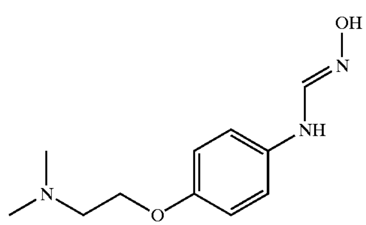 | 118–120 | 224 | 224 | 222 | 222 | 0.31 | SiO2 (NH) | AcOEt | 102.3 | 98 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 400 | 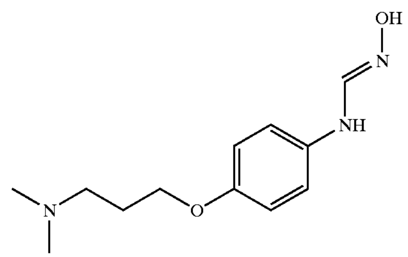 | 115.0–117.0 | 238 | 238 | | 236 | 0.29 | SiO2 (NH) | AcOEt | 116.9 | |
| Comp. 401 | 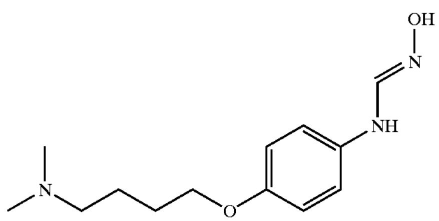 | 100.0–102.0 | 252 | 252 | 250 | 250 | 0.29 | SiO2 (NH) | AcOEt | 117.4 | |
| Comp. 402 | 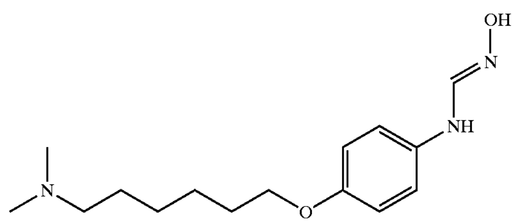 | 95.0–96.0 | 280 | 280 | 278 | 278 | 0.29 | SiO2 (NH) | AcOEt | 118.8 | 18.7 |
| Comp. 403 | 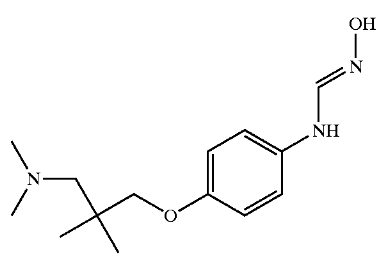 | 101.5–102.0 | 266 | 266 | 264 | 264 | 0.32 | SiO2 (NH) | AcOEt | 118.3 | 28.5 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 404 | 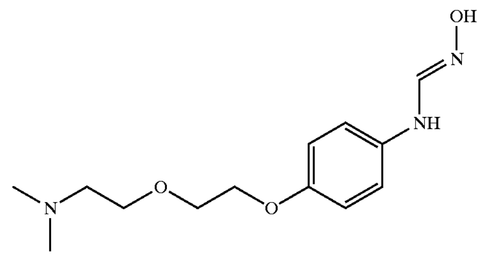 | 57.5–59.0 | 268 | 268 | 266 | 266 | 0.29 | SiO2 (NH) | AcOEt | 114.9 | 115.6 |
| Comp. 405 | 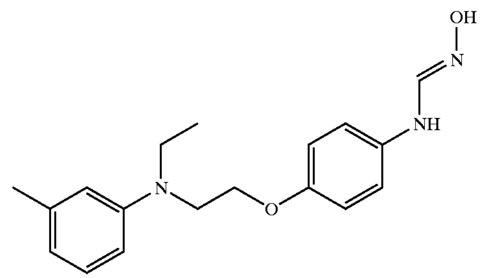 | | 314 | 314 | 312 | 312 | 0.33 | SiO2 (NH) | AcOEt | 116.0 | |
| Comp. 406 | 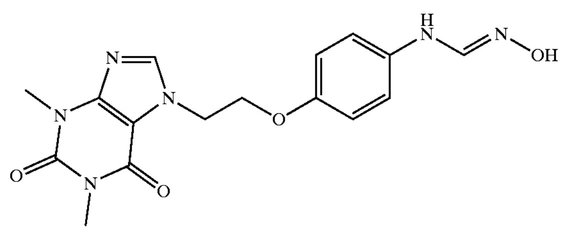 | | | 359 | 357 | 357 | 0.29 | SiO2 (NH) | AcOEt | 73.7 | |
| Comp. 407 | 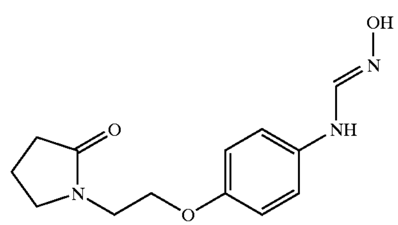 | 127.5–129.5 | 264 | 264 | 262 | 262 | 0.29 | SiO2 (NH) | AcOEt | 94.3 | 4.9 |

TABLE 1-continued

| Comp. | Chemical Structure | mp. | M + H (ESI) | M + H (APCI) | M – H (ESI) | M – H (APCI) | Rf value | TLC* | Developing solvent | Inhibition rate (1 μM) | IC50 (nM) |
|---|---|---|---|---|---|---|---|---|---|---|---|
| Comp. 408 | 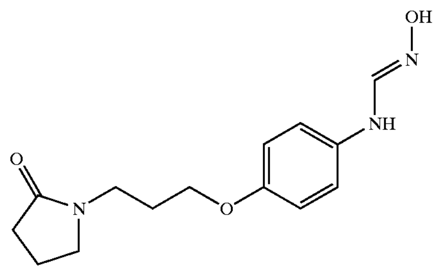 | 177.0–177.5 | 278 | 278 | 276 | 276 | 0.29 | SiO2 (NH) | AcOEt | 103.0 | 4.2 |
| Comp. 409 | 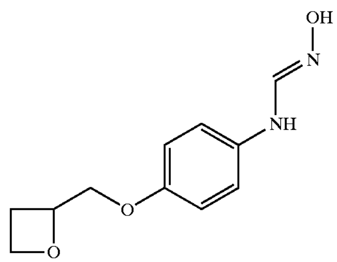 | 145.0–146.0 | 223 | 223 | 221 | 221 | 0.31 | SiO2 (NH) | AcOEt | 113.2 | 6.7 |
| Comp. 410 | 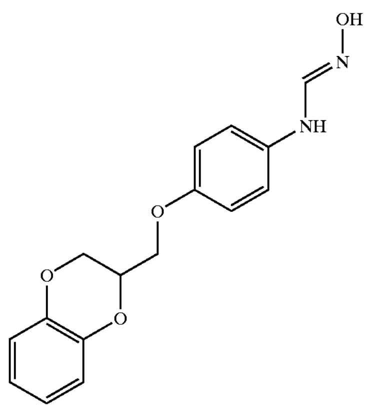 | 153.0–155.0 | 301 | 301 | 299 | 299 | 0.31 | SiO2 (NH) | AcOEt | 117.3 | 1.0 |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 411 | 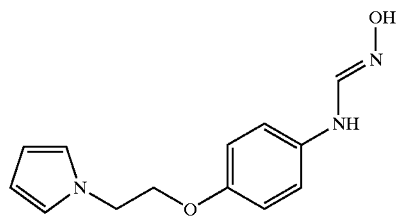 | 150.5–151.5 | 246 | 246 | 244 | 244 | 0.31 | SiO2 (NH) | AcOEt | 122.4 | 3.1 |
| Comp. 412 | 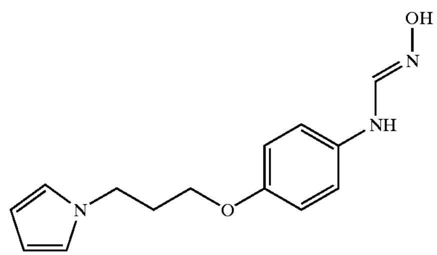 | 130.0–130.5 | 260 | 260 | 258 | 258 | 0.32 | SiO2 (NH) | AcOEt | 119.4 | 1.5 |
| Comp. 413 | 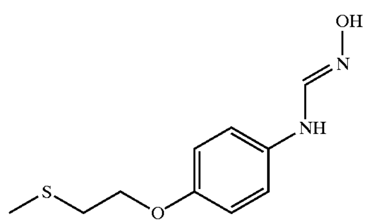 | 112.0–113.0 | | 227 | 225 | 225 | 0.32 | SiO2 (NH) | AcOEt | 120.2 | 2.3 |
| Comp. 414 | 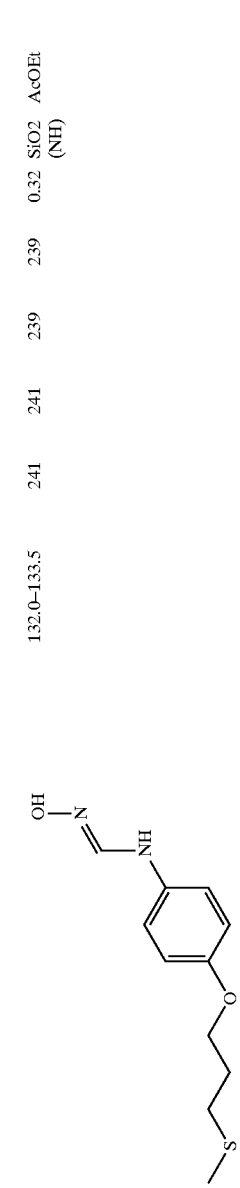 | 132.0–133.5 | 241 | 241 | 239 | 239 | 0.32 | SiO2 (NH) | AcOEt | 113.2 | 1.0 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 415 | 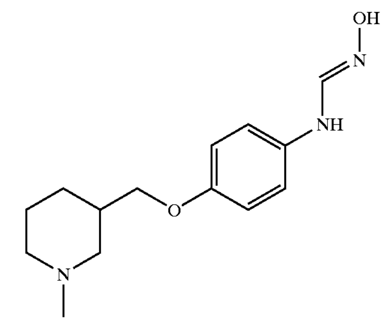 | 114–117 | 264 | 264 | 262 | 262 | 0.31 | SiO2 (NH) | AcOEt | 103.7 | 17.6 |
| Comp. 416 | 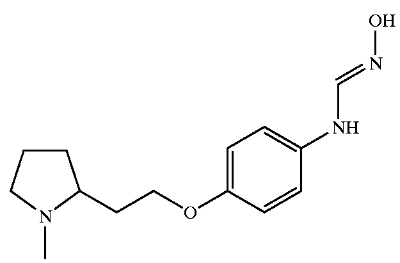 | 99.5–102.5 | 264 | 264 | 262 | 262 | 0.31 | SiO2 (NH) | AcOEt | 85.8 | 16.3 |
| Comp. 417 | 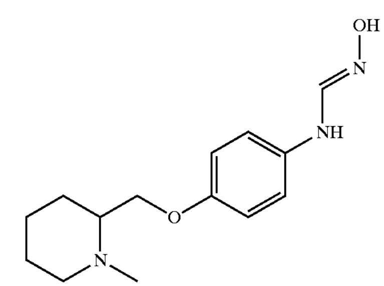 | 146.5–148 | 264 | 264 | 262 | 262 | 0.33 | SiO2 (NH) | AcOEt | 102.8 | 90.0 |

TABLE 1-continued

| Comp. | Chemical Structure | mp. | M+H (ESI) | M+H (APCI) | M−H (ESI) | M−H (APCI) | Rf value | TLC* | Developing solvent | Inhibition rate (1 μM) | IC50 (nM) |
|---|---|---|---|---|---|---|---|---|---|---|---|
| Comp. 418 | 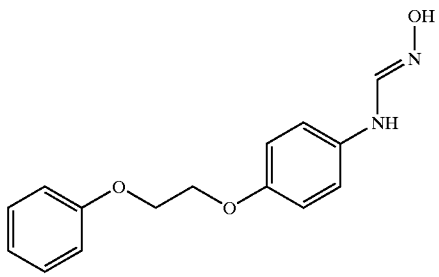 | | | 273 | 271 | 271 | 0.33 | SiO2 (NH) | AcOEt | 120.4 | |
| Comp. 419 | 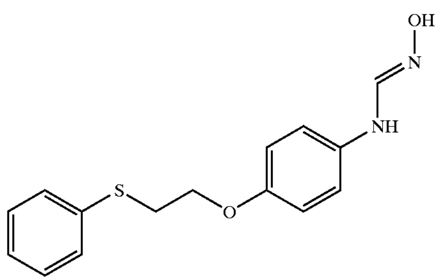 | | 289 | 289 | 287 | 287 | 0.33 | SiO2 (NH) | AcOEt | 116.1 | |
| Comp. 420 | 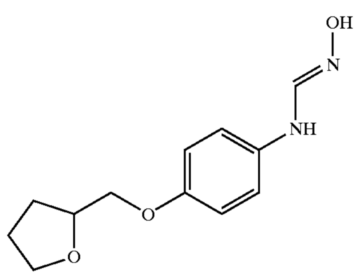 | 147–148.5 | 237 | 237 | 235 | 235 | 0.31 | SiO2 (NH) | AcOEt | 118.6 | 8.0 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 421 | 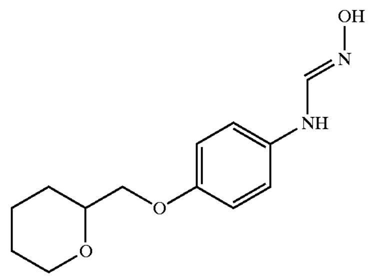 | 153–154.5 | 251 | 251 | 249 | 249 | 0.33 | SiO2 (NH) | AcOEt | 113.3 | 3.9 |
| Comp. 422 | 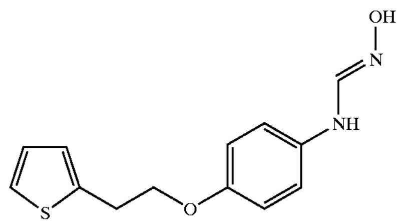 | 132.0–134.0 | 263 | 263 | 261 | 261 | 0.33 | SiO2 (NH) | AcOEt | 121.6 | 1.5 |
| Comp. 423 | 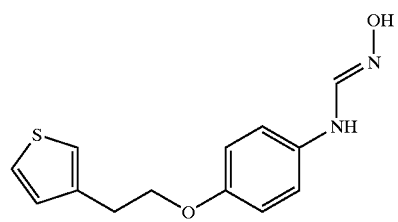 | 132.0–134.5 | 263 | 263 | 261 | 261 | 0.35 | SiO2 (NH) | AcOEt | 118.4 | 2.2 |
| Comp. 424 | 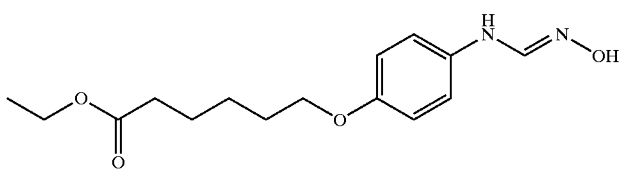 | 102.0–103.5 | | | | | | | | | 1.5 |

TABLE 1-continued

| Comp. | Chemical Structure | mp. | M + H (ESI) | M + H (APCI) | M − H (ESI) | M − H (APCI) | Rf value | TLC* Developing solvent | Inhibition rate (1 μM) | IC50 (nM) |
|---|---|---|---|---|---|---|---|---|---|---|
| Comp. 425 | structure | >300 | | | | | | | | 3.0 |
| Comp. 426 | structure | 101.5–104.0 | | | | | | | | 5.1 |
| Comp. 427 | structure | 108.0–109.5 | | | | | | | | 2.6 |
| Comp. 428 | structure | 143.5–144.5 | | | | | | | | 51.5 |
| Comp. 429 | structure | 159.0–160.5 | | | | | | | | 79.1 |
| Comp. 430 | structure | 139.5–141.0 | | | | | | | | 7.4 |

TABLE 1-continued

| Comp. | Chemical Structure | mp. | M + H (ESI) | M + H (APCI) | M − H (ESI) | M − H (APCI) | Rf value | Developing solvent TLC* | Inhibition rate (1 μM) | IC50 (nM) |
|---|---|---|---|---|---|---|---|---|---|---|
| Comp. 431 | (piperidinyl-pentyloxy-phenyl formamide oxime) | 113.0–115.0 | | | | | | | | 47.7 |
| Comp. 432 | (pyrrolidinyl-pentyloxy-phenyl formamide oxime) | 116.5–117.5 | | | | | | | | 19.5 |
| Comp. 433 | (ethoxycarbonyl-butyloxy-phenyl formamide oxime) | 125.0–127.0 | | | | | | | | 1.5 |
| Comp. 434 | (sodium carboxylate-butyloxy-phenyl formamide oxime) | >300 | | | | | | | | 3.2 |
| Comp. 435 | (diacetoxy-propoxy-phenyl formamide oxime) | 133.0–134.5 | | | | | | | | 2.2 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 436 | (structure with phenyl-O-CH2-CH(OH)-CH2OH and N-OH hydrazone) | 140.5–141.0 | | | | | | | | | 79.2 |
| Comp. 437 | (4-chlorobenzylthio-phenyl NH-CH=N-OH) | | | 293 | 291 | 291 | 0.33 | SiO2 (NH) | AcOEt | 96.1 | |
| Comp. 438 | (cyclohexylthio-phenyl NH-CH=N-OH) | | | 251 | 249 | 249 | 0.36 | SiO2 (NH) | AcOEt | 87.9 | |
| Comp. 439 | (isopropylthio-phenyl NH-CH=N-OH) | 144.1–144.2 | | 211 | 209 | 209 | 0.36 | SiO2 (NH) | AcOEt | 92.3 | 2.9 |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 440 | ![structure] | | | 255 | | 253 | 0.33 | SiO2 (NH) | AcOEt | 102.8 | |
| Comp. 441 | ![structure] | 166 | | 259 | 257 | 257 | 0.33 | SiO2 (NH) | AcOEt | 94.2 | |
| Comp. 442 | ![structure] | | | 225 | 223 | 223 | 0.36 | SiO2 (NH) | AcOEt | 95.7 | |
| Comp. 443 | ![structure] | | | 239 | 237 | 237 | 0.38 | SiO2 (NH) | AcOEt | 103.0 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 444 | HO-N=CH-NH-C6H4-S-CH2CH2-OH | 121.0 | 213 | 213 | 211 | 211 | 0.10 | SiO2 (NH) | AcOEt | 100.7 | 12.1 |
| Comp. 445 | HO-N=CH-NH-C6H4-S-CH2CH2-N(CH3)2 | 112.0 | 240 | 240 | 238 | 238 | 0.18 | SiO2 (NH) | AcOEt | 95.1 | |
| Comp. 446 | HO-N=CH-NH-C6H4-S-CH2-C(O)-OCH3 | | 241 | | | 239 | 0.31 | SiO2 (NH) | AcOEt | 95.9 | |
| Comp. 447 | HO-N=CH-NH-C6H4-S-cyclopentyl | | 237 | | 235 | 235 | 0.36 | SiO2 (NH) | AcOEt | 95.9 | |

TABLE 1-continued
| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 448 | 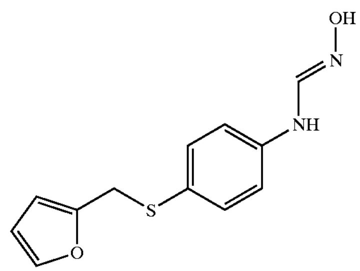 | 125.0–126.5 | 249 | 249 | 247 | 247 | 0.36 | SiO2 (NH) | AcOEt | 109.8 | 1.9 |
| Comp. 449 | 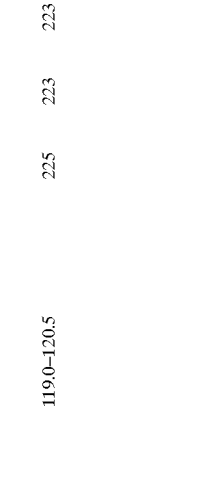 | 119.0–120.5 | 225 | 225 | 223 | 223 | 0.38 | SiO2 (NH) | AcOEt | 105.1 | 1.8 |
| Comp. 450 | 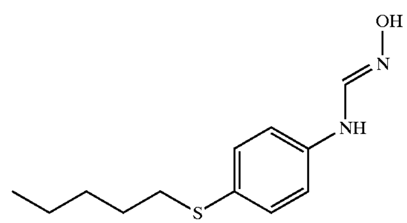 | | 239 | 239 | 237 | 237 | 0.41 | SiO2 (NH) | AcOEt | 105.9 | |
| Comp. 451 | 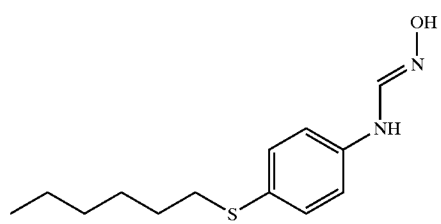 | | 253 | 253 | 251 | 251 | 0.41 | SiO2 (NH) | AcOEt | 97.6 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 452 | ![structure] | | 267 | | 265 | 265 | 0.41 | SiO2 (NH) | AcOEt | 112.3 | |
| Comp. 453 | ![structure] | | 295 | | 293 | 293 | 0.44 | SiO2 (NH) | AcOEt | 95.3 | |
| Comp. 454 | ![structure] | | 288 | | 266 | 266 | 0.26 | SiO2 (NH) | AcOEt | 105.8 | |
| Comp. 455 | ![structure] | | 255 | | 253 | 253 | 0.28 | SiO2 (NH) | AcOEt | 105.6 | |

TABLE 1-continued

| Comp. | Chemical Structure | mp. | M + H (ESI) | M + H (APCI) | M − H (ESI) | M − H (APCI) | Rf value | TLC* | Developing solvent | Inhibition rate (1 μM) | IC50 (nM) |
|---|---|---|---|---|---|---|---|---|---|---|---|
| Comp. 456 | 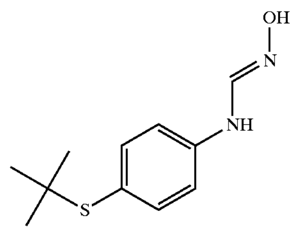 | 143.0–145.0 | 225 | | 223 | 223 | 0.33 | SiO2 (NH) | AcOEt | 94.4 | 6.3 |
| Comp. 457 | 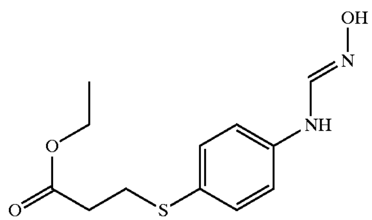 | | | 269 | 267 | 267 | 0.33 | SiO2 (NH) | AcOEt | 112.6 | |
| Comp. 458 | 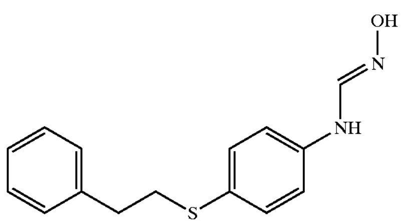 | | | 273 | 271 | 271 | 0.36 | SiO2 (NH) | AcOEt | 116.0 | |
| Comp. 459 | 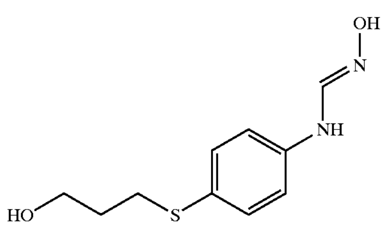 | 108–108.5 | 227 | | 225 | 225 | 0.10 | SiO2 (NH) | AcOEt | 119.0 | 2.4 |

*SiO2(NH): Merck pre-coated plates Silica gel 60 F254, SiO2(NH)(NH): TLC plate NH Fuji Silysia Chemical LTD.

Experimental Example [Inhibitory Effect of 20-HETE Synthase Originated from Rat Kidney Microsome]

Regarding the compounds listed in Table 1, their inhibitory activity to production of 20-HETE was examined. This examination was carried out based on the method described in J. Pharmacol. Exp. Ther., Vol. 268, pp. 474 (1994).

The subject compound for this examination was added to a buffer comprising 50 mM of 3-morpholinopropanesulfonic acid (pH7.4), 5 mM of magnesium chloride and 1 mM of ethylenediaminetetraacetic acid (EDTA) disodium salt.

After that, the rat kidney microsome (microsome fraction prepared from the kidney of a spontaneous hypertension rat (male, 6 weeks of age)) as an enzyme, [5,6,8,9,11,12,14,15] tritium-arachidonic acid (supplied by Amasham) as a substrate, and NADPH (supplied by Sigma) as a coenzyme were added and reacted for 1.5 hours at 37° C.

After the reaction, formic acid was added to stop the reaction, and then acetonitrile (final concentration of 50%) was added and left for 1.5 hours at room temperature.

The activity of 20-HETE synthase was measured by using a high performance liquid chromatograph having a detector for radioactive substances (supplied by Gilson), and equipped with a C18 reversed phase column (Biocyl C18, supplied by Bio-rad).

Setting an amount of 20-HETE production to 100% when no subject compound for examination was added, the concentration of the subject compound at which the production of the 20-HETE was inhibited to 50% and the inhibition rate at which 1 $\mu$M of the subject compound was added are presented together in Table 1.

Referring to Table 1, it was confirmed that the compounds of the present invention have inhibitory activity for production of 20-HETE.

Industrial Applicability

The compounds represented by the general formula (1) or the pharmaceutically-acceptable salts thereof according to the present invention are useful as inhibitors for production of 20-HETE. Therefore, they are useful as medicines, and in particular, therapeutic agents for various diseases in human subjects and animals, which 20-HETE is implicated in, such as kidney diseases, cerebrovascular diseases, or circulatory diseases.

In addition, in the compounds represented by the general formula (1) or the pharmaceutically-acceptable salts thereof, the compounds wherein a non-hydrogen substituent is present at the para position of the hydroxyformamidino moiety on the benzene ring are, in particular, preferable.

In addition, the compounds represented by the general formula (1) or the pharmaceutically-acceptable salts thereof as recited in claims 5 or more are novel compounds and useful in themselves, and also, exhibit the excellent effects described above.

What is claimed is:

1. A hydroxyformamidine compound represented by the formula:

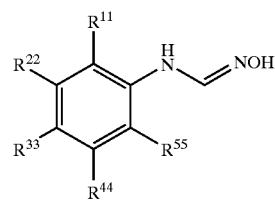

wherein at least one of $R^{11}$ to $R^{55}$ represents a $C_{2-6}$ alkenyl group; a $C_{3-8}$ cycloalkyl $C_{1-6}$ alkyl group; a $C_{3-8}$ cycloalkyl group; a $C_{3-8}$ cycloalkoxy group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-phenyl-2-propenyloxycarbonyl group; a $C_{2-6}$ alkoxycarbonyl $C_{1-6}$ alkyl group; a di($C_{1-6}$ alkyl) amino $C_{2-6}$ alkoxycarbonyl group; a $C_{2-10}$ alkanoylamino group; a $C_{2-6}$ alkanoylamino group substituted with a $C_{1-6}$ alkyl group; a benzoylaamino group; a carbamoyl group; a carbamoyl group mono- or di-substituted with $C_{1-6}$ alkyl or phenyl groups; an N—(N',N'-di($C_{1-6}$ alkyl)amino $C_{1-6}$ alkyl)carbamoyl group; a cyano group; a cyano $C_{1-6}$ alkyl group; a $C_{1-6}$ alkylsulfonyl group; a phenylsulfonyl group; a $C_{1-6}$ alkylthio $C_{1-6}$ alkyl group; a phenylsulfonyl $C_{1-6}$ alkylthio group wherein the benzene ring is substituted with 1 to 5 halogen atoms; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an α-cyanobenzyl group; an α-cyanobenzyl group substituted with 1 to 5 halogen atoms; a benzyl group substituted with a bicyclo(2.2.1)-hept-5-en-2,3-dicarboxyimidyl group; a styryl group; a styryl group substituted with 1 to 5 substituents selected from the group consisting of $C_{1-6}$ alkoxy groups and di($C_{1-6}$ alkyl)amino alkyl groups; a pyrrolidin-1-yl group; a piperidino group; a morpholino group; a pyridyl group; a pyrimidinyl group; a pyriridinyl group substituted with 1 to 3 substituents selected from the group consisting of $C_{1-6}$ alkyl groups and $C_{1-6}$ alkoxy groups; a phthalimidoyl group; a phthalimidoyl group substituted with 1 to 3 halogen atoms; an N-carbazolyl group; a dioxopiperidinyl group substituted with 1 to 3 $C_{1-6}$ alkyl groups; a phenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from the group consisting of halogen atoms, $C_{1-6}$ alkyl groups, and $C_{1-6}$ alkoxy groups; a pyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of halogen atoms, $C_{1-6}$ alkyl groups, and $C_{2-6}$ alkoxycarbonyl groups; a thienopyinmidinylthio group; a thienopyrimidinylthio group substituted with 1 to 3 $C_{1-6}$ alkyl groups; a thienopyridylthio group; a thienopyridylthio group substituted with 1 to 3 $C_{1-6}$ alkyl groups; a benzothiazolylthio group; a benzothiazolylthio group substituted with 1 to 3 halogen atoms; a group represented by the formula:

—Y—$(CR^{61}R^{62})_m$—$(CR^{63}R^{64})_n$—$R^{77}$ (wherein Y represents an oxygen or sulfur atom; $R^{61}$, $R^{62}$, $R^{63}$, and $R^{64}$ are identical or different and represent a hydrogen atom, a halogen atom, a $C_{1-4}$ alkyl group, or a trifluoromethyl group; $R^{77}$ represents a halogen atom; a $C_{3-8}$ cycloalkyl group; a $C_{2-10}$ alkenyl group; a phenyl group substituted with 1 to 3 substituents selected from the group consisting of nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms; a cyano group; a carboxyl group; a $C_{1-6}$ alkoxy group; a $C_{1-6}$ hydroxyalkyl group; a $C_{3-8}$ cycloalkoxy group; a $C_{1-6}$ alkoxy $C_{1-6}$ alkoxy group; a $C_{1-6}$ alkoxy $C_{1-6}$ alkoxy $C_{1-6}$ alkoxy group; a $C_{1-6}$ alkylthio group; a $C_{2-6}$ alkanoyloxy group; a $C_{2-6}$ alkanoyloxy $C_{1-6}$ alkyl group; a phenoxy group; a phenylthio group; an N—($C_{1-6}$ alkyl)toluidino group; a pyrrolidin-1-yl group; a piperidino group; a morpholino group; a pyridyl group; a pyridyl group substituted with a $C_{1-6}$ alkyl group; a piperidino group substituted with a $C_{1-6}$ alkyl group; a pyridyl group substituted with a $C_{1-6}$ alkoxy group; a pyrrolidin-1-yl group substituted with a $C_{1-6}$ alkyl group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperazinyl group; a piperazin-1-yl group substituted with a $C_{1-6}$ alkyl group at the 4-position; a homopiperidinyl group; a homopiperidinyl group substituted with a $C_{1-6}$ alkyl group; a pyridylthio group; a quinolyl group; a furyl group; an oxetanyl group; an oxolanyl group; a dioxolanyl group; a dioxolanyl group substituted with a $C_{1-6}$ alkyl group; an oxanyl group; a dioxanyl group; a dioxanyl group substituted with a $C_{1-6}$ alkyl group; a benzodioxanyl group; a pyrrolidon-1-yl group; a pyrrolidinyl group; an N—($C_{1-6}$ alkyl)pyrrolidinyl group; a piperidinyl group; an N—($C_{1-6}$ alkyl)piperidinyl group; a pyrrolyl group; a thienyl group; a thiazolyl group; a thiazolyl group substituted with 1 to 3 $C_{1-6}$ alkyl groups; a 2,6-purindion-7-yl group substituted with at least one $C_{1-6}$ alkyl group; a furfuryl group; a di($C_{1-6}$ alkyl)amino group; a $C_{2-6}$ alkoxycarbonyl group; or a di($C_{1-6}$ alkyl) amino $C_{1-6}$ alkoxy group; m is an integer of 1 to 6; and n is an integer of 0 to 6); or a group represented by the formula: —$SO_2NR^8R^9$ (wherein $R^8$ and $R^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimnidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively, taken together with the nitrogen atom to which they are bonded, form a 3,5- dioxopiperazin-1-yl group, a pyrrolidinyl group, a piperidino group, or a morpholino group), or alternatively, the two groups adjacent to each other of $R^{11}$ to $R^{55}$, taken together with the benzene ring to which they are bonded, form a phthalimide ring; a phthalimide ring substituted with a $C_{1-6}$ alkyl group; an indole ring; an indane ring; an indazole ring; a benzotriazole ring; an S,S-dioxobenzothiophene ring; a 2,3-dihydroimidazo (2,1-b)benzothiazole ring; a dibenzofuran ring; a dibenzofuran ring substituted with a $C_{1-6}$ alkoxy group; a fluorene ring; a fluorene ring substituted with a halogen atom; a pyrene ring; a carbostyryl ring; a carbostyryl ring substituted with a $C_{1-6}$ alkyl group; a naphthalene ring; a naphthalene ring substituted with 1 to 3 substituents selected from the group consisting of cyano groups, halogen atoms, nitro groups, and $C_{1-6}$ alkyl groups; a 1,2,3,4-tetrahydronaphthalene ring; a quinoline ring; a quinoline ring substituted with a $C_{1-6}$ alkyl group; an isoquinoline ring; a 2-oxo-α-chromene ring; a 2-oxo-α-chromene ring substituted with 1 to 3 substituents selected from the group consisting of $C_{1-6}$ alkyl groups, $C_{1-6}$ alkoxy groups, and $C_{1-6}$ alkoxy $C_{1-6}$ alkyl groups; a cinnolin ring; a cinnolin ring substituted with a $C_{1-6}$ alkyl group; a phthalazindione ring; a benzothiazol ring; a benzothiazol ring substituted with a $C_{1-6}$ alkyl group; a benzodioxorane ring; and a benzobutyrolactone ring, and the remaining groups of $R^{11}$ to $R^{55}$ are identical or different and represent a hydrogen atom, a $C_{1-6}$ alkyl group, a $C_{1-4}$ alkoxy group, a trifluoromethyl group, a nitro group, or a halogen atom, or a pharmaceutically-acceptable salt thereof.

2. The hydroxyformamidine compound or pharmaceutically-acceptable salt thereof, according to claim 1, wherein at least one of $R^{11}$ to $R^{55}$ represents a $C_{3-8}$ cycloalkoxy group; a $C_{3-8}$ cycloalkyl group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-pheny-2-propenyloxycarbonyl group; a $C_{2-6}$ alkoxycarbonyl $C_{1-6}$ alkyl group; a di($C_{1-6}$ alkyl)amino $C_{2-6}$ alkoxycarbonyl group; a $C_{2-10}$ alkanoylamino group; a $C_{2-6}$ alkanoylamino group substituted with a $C_{1-6}$ alkyl group; a benzoylamino group; a carbamoyl group; a carbamoyl group mono- or di-substituted with $C_{1-6}$ alkyl or phenyl groups; an N—(N', N'-di($C_{1-6}$ alkyl)amino $C_{1-6}$ alkyl)carbamoyl group; a cyano group; a cyano $C_{1-6}$ alkyl group; a $C_{1-6}$ alkylsulfonyl group; a phenylsulfonyl group; a $C_{1-6}$ alkylthio $C_{1-6}$ alkyl group; a phenylsulfonyl $C_{1-6}$ alkylthio group wherein the benzene ring is substituted with 1 to 5 halogen atoms; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an α-cyanobenzyl group; an α-cyanobenzyl group substituted with 1 to 5 halogen atoms; a benzyl group substituted with a bicyclo(2.2.1)-hept-5-en-2,3-dicarboxyimidyl group; a styryl group; a styryl group substituted with 1 to 5 substituents selected from the group consisting of $C_{1-6}$ alkoxy groups and di($C_{1-6}$ alkyl)amino alkyl groups; a pyrrolidin-1-yl group; a piperidino group; a morpholino group; a pyridyl group; a pyrimidinyl group; a pyrimidinyl group substituted with 1 to 3 substituents selected from the group consisting of $C_{1-6}$ alkyl groups and $C_{1-6}$ alkoxy groups; a phthalimidoyl group; a phthalimidoyl group substituted with 1 to 3 halogen atoms; an N-carbazolyl group; a dioxopiperidinyl group substituted with 1 to 3 $C_{1-6}$ alkyl groups; a phenylsulfonylamino group; a phenylsulfonylamino group substituted with 1 to 3 $C_{1-6}$ alkyl groups; a $C_{1-6}$ alkylaminosulfonyl $C_{1-6}$ alkyl group; a thiadiazolyl group; an oxadiazolyl group; an oxadiazolyl group substituted with a substituted phenyl group wherein the substituents in the substituted phenyl group are 1 to 3 substituents selected from the group consisting of halogen atoms, $C_{1-6}$ alkyl groups, and $C_{1-6}$ alkoxy groups; a pyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of halogen atoms, $C_{1-6}$ alkyl groups, and $C_{2-6}$ alkoxycarbonyl groups; a thienopyrimidinylthio group; a thienopyrimidinylthio group substituted with 1 to 3 $C_{1-6}$ alkyl groups; a thienopyridylthio group; a thienopyridylthio group substituted with 1 to 3 $C_{1-6}$ alkyl groups; a benzothiazolylthio group; a benzothiazolylthio group substituted with 1 to 3 halogen atoms; or a group represented by the formula: $-SO_2NR^8R^9$ (wherein $R^8$ and $R^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively, taken together with the nitrogen atom to which they are bonded, form a 3,5-dioxopiperadino group, a pyrrolidinyl group, a piperidino group, or a morpholino group), or alternatively, the two groups adjacent to each other of $R^{11}$ to $R^{55}$, taken together with the benzene ring to which they are bonded, form a phthalimide ring; a phthalimide ring substituted with a $C_{1-6}$ alkyl group; an indole ring; an indane ring; an indazole ring; a benzotriazole ring; an S,S-dioxobenzothiophene ring; a 2,3-dihydroimidazo(2,1-b)benzothiazole ring; a dibenzofuran ring; a dibenzofuran ring substituted with a $C_{1-6}$ alkoxy group; a fluorene ring; a fluorene ring substituted with a halogen atom; a pyrene ring; a carbostyryl ring; a carbostyryl ring substituted with a $C_{1-6}$ alkyl group; a naphthalene ring; a naphthalene ring substituted with 1 to 3 substituents selected from the group consisting of cyano groups, halogen atoms, nitro groups, and $C_{1-6}$ alkyl groups; a 1,2,3,4tetrahydronaphthalene ring; a quinoline ring; a quinoline ring substituted with a $C_{1-6}$ alkyl group; an isoquinoline ring; a 2-oxo-α-chromene ring; a 2-oxo-α-chromene ring substituted with 1 to 3 substituents selected from the group consisting of $C_{1-6}$ alkyl groups, $C_{1-6}$ alkoxy groups, and $C_{1-6}$ alkoxy $C_{1-6}$ alkyl groups; a cinnolin ring; a cinnolin ring substituted with a $C_{1-6}$ alkyl group; a phthalazindione ring; a benzothiazol ring; a benzothiazol ring substituted with a $C_{1-6}$ alkyl group; a benzodioxorane ring; and a benzobutyrolactone ring, and the remaining groups of $R^{11}$ to $R^{55}$ are identical or different and represent a hydrogen atom, a $C_{1-6}$ alkyl group, a $C_{1-6}$ alkoxy group, a trifluoromethyl group, a nitro group, or a halogen atom.

3. The hydroxyformamidine compound or pharmaceutically-acceptable salt thereof, according to claim 2, wherein at least one of $R^{11}$ to $R^{55}$ represents a $C_{3-8}$ cycloalkyl group; a $C_{3-8}$ cycloalkoxy group; a $C_{1-6}$ hydroxyalkyl group; a $C_{1-6}$ hydroxyalkyl group substituted with 1 to 6 halogen atoms; a $C_{2-6}$ alkoxycarbonyl group; a 3-pheny-2-propenyloxycarbonyl group; a $C_{2-6}$ alkoxycarbonyl $C_{1-6}$ alkyl group; a di($C_{1-6}$ alkyl)amino $C_{2-6}$ alkoxycarbonyl group; a $C_{2-10}$ alkanoylamino group; a $C_{2-6}$ alkanoylamino group substituted with a $C_{1-6}$ alkyl group; a carbamoyl group; a carbamoyl group mono- or di-substituted with $C_{1-6}$ alkyl or phenyl groups; an N—(N',N'-di($C_{1-6}$ alkyl)amino $C_{1-6}$ alkyl)carbamoyl group; a cyano group; a cyano $C_{1-6}$ alkyl group; a $C_{1-6}$ alkylsulfonyl group; a phenylsulfonyl group; a $C_{1-6}$ alkylthio $C_{1-6}$ alkyl group; a phenyl group; a benzyl group; a phenyl group substituted with 1 to 3 substituents selected from the group consisting of cyano groups, halogen atoms, $C_{1-6}$ alkyl groups, and $C_{1-6}$ alkoxy groups; a biphenyl group; an α-cyanobenzyl group; an α-cyanobenzyl group substituted with 1 to 5 halogen atoms; a pyrrolidino group; a piperidino group; a morpholino group; a pyridyl group; a pyrimidinyl group; a pyrimidinyl group substituted with 1 to 3 substituents selected from the group consisting of $C_{1-6}$ alkyl groups and $C_{1-6}$ alkoxy groups; a pyrrolidinyl group; a pyrazolyl group; a pyrazolyl group substituted with 1 to 3 substituents selected from the group consisting of halogen atoms, $C_{1-6}$ alkyl groups, and trifluoromethyl groups; a furyl group; a furyl group substituted with 1 to 3 substituents selected from the group consisting of halogen atoms, $C_{1-6}$ alkyl groups, and $C_{2-6}$ alkoxycarbonyl groups; or a group represented by the formula: $-SO_2NR^8R^9$ (wherein $R^8$ and $R^9$ are identical or different and represent a hydrogen atom, a $C_{1-10}$ alkyl group, a $C_{2-6}$ alkanoyl group, an isoxazolyl group, an isoxazolyl group substituted with 1 to 3 $C_{1-6}$ alkyl groups, a thiadiazolyl group, a thiadiazolyl group substituted with 1 to 3 $C_{1-6}$ alkyl groups, a thiazolyl group, a thiazolyl group substituted with 1 to 3 $C_{1-6}$ alkyl groups, a pyridyl group, a pyridyl group substituted with 1 to 3 $C_{1-6}$ alkyl groups, a pyrimidinyl group, a pyrimidinyl group substituted with 1 to 3 $C_{1-6}$ alkyl groups, a pyrimidinyl group substituted with 1 to 3 $C_{1-6}$ alkoxy groups, a pyridazinyl group, a pyridazinyl group substituted with 1 to 3 $C_{1-6}$ alkoxy groups, an indazolyl group, or a carbamoyl group mono- or di-substituted with $C_{1-6}$ alkyl groups, or alternatively, taken together with the nitrogen atom to which they are bonded, form a 3,5-dioxopiperazin-1-yl group, a pyrrolidinyl group, a piperidino group, or a morpholino group) and the remaining groups of $R^{11}$ to $R^{55}$ are identical or different and represent a hydrogen atom, a $C_{1-4}$ alkyl group, a $C_{1-4}$ alkoxy group, a trifluoromethyl group, a nitro group, or a halogen atom.

4. The hydroxyformamidine compound or pharmaceutically-acceptable salt thereof, according to claim 1, wherein at least one of $R^{11}$ to $R^{55}$ represents a group represented by the formula: $-Y-(CR^{61}R^{62})_m-(CR^{63}R^{64})_n-R^{77}$ (wherein Y represents an oxygen or sulfur atom; $R^{61}$, $R^{62}$, $R^{63}$, and $R^{64}$ are identical or different and represent a hydrogen atom, a halogen atom, a $C_{1-6}$ alkyl group, or a trifluoromethyl group; $R^{77}$ represents a halogen atom; a $C_{3-8}$ cycloalkyl group; a $C_{2-10}$ alkenyl group; a phenyl group substituted with 1 to 3 substituents selected from the group consisting of nitro groups, cyano groups, $C_{1-6}$ alkyl groups, $C_{1-6}$ alkoxy groups, $C_{1-6}$ alkylthio groups, phenyl groups, phenoxy groups, phenethyl groups, $C_{2-6}$ alkoxycarbonyl groups, and halogen atoms; a cyano group; a carboxyl group; a $C_{1-6}$ alkoxy group; a $C_{1-6}$ hydroxyalkyl group; a $C_{3-8}$ cycloalkoxy group; a $C_{1-6}$ alkoxy $C_{1-6}$ alkoxy group; a $C_{1-6}$ alkoxy $C_{1-6}$ alkoxy $C_{1-6}$ alkoxy group; a $C_{1-6}$ alkylthio group; a $C_{2-6}$ alkanoyloxy group; a $C_{2-6}$ alkanoyloxy $C_{1-6}$ alkyl group; a phenoxy group; a phenylthio group; an N—($C_{1-6}$ alkyl)toluidino group; a pyrrolidin-1-yl group; a piperidino group; a morpholino group; a pyridyl group; a pyridyl group substituted with a $C_{1-6}$ alkyl group; a piperidino group substituted with a $C_{1-6}$ alkyl group; a pyridyl group substituted with a $C_{1-6}$ alkoxy group; a pyrrolidin-1-yl group substituted with a $C_{1-6}$ alkyl group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperazinyl piperidinyl group; a piperazin-1-yl group substituted with a $C_{1-6}$ alkyl group at the 4-position; a homopiperidinyl group; a homopiperidinyl group substituted with a $C_{1-6}$ alkyl group; a pyridylthio group; a quinolyl group; a furyl group; an oxetanyl group; an oxolanyl group; an dioxolanyl group; a dioxolanyl group substituted with a $C_{1-6}$ alkyl group; an oxanyl group; a dioxanyl group; a dioxanyl group substituted with a $C_{1-6}$ alkyl group; a benzodioxanyl group; a pyrrolidon-1-yl group; a pyrrolidinyl group; an N—($C_{1-6}$ alkyl)pyrrolidinyl group; a piperidinyl group; an N—($C_{1-6}$ alkyl)piperidinyl group; a pyrrolyl group; a thienyl group; a thiazolyl group; a thiazolyl group substituted with 1 to 3 $C_{1-6}$ alkyl groups; a 2,6-purindion-7-yl group substituted with $C_{1-6}$ alkyl group(s); a furfuryl group; a di($C_{1-6}$ alkyl)amino group; a $C_{2-6}$ alkoxycarbonyl group; or a di($C_{1-6}$ alkyl) amino $C_{1-6}$ alkoxy group; m is an integer of 1 to 6; and n is an integer of 0 to 6), and the remaining groups of $R^{11}$ to $R^{55}$ are identical or different and represent a hydrogen atom, a $C_{1-4}$ alkyl group, a $C_{1-4}$ alkoxy group, a trifluoromethyl group, a nitro group, or a halogen atom.

5. The hydroxyformamidine compound or pharmaceutically-acceptable salt thereof, according to claim 4, wherein at least one of $R^{11}$ to $R^{55}$ represents a group represented by the formula: —O—$(CR^{61}R^{62})_m$—$(CR^{63}R^{64})_n$—$R^{77}$ (wherein $R^{61}$, $R^{62}$, $R^{63}$, and $R^{64}$ are identical or different and represent a hydrogen atom, a halogen atom, a $C_{1-4}$ alkyl group, or a trifluoromethyl group; $R^{77}$ represents a di($C_{1-6}$ alkyl)amino group; a di($C_{1-6}$ alkyl)amino $C_{1-6}$ alkoxy group; a piperidyl group; a piperidyl group substituted with a $C_{1-6}$ alkyl group; a piperidino group; a piperidino group substituted with a $C_{1-6}$ alkyl group; a pyridyl group; a pyridyl group substituted with a $C_{1-6}$ alkyl group; a pyridyl group substituted with a $C_{1-6}$ alkoxy group; a pyridylthio group; a pyrrolidon-1-yl group; a pyrrolidinyl group; a pyrrolidinyl group substituted with a $C_{1-6}$ alkyl group; a pyrrolyl group; a thienyl group; a thiazolyl group; a morpholino group; a morpholino group substituted with a $C_{1-6}$ alkyl group; a morpholinyl group; a morpholinyl group substituted with a $C_{1-6}$ alkyl group; a homomorpholinyl group; a thiomorpholino group; a thiomorpholino group substituted with a $C_{1-6}$ alkyl group; a thiomorpholinyl group; a thiomorpholinyl group substituted with a $C_{1-6}$ alkyl group; a piperazinyl group; piperazin-1-yl group substituted with a $C_{1-6}$ alkyl group at the 4-position; a homopiperidinyl group; or a homopiperidinyl group substituted with a $C_{1-6}$ alkyl group; m is an integer of 1 to 6; and n is an integer of 0 to 6), and the remaining groups of $R^{11}$ to $R^{55}$ are identical or different and represent a hydrogen atom, a $C_{1-6}$ alkyl group, a $C_{1-4}$ alkoxy group, a trifluoromethyl group, a nitro group, or a halogen atom.

6. The hydroxyformamidine compound or pharmaceutically-acceptable salt thereof, according to any one of claims 3 to 5, wherein $R^{11}$, $R^{22}$, $R^{44}$, and $R^{55}$ represent hydrogen atoms.

7. A therapeutic method for treatment of a cerebrovascular disease, said method comprising administering to a patient having a cerebrovascular disease, an effective amount of the hydroxyformamidine compound or a pharmaceutically-acceptable salt thereof according to any one of claims 1 to 5.

8. A therapeutic method for treatment of a cerebrovascular disease, said method comprising administering to a patient having a cerebrovascular disease, an effective amount of the hydroxyformamidine compound or a pharmaceutically-acceptable salt thereof according to claim 6.

9. The hydroxyformamidine compound N-(3-chloro-4-morpholine-4-yl)phenyl-N'-hydroxyimidoformamidine.

10. A method for treatment of a cerebrovascular disease, said method comprising administering to a subject having said diseases, wherein said disease is caused by the activity of 20-hydroxyeicosatetraenoic acid, a pharmaceutically-effective amount of N-(3-chloro-4-morpholin-4-yl)phenyl-N'-hydroxyimidoformamidine or a pharmaceutically-acceptable salt thereof, and a pharmaceutically acceptable carrier or diluent.

* * * * *